US00RE47739E

(19) United States
(12) Reissued Patent
Barvian et al.

(10) Patent Number: US RE47,739 E
(45) **Date of Reissued Patent: *Nov. 26, 2019**

(54) 2-(PYRIDIN-2-YLAMINO)-PYRIDO[2,3-D] PYRIMIDIN-7-ONES

(71) Applicant: Warner-Lambert Company LLC, New York, NY (US)

(72) Inventors: Mark Barvian, Ann Arbor, MI (US); Richard John Booth, Ann Arbor, MI (US); John Quinn, III, Ann Arbor, MI (US); Joseph Thomas Repine, Ann Arbor, MI (US); Derek J. Sheehan, Dexter, MI (US); Peter Lawrence Toogood, Ann Arbor, MI (US); Scott Norman Vanderwel, Ann Arbor, MI (US); Hairong Zhou, Ann Arbor, MI (US)

(73) Assignee: Warner-Lambert Company LLC, New York, NY (US)

( * ) Notice: This patent is subject to a terminal disclaimer.

(21) Appl. No.: 16/048,143

(22) Filed: Jul. 27, 2018

Related U.S. Patent Documents

Reissue of:
(64) Patent No.: 7,208,489
Issued: Apr. 24, 2007
Appl. No.: 11/046,126
Filed: Jan. 28, 2005

U.S. Applications:
(63) Continuation of application No. 10/345,778, filed on Jan. 16, 2003, now Pat. No. 6,936,612.

(60) Provisional application No. 60/350,877, filed on Jan. 22, 2002.

(51) Int. Cl.

| | |
|---|---|
| ***C07D 401/14*** | (2006.01) |
| ***C07D 471/04*** | (2006.01) |
| ***A61K 31/519*** | (2006.01) |
| ***A61K 31/675*** | (2006.01) |
| *A61K 31/444* | (2006.01) |

(52) U.S. Cl.
CPC ..... *C07D 471/04* (2013.01); *A61K 31/519* (2013.01); *A61K 31/675* (2013.01)

(58) Field of Classification Search
None
See application file for complete search history.

(56) References Cited

U.S. PATENT DOCUMENTS

| | | | | |
|---|---|---|---|---|
| 4,372,957 | A | 2/1983 | Duch et al. | |
| 4,959,474 | A | 9/1990 | Grivsky | |
| 5,409,930 | A | 4/1995 | Spada et al. | |
| 5,426,110 | A | 6/1995 | Gossett et al. | |
| 5,620,981 | A | 4/1997 | Blankley et al. | |
| 5,733,914 | A | 3/1998 | Blankley et al. | |
| 5,801,183 | A | 9/1998 | Keana et al. | |
| 5,880,130 | A | 3/1999 | Thomas | |
| 5,948,786 | A | 9/1999 | Fujiwara et al. | |
| 6,498,163 | B1 * | 12/2002 | Boschelli et al. | 514/264.1 |
| 6,696,566 | B2 | 2/2004 | Chen et al. | C07D 519/00 544/261 |
| 6,720,332 | B2 | 4/2004 | Dickerson et al. | |
| 6,936,612 | B2 | 8/2005 | Barvian et al. | |
| 7,022,711 | B2 | 4/2006 | Hamby et al. | |
| 7,189,712 | B2 | 3/2007 | Brown et al. | |
| 7,208,489 | B2 | 4/2007 | Barvian et al. | |
| 7,279,473 | B2 | 10/2007 | Badiang et al. | |
| 7,345,171 | B2 | 3/2008 | Beylin et al. | |
| 7,456,168 | B2 | 11/2008 | Barvian et al. | |
| 7,501,425 | B1 * | 3/2009 | Dobrusin | C07D 487/04 514/262.1 |

(Continued)

FOREIGN PATENT DOCUMENTS

| | | | |
|---|---|---|---|
| EP | 0021292 | A1 | 1/1981 |
| EP | 0278686 | A1 | 8/1988 |

(Continued)

OTHER PUBLICATIONS

Tully, P.S. (Mar. 27, 2019). Notice of Paragraph IV Certification of U.S. Pat. Nos. 6,936,612, 7,208,489, and 7,456,168 Concerning ANDA 213152 for Palbociclib Capsule, 75, 100 and 125 mg [Letter to Whom it May Concern]. Chicago, Illinois.

Coyle, S.M. (Mar. 19, 2019). Notice of Paragraph IV Certification Regarding Alembic Pharmaceuticals Limited's Palbociclib Capsules (Reference Listed Drug: IBRANCE®, NDA No. 207103) with respect to U.S. Pat. No. 6,936,612 [Letter to Pfizer Inc. and Warner-Lambert Company]. Hartford, Connecticut.

Scott, I. (Mar. 14, 2019). Apotex's Palbociclib Oral Capsule, 75 mg, 100 mg and 125 mg—Notice of Certification Under 21 U.S.C. § 355(j)(2)(B)(ii) (§ 505(j)(2)(B)(ii) of the Federal Food, Drug and Cosmetic Act) and 21 C.F.R. § 314.95 [Letter to Pfizer Inc. and Warner-Lambert Company]. Chicago, Illinois.

(Continued)

*Primary Examiner* — Timothy J. Kugel
(74) *Attorney, Agent, or Firm* — Carl A. Morales, Esq.; Blaine M. Hackman, Esq.; Dechert LLP

(57) ABSTRACT

The present invention provides substituted 2-aminopyridines useful in treating cell proliferative disorders. The novel compounds of the present invention are potent inhibitors of cyclin-dependent kinases 4 (cdk4)

II

8 Claims, No Drawings

(56) References Cited

U.S. PATENT DOCUMENTS

| | | | | |
|---|---|---|---|---|
| 7,507,834 | B2 | 3/2009 | Tang | |
| 7,781,583 | B2 | 8/2010 | Erdman et al. | |
| 7,863,278 | B2 | 1/2011 | Beylin et al. | |
| 2003/0130286 | A1 | 7/2003 | Denny et al. | |
| 2003/0149001 | A1 | 8/2003 | Barvian et al. | |
| 2004/0236084 | A1 | 11/2004 | Biwersi et al. | |
| 2005/0009849 | A1* | 1/2005 | Veach et al. | 514/264.11 |
| 2005/0059670 | A1 | 3/2005 | Beylin et al. | |
| 2005/0137214 | A1 | 6/2005 | Barvian et al. | |
| 2006/0293338 | A1 | 12/2006 | Hasegawa et al. | |
| 2007/0179118 | A1 | 8/2007 | Barvian et al. | |
| 2008/0125588 | A1 | 5/2008 | Erdman et al. | |

FOREIGN PATENT DOCUMENTS

| | | | | |
|---|---|---|---|---|
| WO | WO 1992/20642 | | 11/1992 | |
| WO | WO 1995/09845 | | 4/1995 | |
| WO | WO 1995/15952 | | 6/1995 | |
| WO | WO 1996/15128 | | 5/1996 | |
| WO | 1996022990 | A2 | 8/1996 | |
| WO | WO 1996/34867 | | 11/1996 | |
| WO | WO 1997/38992 | | 10/1997 | |
| WO | WO 1998/033798 | | 8/1998 | |
| WO | 1999021845 | A2 | 5/1999 | |
| WO | WO-9961444 | A2 * | 12/1999 | C07D 471/04 |
| WO | 2000012485 | A1 | 3/2000 | |
| WO | 2001007411 | A1 | 2/2001 | |
| WO | WO 2001055148 | | 8/2001 | |
| WO | WO-0170741 | A1 * | 9/2001 | C07D 471/04 |
| WO | WO 2001070741 | | 9/2001 | |
| WO | WO 2002012238 | | 2/2002 | |
| WO | 2002059125 | A1 | 8/2002 | |
| WO | WO-02064594 | A2 * | 8/2002 | C07D 471/04 |
| WO | WO 2002064594 | | 8/2002 | |
| WO | WO 2003/062236 | | 7/2003 | |

OTHER PUBLICATIONS

Patel, S.K. (Mar. 27, 2019). Notification Pursuant to § 505(j)(2)(B)(ii) of the Federal Food, Drug, and Cosmetic Act (21 U.S.C. § 335(j)(2)(B)(ii) and 21 C.F.R. § 314.95) [Letter to Pfizer inc. and Warner-Lambert Co.]. Chicago, Illinois.

Sorenson, C.J. (Mar. 18, 2019). Notice of Paragraph IV Certification Regarding Cipla Limited's Palbociclib Capsules 75mg, 100mg, 125mg (Reference Listed Drug: IBRANCE®, NDA No. 207103) With Respect to U.S. Pat. Nos. 6,936,612; 7,208,489 and 7,456,168. [Letter to Pfizer Inc.; Wamer-Lambert Company; Hsu, W.L.; Waldron, R. F.; Lanker, D. and Kite, M. Y.]. Minneapolis, Minnesota.

Frederickson III, R. (Mar. 19, 2019). Notice of Paragraph IV Certification Regarding U.S. Pat. Nos. 6,936,612, 7,208,489, and 7,456,168 Pursuant to § 505(j)(2)(B)(iv) of the Federal Food, Drug, and Cosmetic Act [Letter to Pfizer Inc. and Warner-Lambert Co.]. Boston, Massachusetts.

Thallemer, J. (Mar. 12, 2019). Notice of Certification Under 21 U.S.C. § 355(j)(2)(B)(ii) (§ 505(j)(2)(B)(ii) of the Federal Food, Drug and Cosmetic Act) and 21 C.F.R. § 314.95 [Letter to Pfizer Inc. and Warner Lambert Company]. Piscataway, New Jersey.

Mukerjee D.R. (Mar. 18, 2019). Notice of Paragraph IV Certification Regarding U.S. Pat. Nos. 6,936,612; 7,208,489; and 7,456,168 Pursuant to Section 505a)(2)(B)(iv) of the Federal Food, Drug, and Cosmetic Act and 21 C.F.R. § 314.95 for ANDA No. 213141 (IBRANCE® (palbociclib 125 mg, 100 mg, and 75 mg capsules)) [Letter to Pfizer Inc. and Warner-Lambert Company LLC]. New York, New York.

Hayworth, M.M. (Mar. 18, 2019). Notification of Certification of Invalidity, Unenforceability and/or Non-Infringement for U.S. Pat. Nos. 6,936,612, 7,208,489, and 7,456,168 Pursuant to Section 505(j)(2)(B)(iv) of the Federal Food, Drug, and Cosmetic Act [Letter to Pfizer Inc.; Warner-Lambert Company LLC; Hsu, W.L.; Waldron, R.F. and Lanker, D.]. Alexandria, Virginia.

Bao, H. (Mar. 20, 2019). Qilu Pharmaceutical's Palbociclib Oral Capsule, 75 mg, 100 mg and 125 mg—Notice of Certification Under 21 U.S.C. § 355(j)(2)(B)(ii) (§ 505(j)(2)(B)(ii) of the Federal Food, Drug and Cosmetic Act) and 21 Q.F.R. § 314.95 [Letter to Pfizer Inc. and Warner-Lambert Company]. P.R. China.

Speier, G.J. (Mar. 27, 2019). ANDA No. 213107 Palbociclib Capsules, 75 mg, 100 mg and 125 mg Paragraph IV Certification Concerning U.S. Pat. Nos. 6,936,612 and 7,208,489 [Letter to Pfizer Inc.]. Minneapolis, Minnesota.

Majiduddin, F. (Mar. 21, 2019). Notice of ANDA No. 213088 Paibociclib Capsules 75 mg, 100 mg and 125 mg, With Paragraph IV Certifications Concerning U.S. Pat. Nos. 6,936,612, 7,208,489 and 7,456,168 [Letter to Pfizer, Inc.]. Parsippany, New Jersey.

Khera, B. (Mar. 26, 2019). IBRANCE (palbociclib) capsules, 75 mg, 100mg, and 125 mg, ANDA No. 213098, U.S. Pat. Nos. 6,936,612, 7,208,489, and 7,456,168 [Letter to Pfizer Inc. and Warner-Lambert Company LLC]. Pennington, New Jersey.

Toogood, P.L., "Cyclin-Dependent Kinase Inhibitors for Treating Cancer," Med Res Rev, 2001, 21:6 (487-98).

Honma et al., "Structure-based Generation of a New Class of Potent Cdk4 Inhibitors: New de Novo Design Strategy and Library Design," J. Med. Chem., 44:4615-4627 (2001).

Honma et al., "A Novel Approach for the Development of Selective Cdk4 Inhibitors: Library Design Based on Locations ofCdkd Specific Amino Acid Residues," J. Med. Chem., 44(26): 4628-40 (2001).

Trumpp-Kallmeyer, S. et al., "Development of a Binding Model to Protein Tyrosine Kinases for Substituted Pyrido [2,3-d]pyrimidine Inhibitors," J. Med. Chem. (1998), 41, 1752-1763.

Klutchko et al., "2-Substituted Aminopyrido12,3-dl pyrimidin-7(8H)-ones. Structure-Activity Relationships Against Selected Tyrosine Kinases and in Vitro and in Vivo Anticancer Activity," J. Med. Chem., vol. 41, 3276-92 (1998).

Patani et al., "Bioisosterism: A Rational Approach in Drug Design," Chem. Rev., vol. 96, 3147-3176 (1996).

Shewchuk et al., "Binding Mode of the 4-Anilinoquinazoline Class of Protein Kinase Inhibitor: X-ray Crystallographic Studies of 4-Anilinoquinazolines Bound to Cyclin-Dependent Kinase 2 and p38 Kinase," J. Med. Chem., 2000, 43, 133-138.

Ikuta et al., "Crystallographic Approach to Identification of Cyclin-dependant Kinase 4 (CDK4)-specific Inhibitors by Using CDK4 Mimic CDK2 Protein," The Journal of Biological Chemistry, 276(29): 27548-54 (2001).

Hanks et al., "Protein Kinase Catalytic Domain Sequence Database: Identification of Conserved Features of Primary Structure and Classification of Family Members," Methods in Enzymology, vol. 200, 38-62 (1991).

Schulze-Gahmen et al., "High-Resolution Crystal Structures of Human Cyclin-Dependent Kinase 2 with and without ATP: Bound Waters and Natural Ligand as Guides for Inhibitor Design," J. Med. Chem., (1996) 39(23): 4540-4546.

Boschelli et al., "Synthesis and Tyrosine Kinase Inhibitory Activity of a Series of 2-Amino-8H-pyrido[2,3-d] pyrimidines: Identification of Potent, Selective Platelet-Derived Growth Factor Receptor Tyrosine Kinase Inhibitors," J. Med. Chem., vol. 41(22); 4365-4377 (1998).

Fry et al., "Cell Cycle and Biochemical Effects of PD 0183812, A Potent Inhibitor of the Cyclin D-Dependent Kinases CDK4 and CDK6," J. Bio. Chem. vol. 276, 16617-23 (2001).

Fry et al., "Strategies for the Discovery of Novel Tyrosine Kinase Inhibitors with Anticancer Activity," Anti-Cancer Drug Design vol. 9, 331-351 (1994).

Moasser et al., "Inhibition of Src Kinases by a Selective Tyrosine Kinase Inhibitor Causes Mitotic Arrest," Cancer Research vol. 59, 6145-52 (1999).

Thornber, C.W., "Isosterism and Molecular Modification in Drug Design," Chem. Soc. Rev., 8:563-580, 1979.

Nurse, P., "A Long Twentieth Century of the Cell Cycle and Beyond," Cell, vol. 100, 71-78 (2000).

Kent et al., "Characterization of Novel Inhibitors of Cyclin-Dependent Kinases," Biochemical and Biophysical Research Communications, vol. 260, 768-774 (1999).

Kubo et al., "The p16 Status of Tumor Cell Lines Identities Small Molecule Inhibitors Specific for Cyclin-dependent Kinase 4," Clinical Cancer Research, vol. 5, 4279-4286 (1999).

(56) References Cited

OTHER PUBLICATIONS

Kataoka et al., "Down-regulation of bcl-2 is associated with p161NK4-mediated apoptosis in non-small cell lung cancer cells," Oncogene, vol. 19, 1589-1595 (2000).
Soni et al., "Inhibition of Cyclin-Dependent Kinase 4 (Cdk4) by Fascaplysin, a Marine Natural Product," Biochemical and Biophysical Research Communications, vol. 275, 877-884 (2000).
Adeyeye, Moji, ed., Preformulation in Solid Dosage Form Development (Informa Healthcare, 2008) Ch. 2, 3, pp. 63-80.
Anderson et al.: "Pyridopyrimidines. 6. Nucleophilic Substitutions in the Pyrido[2,3-d]pyrimidine Series," J. Org. Chem., vol. 42, 1977, Washington, pp. 993-994.
Baker, B.R., et al.: "Analogs of Tetrahydrofolic acid. XIX. On the Mode of Binding of the Pyrimidyl Moiety . . . ," J. Heterocyclic. Chem., vol. 1, 1964, Albuquerque, pp. 263-270.
Barvian et al., "Pyrido[2,3-d]pyrimidin-7-one Inhibitors of Cyclin-Dependent Kinases," J. Med. Chem. 2000, 43, 4606-4616.
Bastin, et al., Org. Process Res. & Devlop. 2000, 4, 427-435.
Berge et al., "Pharmaceutical Salts," J. Pharm. Sciences, vol. 66, No. 1, 1977, 1-19.
Borrel, J.I. et al.: "An unequivocal Synthesis of 4-amino-1,5,6,8-tetra-hydropyrido[2,3-d]pyrimidine-2,7-diones and . . . ," Coll. Czech. Chem. Commun., vol. 61, No. 6, 1996, Prague, pp. 901-909.
Costa Rican Docket No. 2012-0129, Patent Opposition of International Publication WO2005082903 dated Sep. 26, 2012.
Cristofanilli et al., "Fulvestrant plus palbociclib versus fulvestrant plus placebo for treatment of hormone-receptor-positive, HER2-negative metastatic breast cancer that progressed on previous endocrine therapy (PALOMA-3): final analysis of the multicentre, double-blind, phase 3 randomised controlled trial," Lancet Oncol 2016; 17: 425-39.
Finn et al., "Palbociclib and Letrozole in Advanced Breast Cancer," N Engl J Med 2016;375:1925-36.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," Lancet Oncol 2015; 16: 25-35.
Fischer, P., et al., "Recent Advances and New Directions in the Discovery and Development of Cyclin-Dependent Kinase Inhibitors," Current Opinion in Drug Discovery, 2001, 623-634, vol. 4.
Fry et al., "Specific inhibition of cyclin-dependent kinase 4/6 by PD 0332991 and associated antitumor activity in human tumor xenografts," Mol. Cancer Ther. 2004; 3:1427-1438. Published online Nov. 12, 2004.
Fry, D., et al., "Inhibitors of Cyclin-Dependent Kinases as Therapeutic Agents for the Treatment of Cancer," Current Opinion in Oncologic, Endocrine & Metabolic Investigational Drugs, 2000, 40-59, vol. 2, No. 1.
Gould, Intern'l., J. Therap., 33, 201, 1986.
Hurlbert, B.S., "Studies on Condensed Pyrimidine Systems. XXIII. Synthesis of 2,4-Diaminopyrido[2,3-d]pyrimdiines . . . ," J. Med. Chem., vol. 11, 1968, Washington, pp. 703-707.
International Preliminary Examination Report corresponding to International Application No. PCT/IB03/00059 dated May 13, 2004.
International Search Report relating to International Application No. PCT/US98/01343 dated Jul. 21, 1998.
Layzer, Degenerative Diseases of the Nervous System, Cecil Textbook of Medicine, 20th Edition, vol. 2, pp. 2050-2057, 1996.
Liu, Rong, ed., Water-Insol. Drug Formul. (CRC Press, 2008) Ch. 15, pp. 417-435.
Ministerial Order for Lebanese Patent No. 6633, Official Gazette No. 28, Jun. 19, 2003, 4382-4383.
Modiano, et al., J. Immuno., 2000, pp. 6693-6702.
Morris et al., Intern'l, J. Pharma. 105, 1994, 209-217.
Patent Term Extension Application for U.S. Pat. No. 6936612 dated Mar. 27, 2015.
Patent Term Extension Application for U.S. Pat. No. 7208489 dated Mar. 27, 2015.
Rane, et al., Nature America , vol. 22, pp. 44-52, 1999.
Rewcastle, G.W. et al., "Tyrosine Kinase Inhibitors. 10. Isomeric 4-(3-Bromophenyl)Aminopyrido D-Pyrimidines Are Potent ATP Binding Site Inhibitors of the Tyrosine Kinase Function of the Epidermal Growth Factor Receptor", Journal of Medicinal Chemistry, vol. 39, No. 9, 1996, pp. 1823-1835.
Schoffstall, A.M., et al.: "Synthesis of 5,6-Dihydropyrido[2,3-d]pyrimidine Derivatives Directly from Acyclic Precursors," J. Org. Chem., vol. 36, No. 16, 1971, Washington, pp. 2385-2387.
Serajuddin, Advan. Drug Deliv., Rev. 59 (2007) 603-616.
Sherr, Cancer Cell Cycles, Science, vol. 274, Issue 5293, pp. 1672-1677, Dec. 1996.
Sicinski, "Killer Breast Cancer Therapy Hope, http://news.bbc.co.uk/go/pr/fr/~/1/hi/health/4619900.stm," BBC News/Health, 2006.
Sielecki, T., et al., "Cyclin-Dependent Kinase Inhibitors: Useful Targets in Cell Cycle Regulation," Journal of Medicinal Chemistry, 2000, 1-18, vol. 43, No. 1.
Swarbrick et al., eds., Encyclopedia of Pharm. Tech. 13 (Marcel Dekker, NY, 1996, pp. 453-499.
Toogood et al., "Discovery of a Potent and Selective Inhibitor of Cyclin-Dependent Kinase 4/6," J. Med. Chem. 2005, 48, 2388-2406.
Vanderwel et al., "Pyrido[2,3-d]pyrimidin-7-ones as Specific Inhibitors of Cyclin-Dependent Kinase 4," J. Med. Chem. 2005, 48, 2371-2387.
Victory, P. et al. "New Synthesis of pyrido[2,3-d]pyrimidines. 1. Reaction of 6-alkoxy-5-cyano-3,4-dihydro-2-pyridones with Guanidine and Cyanamide," Heterocycles, vol. 23, No. 5, 1985, pp. 1135-1141.
Victory, P. et al., "Cyclisation of Dinitriles by hydrogen halides. 1. Hydrogen bromide," Heterocycles, vol. 23, No. 8, 1985, pp. 1947-1950.
Webster, K. et al., "Novel Drugs Targeting the Cell Cycle," Emerging Drugs, 2000, 45-59, vol. 5, No. 1.
Wolf, Kidney Intern'l., vol. 58, Suppl. 77, 2000, pp. S-59-S-66.
Blain, S., et al., "Differential Interaction of the Cyclin-Dependent Kinase (Cdk) Inhibitor," *The Journal of Biological Chemistry*, 1997, 25863-25872 vol. 272, No. 41.
Damasio, A, "Alzheimer's Disease and Related Dementias," *Cecil Textbook Of Medicine*, 20$^{th}$ Edition, 1996, 1992-1996, vol. 2.
Douglas, Jr., R., "Introduction to Viral Diseases," *Cecil Textbook of Medicine*, 20$^{th}$ Edition, 1996, 1739-1742, vol. 2.
Lu Valle, P., et al., "Cell Cycle Control in Growth Plate Chondrocytes," *Frontiers in Bioscience* 5, 2000, d493-503.
Simone, J., "Oncology: Introduction," *Cecil Textbook of Medicine*, 20$^{th}$ Edition, 1996, 1004-1008, vol. 1.
Frederickson III, R. (Jun. 11, 2019). Updated Notice of Paragraph IV Certification Regarding U.S. Pat. No. 7,456,168 Pursuant to § 505(j)(2)(B)(iv) of the Federal Food, Drug, and Cosmetic Act [Letter to Pfizer Inc. and Warner-Lambert Co.]. Boston, Massachusetts.

* cited by examiner

2-(PYRIDIN-2-YLAMINO)-PYRIDO[2,3-D] PYRIMIDIN-7-ONES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present application is a continuation of application having U.S. application Ser. No. 10/345,778, filed on Jan. 16, 2003, now U.S. Pat. No. 6,936,612 which claims benefit of provisional application U.S. Ser. No. 60/350,877, filed on Jan. 22, 2002.

FIELD OF THE INVENTION

This invention relates to substituted 2-amino pyridines that are potent inhibitors of cyclin-dependent kinase 4. The compounds of the invention are useful for the treatment of inflammation, and cell proliferative diseases such as cancer and restenosis.

BACKGROUND

Cyclin-dependent kinases and related serine/threonine protein kinases are important cellular enzymes that perform essential functions in regulating cell division and proliferation. The cyclin-dependent kinase catalytic units are activated by regulatory subunits known as cyclins. At least 16 mammalian cyclins have been identified (Johnson D. G. and Walker C. L., Annu. Rev. Pharmacol. Toxicol. 1999;39: 295-312). Cyclin B/cdk1, Cyclin A/cdk2, Cyclin E/cdk2, Cyclin D/cdk4, Cyclin D/Cdk6, and probably other heterodimers including Cdk3 and Cdk7 are important regulators of cell cycle progression. Additional functions of Cyclin/Cdk heterodimers include regulation of transcription, DNA repair, differentiation and apoptosis (Morgan D. O., Annu. Rev. Cell. Dev. Biol. 1997; 13261-13291).

Increased activity or temporally abnormal activation of cyclin-dependent kinases has been shown to result in the development of human tumors (Sherr C. J., Science 1996; 274:1672-1677). Indeed, human tumor development is commonly associated with alterations in either the Cdk proteins themselves or their regulators (Cordon-Cardo C., Am. J. Pathol. 1995;147:545-560; Karp J. E. and Broder S., Nat. Med. 1995;1:309-320; Hall M. et al., Adv. Cancer Res. 1996;68:67-108). Naturally occurring protein inhibitors of Cdks such as p16 and p27 cause growth inhibition in vitro in lung cancer cell lines (Kamb A., Curr. Top. Microbiol. Immunol. 1998;227:139-148).

Small molecule Cdk inhibitors may also be used in the treatment of cardiovascular disorders such as restenosis and atherosclerosis and other vascular disorders that are due to aberrant cell proliferation. Vascular smooth muscle proliferation and intimal hyperplasia following balloon angioplasty are inhibited by over-expression of the cyclin-dependent kinase inhibitor protein p21 (Chang M. W. et al., J. Clin. Invest., 1995;96:2260; Yang Z-Y. et al., Proc. Natl. Acad. Sci. (USA) 1996;93:9905. Moreover, the purine cdk2 inhibitor CVT-313 (Ki=95 nM) resulted in greater than 80% inhibition of neointima formation in rats (Brooks E. E. et al., J. Biol. Chem. 1997:29207-29211).

Cdk inhibitors can be used to treat diseases caused by a variety of infectious agents, including fungi, protozoan parasites such as Plasmodium falciparum, and DNA and RNA viruses. For example, cyclin-dependent kinases are required for viral replication following infection by herpes simplex virus (HSV) (Schang L. M. et al., J. ViroL 1998; 72:5626) and Cdk homologs are known to play essential roles in yeast.

Selective Cdk inhibitors can be used to ameliorate the effects of various autoimmune disorders. Chronic inflammatory disease rheumatoid arthritis is characterized by synovial tissue hyperplasia; inhibition of synovial tissue proliferation should minimize inflammation and prevent joint destruction. Expression of the Cdk inhibitor protein p16 in synovial fibroblasts led to growth inhibition (Taniguchi K. et al., Nat. Med. 1999;5:760-767). Similarly, in a rat model of arthritis, joint swelling was substantially inhibited by treatment with a p16 expressing adenovirus. Cdk inhibitors may be effective against other disorders of cell proliferation including psoriasis (characterized by keratinocyte hyperproliferation), glomerulonephritis, and lupus.

Certain Cdk inhibitors may be useful as chemoprotective agents through their ability to inhibit cell cycle progression of normal untransformed cells (Chen et al. J. Natl. Cancer Institute, 2000;92:1999-2008). Pre-treatment of a cancer patient with a Cdk inhibitor prior to the use of cytotoxic agents can reduce the side effects commonly associated with chemotherapy. Normal proliferating tissues are protected from the cytotoxic effects by the action of the selective Cdk inhibitor.

Review articles on small molecule inhibitors of cyclin dependent kinases have noted the difficulty of identifying compounds that inhibit specific Cdk proteins without inhibiting other enzymes. Thus, despite their potential to treat a variety of diseases, no Cdk inhibitors are currently approved for commercial use (Fischer, P. M., Curr. Opin. Drug Discovery 2001, 4, 623-634; Fry, D. W. & Garrett, M. D. Curr. Opin. Oncologic, Endocrine & Metabolic Invest 2000, 2, 40-59; Webster, K. R. & Kimball, D. Emerging Drugs 2000, 5, 45-59; Sielecki, T. M. et al. J. Med. Chem. 2000, 43, 1-18.).

SUMMARY OF THE INVENTION

This invention provides compounds of the formula I:

I

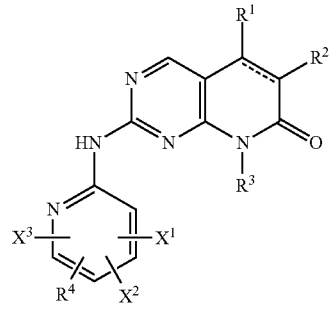

wherein:

the dashed line represents an optional bond, $X^1$, $X^2$, and $X^3$ are in each instance independently selected from hydrogen, halogen, $C_1$-$C_6$ alkyl, $C_1$-$C_6$ haloalkyl, $C_1$-$C_8$ alkoxy, $C_1$-$C_8$ alkoxyalkyl, CN, $NO_2$, $OR^5$, $NR^5R^6$, $CO_2R^6$, $COR^5$, $S(O)_nR^5$, $CONR^5R^6$, $NR^5COR^6$, $NR^5SO_2R^6$, $SO_2NR^5R^6$, and $P(O)(OR^5)(OR^6)$; with the proviso that at least one of $X^1$, $X^2$, and $X^3$ must be hydrogen;

n=0-2;

$R^1$ is, in each instance, independently, hydrogen, halogen, $C_1$-$C_6$ alkyl, $C_1$-$C_6$ haloalkyl, $C_1$-$C_6$ hydoxyalkyl, or $C_3$-$C_7$ cycloalkyl;

$R^2$ and $R^4$ are independently selected from hydrogen, halogen, $C_1$-$C_8$ alkyl, $C_3$-$C_7$ cycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^5$, $SR^5$, $NR^5R^6$, $N(O)R^5R^6$, $P(O)(OR^5)(OR^6)$, $(CR^5R^6)_mNR^7R^8$, $COR^5$, $(CR^4R^5)_mC(O)R^7$, $CO_2R^5$, $CONR^5R^6$, $C(O)NR^5SO_2R^6$, $NR^5SO_2R^6$, $C(O)NR_5OR^6$, $S(O)_nR^5$, $SO_2NR^5R^6$, $P(O)(OR^5)(OR^6)$, $(CR^5R^6)_mP(O)(OR^7)(OR^8)$, $(CR^5R^6)_m$-aryl, $(CR^5R^6)_m$-heteroaryl, $-T(CH_2)_mQR^5$, $—C(O)T(CH_2)_mQR^5$, $NR^5C(O)T(CH_2)_mQR^5$, and $—CR^5{=}CR^6C(O)R^7$; or $R^1$ and $R^2$ may form a carbocyclic group containing 3-7 ring members, preferably 5-6 ring members, up to four of which can optionally be replaced with a heteroatom independently selected from oxygen, sulfur, and nitrogen, and wherein the carbocyclic group is unsubstituted or substituted with one, two, or three groups independently selected from halogen, hydroxy, hydroxyalkyl, nitrile, lower $C_1$-$C_8$ alkyl, lower $C_1$-$C_8$ alkoxy, alkoxycarbonyl, alkylcarbonyl, alkylcarbonylamino, aminoalkyl, trifluoromethyl, N-hydroxyacetamide, trifluoromethylalkyl, amino, and mono or dialkylamino, $(CH_2)_mC(O)NR^5R^6$, and $O(CH_2)_mC(O)OR^5$, provided, however, that there is at least one carbon atom in the carbocyclic ring and that if there are two or more ring oxygen atoms, the ring oxygen atoms are not adjacent to one another;

T is O, S, $NR^7$, $N(O)R^7$, $NR^7R^8W$, or $CR^7R^8$;

Q is O, S, $NR^7$, $N(O)R^7$, $NR^7R^8W$, $CO_2$, $O(CH_2)_m$-heteroaryl, $O(CH_2)_mS(O)_nR^8$, $(CH_2)$-heteroaryl, or a carbocyclic group containing from 3-7 ring members, up to four of which ring members are optionally heteroatoms independently selected from oxygen, sulfur, and nitrogen, provided, however, that there is at least one carbon atom in the carbocyclic ring and that if there are two or more ring oxygen atoms, the ring oxygen atoms are not adjacent to one another, wherein the carbocyclic group is unsubstituted or substituted with one, two, or three groups independently selected from halogen, hydroxy, hydroxyalkyl, lower alkyl, lower alkoxy, alkoxycarbonyl, alkylcarbonyl, alkylcarbonylamino, aminoalkyl, trifluoromethyl, N-hydroxyacetamide, trifluoromethylalkyl, amino, and mono or dialkylamino;

W is an anion selected from the group consisting of chloride, bromide, trifluoroacetate, and triethylammonium;

m=0-6;

$R^4$ and one of $X^1$, $X^2$ and $X^3$ may form an aromatic ring containing up to three heteroatoms independently selected from oxygen, sulfur, and nitrogen, and optionally substituted by up to 4 groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, mono- or dialkylamino, N-hydroxyacetamido, aryl, heteroaryl, carboxyalkyl, nitrile, $NR^7SO_2R^8$, $C(O)NR^7R^8$, $NR^7C(O)R^8$, $C(O)OR^7$, $C(O)NR^7SO_2R^8$, $(CH_2)_mS(O)_nR^7$, $(CH_2)_m$-heteroaryl, $O(CH_2)_m$-heteroaryl, $(CH_2)_mC(O)N\ R^7R^8$, $O(CH_2)_mC(O)OR^7$, $(CH_2)_mSO_2NR^7R^8$, and $C(O)R^7$;

$R^3$ is hydrogen, aryl, $C_1$-$C_8$ alkyl, $C_1$-$C_8$ alkoxy, $C_3$-$C_7$ cycloalkyl, or $C_3$-$C_7$-heterocyclyl;

$R^5$ and $R^6$ independently are hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heterarylalkyl; or $R^5$ and $R^6$, when attached to the same nitrogen atom, taken together with the nitrogen to which they are attached, form a heterocyclic ring containing from 3-8 ring members, up to four of which members can optionally be replaced with heteroatoms independently selected from oxygen, sulfur, S(O), $S(O)_2$, and nitrogen, provided, however, that there is at least one carbon atom in the heterocyclic ring and that if there are two or more ring oxygen atoms, the ring oxygen atoms are not adjacent to one another, wherein the heterocyclic group is unsubstituted or substituted with one, two or three groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, nitrile, mono- or dialkylamino, aryl, heteroaryl, carboxyalkyl, $NR^7SO_2R^8$, $C(O)NR^7R^8$, $NR^7C(O)R^8$, $C(O)OR^7$, $C(O)NR^7SO_2R^8$, $(CH_2)_mS(O)_nR^7$, $(CH_2)_m$-heteroaryl, $O(CH_2)_m$-heteroaryl, $(CH_2)_mC(O)NR^7R^8$, $O(CH_2)_mC(O)OR^7$, and $(CH_2)SO_2NR^7R^8$;

$R^7$ and $R^8$ are, independently, hydrogen, $C_1$-$C_8$ alkyl, $C_2$-$C_8$ alkenyl, $C_2$-$C_8$ alkynyl,alkynyl, arylalkyl, cycloalkyl, heterocycloalkyl, aryl, heteroaryl, or heterarylalkyl; or $R^7$ and $R^8$, when attached to the same nitrogen atom, taken together with the nitrogen to which they are attached, may form a heterocyclic ring containing from 3-8 ring members, up to four of which members are optionally heteroatoms independently selected from oxygen, sulfur, S(O), $S(O)_2$, and nitrogen, provided, however, that there is at least one carbon atom in the heterocyclic ring and that if there are two or more ring oxygen atoms, the ring oxygen atoms are not adjacent to one another, wherein the heterocyclic group is unsubstituted or substituted with one, two or three groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, nitrile, mono- or dialkylamino, N-hydroxyacetamido, aryl, heteroaryl, carboxyalkyl; and the pharmaceutically acceptable salts, esters, amides, and prodrugs thereof.

This invention identifies 2-(2'-pyridyl) pyrido[2,3-d]pyrimidinones as compounds that are useful for treating uncontrolled cell proliferative diseases, including, but not limited to, proliferative diseases such as cancer, restenosis and rheumatoid arthritis. In addition, these compounds are useful for treating inflammation and inflammatory diseases. In addition, these compounds have utility as antiinfective agents. Moreover, these compounds have utility as chemoprotective agents through their ability to inhibit the cell cycle progression of normal untransformed cells. Many of the compounds of the invention display unexpected improvements in selectivity for the serine/threonine kinases cyclin-dependent kinase 4 and cyclin-dependent kinase 6. The compounds are readily synthesized and can be administered to patients by a variety of methods.

Compounds of formula I may contain chiral centers and therefore may exist in different enantiomeric and diastereomeric forms. This invention relates to all optical isomers and all stereoisomers of compounds of the formula I, both as racemic mixtures and as individual enantiomers and diastereoismers of such compounds, and mixtures thereof, and to all pharmaceutical compositions and methods of treatment defined above that contain or employ them, respectively.

As the compounds of formula I of this invention may possess at least two asymmetric centers, they are capable of occurring in various stereoisomeric forms or configurations.

Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of Formula I are capable of further forming pharmaceutically acceptable formulations comprising salts, including but not limited to acid addition and/or base salts, solvents and N-oxides of a compound of Formula I.

This invention also provides pharmaceutical formulations comprising a therapeutically effective amount of a compound of Formula I or a therapeutically acceptable salt thereof and a pharmaceutically acceptable carrier, diluent, or excipient therefor. All of these forms are within the present invention.

By "alkyl," in the present invention is meant a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, iso-pentyl, n-hexyl, and the like.

"Alkenyl" means straight and branched hydrocarbon radicals having from 2 to 8 carbon atoms and at least one double bond and includes, but is not limited to, ethenyl, 3-buten-1-yl, 2-ethenylbutyl, 3-hexen-1-yl, and the like. The term "alkenyl" includes, cycloalkenyl, and heteroalkenyl in which 1 to 3 heteroatoms selected from O, S, N or substituted nitrogen may replace carbon atoms.

"Alkynyl" means straight and branched hydrocarbon radicals having from 2 to 8 carbon atoms and at least one triple bond and includes, but is not limited to, ethynyl, 3-butyn-1-yl, propynyl, 2-butyn-1-yl, 3-pentyn-1-yl, and the like.

"Cycloalkyl" means a monocyclic or polycyclic hydrocarbyl group having from 3 to 8 carbon atoms, for instance, cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, amino, alkyl, and dialkylamino, and the like. Also included are rings in which 1 to 3 heteroatoms replace carbons. Such groups are termed "heterocyclyl," which means a cycloalkyl group also bearing at least one heteroatom selected from O, S, N or substituted nitrogen. Examples of such groups include, but are not limited to, oxiranyl, pyrrolidinyl, piperidyl, tetrahydropyran, and morpholine.

By "alkoxy," is meant straight or branched chain alkyl groups having 1-10 carbon atoms and linked through oxygen. Examples of such groups include, but are not limited to, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, and 3-methylpentoxy. In addition, alkoxy refers to polyethers such as —O—$(CH_2)_2$—O—$CH_3$, and the like.

"Acyl" means an alkyl or aryl (Ar) group having from 1-10 carbon atoms bonded through a carbonyl group, i.e., R—C(O)—. For example, acyl includes, but is not limited to, a $C_1$-$C_6$ alkanoyl, including substituted alkanoyl, wherein the alkyl portion can be substituted by $NR^4R^5$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^4R^5$, phenyl, substituted phenyl, thio $C_1$-$C_6$ alkyl, $C_1$-$C_6$ alkoxy, hydroxy, carboxy, $C_1$-$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$-$C_6$ alkyl or $(CH_2)_pPh$ where p is 1, 2, or 3. Perhalo and polyhalo substitution is also included.

Examples of substituted alkyl groups include, but are not limited to, 2-aminoethyl, 2-hydroxyethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include, but are not limited to, 2-methoxyethynyl, 2-ethylsulfanylethynyl, 4-(1-piperazinyl)-3-(butynyl), 3-phenyl-5-hexynyl, 3-diethylamino-3-butynyl, 4-chloro-3-butynyl, 4-cyclobutyl-4hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include, but are not limited to, dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The term "anion" means a negatively charged counterion such as chloride, bromide, trifluoroacetate, and triethylammonium.

By the term "halogen" in the present invention is meant fluorine, bromine, chlorine, and iodine.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, triazolyl, imidazolyl, (is)oxazolyl, oxadiazolyl, tetrazolyl, pyridyl, thiadiazolyl, oxadiazolyl, oxathiadiazolyl, thiatriazolyl, pyrimidinyl, (iso)quinolinyl, napthyridinyl, phthalimidyl, benzimidazolyl, and benzoxazolyl. A preferred heteroaryl is pyridine.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can be mono-, di-, or trisubstituted with, e.g., halogen, lower alkyl, lower alkoxy, lower alkylthio, trifluoromethyl, lower acyloxy, aryl, heteroaryl, and hydroxy. A preferred aryl is phenyl.

The term "cancer" includes, but is not limited to, the following cancers: cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. In so far as the compounds of formula I of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Salts may be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts may also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts may include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. (See, for example, Berge S. M. et al., "Pharmaceutical Salts," J. Pharm. Sci., 1977;66:1-19 which is incorporated herein by reference.)

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl.

$C_1$-$C_4$ alkyl esters are preferred. Esters of the compounds of the present invention may be prepared according to conventional methods "March's Advanced Organic Chemistry, 5th Edition". M. B. Smith & J. March, John Wiley & Sons, 2001.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods such as "March's Advanced Organic Chemistry, 5th Edition". M. B. Smith & J. March, John Wiley & Sons, 2001.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

Preferred compounds of the present invention are those having the formula II:

II

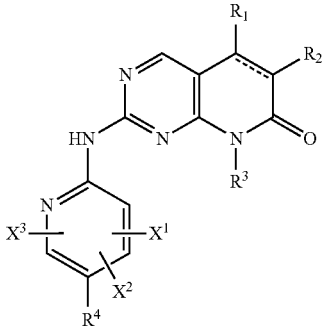

wherein $R^1$, $R^2$, $R^3$, $R^4$, $X^1$, $X^2$, and $X^3$, are as defined for formula I.

In one preferred embodiment of the present invention one of $X^1$, $X^2$ or $X^3$ is hydrogen, halogen, or alkyl.

In a further preferred embodiment of the present invention one of $X^1$, $X^2$ or $X^3$ is $OR^5$, $NR^5R^6$ or $COR^5$.

In a most preferred embodiment of the present invention $X^1{=}X^2{=}X^3{=}H$.

In another preferred embodiment of the present invention $R^1$ is hydrogen, halogen or alkyl.

In a more preferred embodiment of the present invention $R^1$ is alkyl.

In a preferred embodiment of the present invention one of $R^2$ and $R^4$ is hydrogen, halogen, $C_1$-$C_8$ alkyl, $C_1$-$C_8$ alkoxy, nitrile, $OR^5$, $NR^5R^6$, $COR^5$, $(CR^4R^5)_mC(O)R^7$, $CO_2R^6$, $CONR^5R^6$, $(CR^5R^6)_m$-aryl, or $(CR^5\ R^6)_m$-heteroaryl.

In a more preferred embodiment of the present invention $R^2$ is hydrogen, halogen, $C_1$-$C_8$ alkyl, $OR^5$, $NR^5R^6$, $COR^5$, $(CR^5R^6)_m$-aryl, or $(CR^5R^6)_m$-heteroaryl.

In a further preferred embodiment of the present invention $R^4$ is hydrogen, $OR^5$, or $NR^5R^6$.

In another preferred embodiment of the present invention $R^3$ is $C_1$-$C_8$ alkyl.

In yet another preferred embodiment of the present invention $R^5$ and $R^6$ are hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heterarylalkyl.

In a further preferred embodiment of the present invention $R^5$ and $R^6$ together with the nitrogen to which they are attached form a carbocyclic ring containing from 3-8 members, up to four of which members are heteroatoms.

In a more preferred embodiment of the present invention $R^5$ and $R^6$ together with the nitrogen to which they are attached form a carbocyclic ring containing 5 or 6 members, up to two of which members are heteroatoms.

In a most preferred embodiment of the present invention $R^5$ and $R^6$ together with the nitrogen to which they are attached form a piperazine ring.

Further preferred embodiments of the present invention are compounds according to Formula I in which $R^4$ is a disubstituted amine.

Especially preferred embodiments of the present invention are compounds according to Formula I in which $R^1$ is a methyl group and $R^3$ is a cyclopentyl group.

Preferred embodiments of the present invention include, but are not limited to, the compounds listed below:

8-Cyclopentyl-2-(pyridin-2-ylamino)-8H-pyrido[2,3-d]pyrimidin-7-one,

6-Bromo-8-cyclopentyl-2-(5-piperazin-1-yl-pyrimidin-2-ylamino)-8H-pyrido[2,3-d]pyrimidin-7-one hydrochloride, 8-Cyclopentyl-6-ethyl-2-(5-piperazin-1-yl-pyridin-2-ylamino)-8H-pyrido[2,3-d]pyrimidin-7-one hydrochloride, 8-Cyclopentyl-7-oxo-2-(5-piperazin-1-yl-pyridin-2-ylamino)-7,8-dihydro-pyrido[2,3-d]pyrimidine-6-carboxylic acid ethyl ester hydrochloride, 6-Amino-8-cyclopentyl-2-(5-piperazin-1-yl-pyridin-2-ylamino)-8H-pyrido[2,3-d]pyrimidin-7-one hydrochloride, 6-Bromo-8-cyclopentyl-2-[5-((R)-1-methy-1-pyrrolidin-2-yl)-pyridin-2-ylamino]-8H-pyrido[2,3-d]pyrimidin-7-one hydrochloride, 6-Bromo-8-cyclohexyl-2-(pyridin-2-yl-amino)-8H-pyrido[2,3-d]pyrimidin-7-one, 6-Acetyl-8-cyclopentyl-2-[5-(3,5-dimethyl-piperazin-1-yl)-pyridin-2-ylamino]-5-methyl-8H-pyrido[2,3-d]pyrimidin-7-one, 6-Acetyl-8-cyclopentyl-2-[5-(3,3-dimethyl-piperazin-1-yl)-pyridin-2-ylamino]-5-methyl-8H-pyrido[2,3-d]pyrimidin-7-one, 6-Acetyl-8-cyclopentyl-5-methyl-2-[5-(4-methyl-piperazin-1-yl)-pyridin-2-ylamino]-8H-pyrido[2,3-d]pyrimidin-7-one, 6-Acetyl-2-[5-(3-amino-pyrrolidin-1-yl)-pyridin-2-ylamino]-8-cyclopentyl-5-methyl-8H-pyrido[2,3-d]pyrimidin-7-one, 6-Bromo-8-cyclopentyl-5-methyl-2-(5-morpholin-4-yl-pyridin-2-ylamino)-8H-pyrido[2,3-d]pyrimidin-7-one, 2-{5-[Bis-(2-methoxy-ethyl)-amino]-pyridin-2-ylamino}-6-bromo-8-cyclopentyl-5-methyl-8H-pyrido[2,3-d]pyrimidin-7-one, 6-Acetyl-8-cyclopentyl-5-methyl-2-(5-morpholin-4-yl-pyridin-2-ylamino)-8H-pyrido[2,3-d]pyrimidin-7-one, 6-Acetyl-2-{5-[bis-(2-methoxy-ethyl)-amino]-pyridin-2-ylamino}-8-cyclopentyl-5-methyl-8H-pyrido[2,3-d]pyrimidin-7-one, 4-[6-(8-Cyclopentyl-6-iodo-5-methyl-7-oxo-7,8-dihydro-pyrido[2,3-d]pyrimidin-2-ylamino)-pyridin-3-yl]-piperazine-1-carboxylic acid tert-butyl ester, 8-Cyclopentyl-6-iodo-5-methyl-2-(5-piperazin-1-yl-pyridin-2-ylamino)-8H-pyrido[2,3-d]pyrimidin-7-one, 4-{6-[8-Cyclopentyl-6-(2-ethoxy-ethoxy)-7-oxo-7,8-dihydro-pyrido[2,3-d]pyrimidin-2-ylamino]-pyridin-3-yl}-piperazine-1-carboxylic acid tert-butyl ester, 8-Cyclopentyl-6-(2-ethoxy-ethoxy)-2-(5-piperazin-1-yl-pyridin-2-ylamino)-8H-pyrido[2,3-d]pyrimidin-7-one, 2-{5-[Bis-(2-methoxy-ethyl)-amino]-pyridin-2-ylamino}-6-bromo-8-cyclopentyl-5-methyl-8H-pyrido[2,3-d]pyrimidin-7-one, 6-Acetyl-2-{5-[bis-(2-methoxy-ethyl)-amino]-pyridin-2-ylamino}-8-cyclopentyl-5-methyl-8H-pyrido[2,3-d]pyrimidin-7-one, 4-[6-(8-isopropyl-7-oxo-7,8-dihydro-pyrido[2,3-d]pyrimidin-2-ylamino)-pyridin-3-yl]-piperazine-1-carboxylic acid tert-butyl ester, 8-isopropyl-2-(5-piperazin-1-yl-pyridin-2-ylamino)-8H-pyrido[2,3-d]pyrimidin-7-one, 4-[6-(8-cyclopentyl-7-oxo-7,8-dihydro-pyrido[2,3-d]pyrimidin-2-ylamino)-pyridin-3-yl]-piperazine-1-carboxylic acid tert-butyl ester, 8-cyclopentyl-2-(5-piperazin-1-yl-pyridin-2-ylamino)-8H-pyrido[2,3-d]pyrimidin-7-one, 4-[6-(8-cyclohexyl-7-oxo-7,8-dihydro-pyrido[2,3-d]pyrimidin-2-ylamino)-pyridin-3-yl]-piperazine-1-carboxylic acid tert-butyl ester, 8-cyclohexyl-2-(5-piperazin-1-yl-pyridin-2-ylamino)-8H-pyrido[2,3-d]pyrimidin-7-one, 4-[6-(8-cyclopropyl-7-oxo-7,8-dihydro-pyrido[2,3-d]pyrimidin-2-ylamino)-pyridin-3-yl]-piperazine-1-carboxylic acid tert-butyl ester, 8-cyclopropyl-2-(5-piperazin-1-yl-pyridin-2-ylamino)-8H-pyrido[2,3-d]pyrimidin-7-one, 6-Bromo-8-cyclopentyl-2-(pyridin-2,6-yldiamino)-8H-pyrido[2,3-d]pyrimidin-7-one, 6-Bromo-8-cyclopentyl-5-methyl-2-(pyridin-2-ylamino)-8H-pyrido[2,3-d]pyrimidin-7-one, 6-Bromo-8-cyclopentyl-5-methyl-2-[5-(4-methyl-piperazin-1-yl)-pyridin-2-ylamino]-8H-pyrido[2,3-d]pyrimidin-7-one, 8-Cyclopentyl-6-(1-ethoxy-vinyl)-5-methyl-2-[5-(4-methyl-piperazin-1-yl)-pyridin-2-ylamino]-8H-pyrido[2,3-d]pyrimidin-7-one, (1-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-pyrrolidin-3-yl)-carbamic acid tert-butyl ester, 6-Acetyl-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one, 4-[6-(6-Bromo-8-cyclopentyl-5-methyl-7-oxo-7,8-dihydro-pyrido[2,3-d]pyrimidin-2-ylamino)-pyridin-3-yl]-azepane-1-carboxylic acid tert-butyl ester, 6-Bromo-8-cyclopentyl-2-(5-[1,4]diazepan-1-yl-pyridin-2-ylamino)-5-methyl-8H-pyrido[2,3-d]pyrimidin-7-one, 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-[1,4]diazepane-1-carboxylic acid tert-butyl ester, 6-Acetyl-8-cyclopentyl-2-(5-[1,4]diazepan-1-yl-pyridin-2-ylamino)-5-methyl-8H-pyrido[2,3-d]pyrimidin-7-one, 6-Acetyl-8-cyclopentyl-5-methyl-2-(pyridin-2-ylamino)-8H-pyrido[2,3-d]pyriminin-7-one, 4-[6-(8-Cyclopentyl-5-methyl-7-oxo-7,8-dihydro-pyrido[2,3-d]pyrimidin-2-ylamino)-pyridin-3-yl]-piperazine-1-carboxylic acid tert-butyl ester, 8-Cyclopentyl-5-methyl-2-(5-piperazin-4-yl-pyridin-2-ylamino)-8H-pyrido[2,3-d]pyrimidin-7-one, 4-[6-(6-Bromo-8-cyclopentyl-5-methyl-7-oxo-7,8-dihydro-pyrido[2,3-d]pyrimidin-2-ylamino)-pyridin-3-yl]-2,2-dimethyl-piperazine-1-carboxylic acid tert-butyl ester, 6-Bromo-8-cyclopentyl-2-[5-(3,3-dimethyl-piperazin-1-yl)-pyridin-2-ylamino]-5-methyl-8H-pyrido[2,3d]pyrimidin-7-one, 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,2-dimethyl-piperazine-1-carboxylic acid tert-butyl ester, 4-[6-(6-Bromo-8-cyclopentyl-5-methyl-7-oxo-7,8-dihydro-pyrido[2,3-d]pyrimidin-2-ylamino)-pyridin-3-yl]-2,6-dimethyl-piperazine-1-carboxylic acid tert-butyl ester, 6-Bromo-8-cyclopentyl-2-[5-(3,5-dimethyl-piperazin-1-yl)-pyridin-2-ylamino]-5-methyl-8H-pyrido[2,3-d]pyrimidin-7-one, 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,6-dimethyl-piperazine-1-carboxylic acid tert-butyl ester, 8-Cyclopentyl-6-(1-ethoxy-vinyl)-5-methyl-2-(5-morpholin-4-yl-pyridin-2-ylamino)-8H-pyrido[2,3-d]pyrimidin-7-one, 6-Bromo-8-cyclopentyl-5-methyl-2-(3,4,5,6-tetrahydro-2H-[1,3']bipyridinyl-6'-ylamino)-8H-pyrido[2,3-d]pyrimidin-7-one, 8-Cyclopentyl-6-(1-ethoxy-vinyl)-5-methyl-2-(3,4,5,6-tetrahydro-2H-[1,3']bipyridinyl-ylamino)-8H-pyrido[2,3-d]pyrimidin-7-one, 6-Acetyl-8-cyclopentyl-5-methyl-2-(3,4,5,6-tetrahydro-2H-[1,3']bipyridinyl-6'-ylamino)-8H-pyrido[2,3-d]pyrimidin-7-one, 4-{6-[8-Cyclopentyl-6-(2-ethoxy-ethyl)-7-oxo-7,8-dihydro-pyrido[2,3-d]pyrimidin-2-ylamino]-pyridin-3-yl}-piperazine-1-carboxylic acid tert-butyl ester, 8-Cyclopentyl-6-(2-ethoxy-ethyl)-2-(5-piperazin-1-yl-pyridin-2-ylamino)-8H-pyrido[2,3-d]pyrimidin-7-one, 4-{6-[8-Cyclopentyl-6-(2-methoxy-ethoxymethyl)-7-oxo-7,8-dihydro-pyrido[2,3-d]pyrimidin-2-ylamino]-pyridin-3-yl}-piperazine-1-carboxylic acid tert-butyl ester, 8-Cyclopentyl-6-(2-methoxy-ethoxymethyl)-2-(5-piperazin-1-yl-pyridin-2-ylamino)-8H-pyrido[2,3-d]pyrimidin-7-one, 4-[6-(8-Cyclopentyl-6-ethoxymethyl-7-oxo-7,8-dihydro-pyrido[2,3-d]pyrimidin-2-ylamino)-pyridin-3-yl]-piperazine-1-carboxylic acid tert-butyl ester, 8-Cyclopentyl-6-ethoxymethyl-2-(5-piperazin-1-yl-pyridin-2-ylamino)-8H-pyrido[2,3-d]pyrimidin-7-one, 4-[6-(8-Cyclopentyl-6-methoxymethyl-7-oxo-7,8-dihydro-pyrido[2,3-d]pyrimidin-2-ylamino)-pyridin-3-yl]-piperazine-1-carboxylic acid tert-butyl ester, 8-Cyclopentyl-6-methoxymethyl-2-(5-piperazin-1-yl-pyridin-2-ylamino)-8H-pyrido[2,3-d]pyrimidin-7-one, 6-Bromo-8-cyclopentyl-2-[5-(2,6-dimethyl-morpholin-4-yl)-pyridin-2-ylamino]-5-methyl-8H-pyrido[2,3-d]pyrimidin-7-one, 8-Cyclopentyl-6-ethoxymethyl-2-(3,4,5,6-tetrahydro-2H-[1,3']bipyridinyl-6'-ylamino)-8H-pyrido[2,3-d]pyrimidin-7-one, 8-Cyclopentyl-6-ethoxymethyl-2-(5-morpholin-4-yl-pyridin-2-ylamino)-8H-pyrido[2,3-d]pyrimidin-7-one,

[8-Cyclopentyl-7-oxo-2-(3,4,5,6-tetrahydro-2H-[1,3']bipyridinyl-6'-ylamino)-7,8-dihydro-pyrido[2,3-d]pyrimidin-6-ylmethyl]-carbamic acid benzyl ester, 8-Cyclopentyl-2-[5-(2,6-dimethyl-morpholin-4-yl)-pyridin-2-ylamino]-6-(1-ethoxy-vinyl)-5-methyl-8H-pyrido[2,3-d]pyrimidin-7-one, 6-Acetyl-8-cyclopentyl-2-[5-(2,6-dimethyl-morpholin-4-yl)-pyridin-2-ylamino]-5-methyl-8H-pyrido[2,3-d]pyrimidin-7-one, 8-Cyclopentyl-5-methyl-2-(5-piperazin-1-yl-pyridin-2-ylamino)-6-propionyl-8H-pyrido[2,3-d]pyrimidin-7-one.

Other embodiments of the present invention include, but are not limited to the compounds listed below:

6-Bromo-8-cyclopentyl-2-methyl-8H-pyrido[2,3-d]pyrimidin-7-one,

6-Bromo-8-cyclopentyl-5-methyl-2-(5-piperizin-1-yl-pyridin-2-ylamino)-8H-pyrido[2,3-d]pyrimidin-7-one, 8-Cyclopentyl-6-fluoro-2-(5-piperazin-1-yl-pyridin-2-ylamino)-8H-pyrido[2,3-d]pyrimidin-7-one hydrochloride, 8-Cyclopentyl-6-methyl-2-(5-piperazin-1-yl-pyridin-2-ylamino)-8H-pyrido[2,3-d]pyrimidin-7-one hydrochloride, 8-Cyclopentyl-6-isobutoxy-2-(5-piperazin-1-yl-pyridin-2-ylamino)-8H-pyrido[2,3-d]pyrimidin-7-one hydrochloride, 6-Benzyl-8-cyclopentyl-2-(5-piperazin-1-yl-pyridin-2-ylamino)-8H-pyrido[2,3-d]pyrimidin-7-one hydrochloride, 8-Cyclopentyl-6-hydroxymethyl-2-(5-piperazin-1-yl-pyridin-2-ylamino)-8H-pyrido[2,3-d]pyrimidin-7-one hydrochloride, 2-[5-(4-tert-Butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester, 6-Acetyl-8-cyclopentyl-2-(5-piperazin-1-yl-pyridin-2-ylamino)-8H-pyrido[2,3-d]pyrimidin-7-one, 6-Acetyl-8-cyclopentyl-5-methyl-2-(5-piperazin-1-yl-pyridin-2-ylamino)-8H-pyrido[2,3-d]pyrimidin-7-one, 6-Bromo-8-cyclopentyl-5-methyl-2-(pyridin-2-ylamino)-8H-pyrido[2,3-d]pyrimidin-7-one, 6-Bromo-8-cyclopentyl-2-(pyridin-2-ylamino)-8H-pyrido[2,3-d]pyrimidin-7-one, 6-Bromo-8-cyclopentyl-2-[5-(3,5-dimethyl-piperazin-1-yl)-pyridin-2-ylamino]-8H-pyrido[2,3-d]pyrimidin-7-one, 6-Bromo-8-cyclopentyl-2-[5-(3,3-dimethyl-piperazin-1-yl)-pyridin-2-ylamino]-8H-pyrido[2,3-d]pyrimidin-7-one, 6-Bromo-8-cyclopentyl-2-[5-(4-methyl-piperazin-1-yl)-pyridin-2-ylamino]-8H-pyrido[2,3-d]pyrimidin-7-one, 2-[5-(3-Amino-pyrrolidin-1-yl)-pyridin-2-ylamino]-6-bromo-8-cyclopentyl-8H-pyrido[2,3-d]pyrimidin-7-one, 6-Bromo-8-cyclopentyl-2-[5-(3-ethylamino-pyrrolidin-1-yl)-pyridin-2-ylamino]-8H-pyrido[2,3-d]pyrimidin-7-one, 6-Bromo-8-cyclopentyl-2-(5-pyrrolidin-1-yl-pyridin-2-ylamino)-8H-pyrido[2,3-d]pyrimidin-7-one, 2-{5-[3-(1-Amino-1-methyl-ethyl)-pyrrolidin-1-yl]-pyridin-2-ylamino}-6-bromo-8-cyclopentyl-8H-pyrido[2,3-d]pyrimidin-7-one, 1-[6-(6-Bromo-8-cyclopentyl-7-oxo-7,8-dihydro-pyrido[2,3-d]pyrimidin-2-ylamino)-pyridin-3-yl]-pyrrolidine-2-carboxylic acid, 6-Bromo-8-cyclopentyl-2-[5-(4-diethylamino-butylamino)-pyridin-2-ylamino]-8H-pyrido[2,3-d]pyrimidin-7-one, 6-Acetyl-8-cyclopentyl-2-[5-(3-ethylamino-pyrrolidin-1-yl)-pyridin-2-ylamino]-5-methyl-8H-pyrido[2,3-d]pyrimidin-7-one, 6-Acetyl-8-cyclopentyl-5-methyl-2-(5-pyrrolidin-1-yl-pyridin-2-ylamino)-8H-pyrido[2,3-d]pyrimidin-7-one, 6-Acetyl-2-{5-[3-(1-amino-1-methyl-ethyl)-pyrrolidin-1-yl]-pyridin-2-ylamino}-8-cyclopentyl-5-methyl-8H-pyrido[2,3-d]pyrimidin-7-one, 1-[6-(6-Acetyl-8-cyclopentyl-5-methyl-7-oxo-7,8-dihydro-pyrido[2,3-d]pyrimidin-2-ylamino)-pyridin-3-yl]-pyrrolidine-2-carboxylic acid, 6-Acetyl-8-cyclopentyl-2-[5-(4-diethylamino-butylamino)-pyridin2-ylamino]-5-methyl-8H-pyrido[2,3-d]pyrimidin-7-one, 8-Cyclopentyl-2-[5-(3,5-dimethyl-piperazin-1-yl)-pyridin-2-ylamino]-6-ethyl-8H-pyrido[2,3-d]pyrimidin-7-one, 8-Cyclopentyl-2-[5-(3,3-dimethyl-piperazin-1-yl)-pyridin-2-ylamino]-6-ethyl-8H-pyrido[2,3-d]pyrimidin-7-one, 8-Cyclopentyl-6-ethyl-2-[5-(4-methyl-piperazin-1-yl)-pyridin-2-ylamino]-8H-pyrido[2,3-d]pyrimidin-7-one, 2-[5-(3-Amino-pyrrolidin-1-yl)-pyridin-2-ylamino]-8-cyclopentyl-6-ethyl-8H-pyrido[2,3-d]pyrimidin-7-one, 8-Cyclopentyl-6-ethyl-2-[5-(3-ethylamino-pyrrolidin-1-yl)-pyridin-2-ylamino]-8H-pyrido[2,3-d]pyrimidin-7-one, 8-Cyclopentyl-6-ethyl-2-(5-pyrrolidin-1-yl-pyridin-2-ylamino)-8H-pyrido[2,3-d]pyrimidin-7-one, 2-{5-[3-(1-Amino-1-methyl-ethyl)-pyrrolidin-1-yl]-pyridin-2-ylamino}-8-cyclopentyl-6-ethyl-8H-pyrido[2,3-d]pyrimidin-7-one, 1-[6-(8-Cyclopentyl-6-ethyl-7-oxo-7,8-dihydro-pyrido[2,3-d]pyrimidin-2-ylamino)-pyridin-3-yl]-pyrrolidine-2-carboxylic acid, 8-Cyclopentyl-2-[5-(4-diethylamino-butylamino)-pyridin-2-ylamino]-6-ethyl-8H-pyrido[2,3-d]pyrimidin-7-one, 6-Benzyl-8-cyclopentyl-2-[5-(3,5-dimethyl-piperazin-1-yl)-pyridin-2-ylamino]-8H-pyrido[2,3-d]pyrimidin-7-one, 6-Benzyl-8-cyclopentyl-2-[5-(3,3-dimethyl-piperazin-1-yl)-pyridin-2-ylamino]-8H-pyrido[2,3-d]pyrimidin-7-one, 6-Benzyl-8-cyclopentyl-2-[5-(4-methyl-piperazin-1-yl)-pyridin-2-ylamino]-8H-pyrido[2,3d]pyrimidin-7-one, 2-[5-(3-Amino-pyrrolidin-1-yl)-pyridin-2-ylamino]-6-benzyl-8-cyclopentyl-8H-pyrido[2,3-d]pyrimidin-7-one, 6-Benzyl-8-cyclopentyl-2-[5-(3-ethylamino-pyrrolidin-1-yl)-pyridin-2-ylamino]-8H-pyrido[2,3-d]pyrimidin-7-one, 6-Benzyl-8-cyclopentyl-2-(5-pyrrolidin-1-yl-pyridin-2-ylamino)-8H-pyrido[2,3-d]pyrimidin-7-one, 2-{5-[3-(1-Amino-1-methyl-ethyl)-pyrrolidin-1-yl]-pyridin-2-ylamino}-6-benzyl-8-cyclopentyl-8H-pyrido[2,3-d]pyrimidin-7-one, 1-[6-(6-Benzyl-8-cyclopentyl-7-oxo-7,8-dihydro-pyrido[2,3-d]pyrimidin-2-ylamino)-pyridin-3-yl]-pyrrolidine-2-carboxylic acid, 6-Benzyl-8-cyclopentyl-2-[5-(4-diethylamino-butylamino)-pyridin-2-ylamino]-8H-pyrido[2,3-d]pyrimidin-7-one, 8-Cyclopentyl-2-[5-(3,5-dimethyl-piperazin-1-yl)-pyridin-2-ylamino]-6-hydroxymethyl-8H-pyrido[2,3-d]pyrimidin-7-one, 8-Cyclopentyl-2-[5-(3,3-dimethyl-piperazin-1-yl)-pyridin-2-ylamino]-6-hydroxymethyl-8H-pyrido[2,3-d]pyrimidin-7-one, 8-Cyclopentyl-6-hydroxymethyl-2-[5-(4-methyl-piperazin-1-yl)-pyridin-2-ylamino]-8H-pyrido[2,3-d]pyrimidin-7-one, 2-[5-(3-Amino-pyrrolidin-1-yl)-pyridin-2-ylamino]-8-cyclopentyl-6-hydroxymethyl-8H-pyrido[2,3-d]pyrimidin-7-one, 8-Cyclopentyl-2-[5-(3-ethylamino-pyrrolidin-1-yl)-pyridin-2-ylamino]-6-hydroxymethyl-8H-pyrido[2,3-d]pyrimidin-7-one, 8-Cyclopentyl-6-hydroxymethyl-2-(5-pyrrolidin-1-yl-pyridin-2-ylamino)-8H-pyrido[2,3-d]pyrimidin-7-one, 2-{5-[3-(1-Amino-1-methyl-ethyl)-pyrrolidin-1-yl]-pyridin-2-ylamino}-8-cyclopentyl-6-hydroxymethyl-8H-pyrido[2,3-d]pyrimidin-7-one, 1-[6-(8-Cyclopentyl-6-hydroxymethyl-7-oxo-7,8-dihydro-pyrido[2,3-d]pyrimidin-2-ylamino)-pyridin-3-yl]-pyrrolidine-2-carboxylic acid, 8-Cyclopentyl-2-[5-(4-diethylamino-butylamino)-pyridin-2-ylamino]-6-hydroxymethyl-8H-pyrido[2,3-d]pyrimidin-7-one, 6-Amino-8-cyclopentyl-2-[5-(3,5-dimethyl-piperazin-1-yl)-pyridin-2-ylamino]-8H-pyrido[2,3-d]pyrimidin-7-one, 6-Amino-8-cyclopentyl-2-[5-(3,3-dimethyl-piperazin-1-yl)-pyridin-2-ylamino]-8H-pyrido[2,3-d]pyrimidin-7-one, 6-Amino-8-cyclopentyl-2-[5-(4-methyl-piperazin-1-yl)-pyridin-2-ylamino]-8H-pyrido[2,3d]pyrimidin-7-one, 6-Amino-2-[5-(3-amino-pyrrolidin-1-yl)-pyridin-2-ylamino]-8-cyclopentyl-8H-pyrido[2,3-d]pyrimidin-7-one, 6-Amino-8-cyclopentyl-2-[5-(3-ethylamino-pyrrolidin-1-yl)-pyridin-2-ylamino]-8H-pyrido[2,3-d]pyrimidin-7-one, 6-Amino-8-cyclopentyl-2-(5-pyrrolidin-1-yl-pyridin-2-ylamino)-8H-pyrido[2,3-d]pyrimidin-7-one, 6-Amino-2-{5-[3-(1-amino-1-methyl-ethyl)-pyrrolidin-1-yl]-pyridin-2-ylamino}-8-cyclopentyl-8H-pyrido[2,3-d]pyrimidin-7-one, 1-[6-(6-Amino-8-cyclopentyl-7-oxo-7,8-dihydro-pyrido[2,3-d]pyrimidin-2-ylamino)-pyridin-3-yl]-pyrrolidine-2-carboxylic acid, 6-Amino-8-cyclopentyl-2-[5-(4-diethylamino-butylamino)-pyridin-2-ylamino]-8H-pyrido[2,3-d]pyrimidin-7-one, 6-Bromo-8-cyclopentyl-2-(3,4,5,6-tetrahydro-2H-[1,3']bipyridinyl-6'-ylamino)-8H-pyrido[2,3-d]pyrimidin-7-one, 6-Bromo-8-cyclopentyl-2-(5-morpholin-4-yl-pyridin-2-ylamino)-8H-pyrido[2,3-d]pyrimidin-7-one, 6-Bromo-8-cyclopentyl-2-(5-diethylamino-pyridin-2-ylamino)-8H-pyrido[2,3-d]pyrimidin-7-one, 2-{5-[Bis-(2-hydroxy-ethyl)-amino]-pyridin-2-ylamino}-6-bromo-8-cyclopentyl-8H-pyrido[2,3-d]pyrimidin-7-one, 2-{5-[Bis-(2-methoxy-ethyl)-amino]-pyridin-2-ylamino}-6-bromo-8-cyclopentyl-8H-pyrido[2,3-d]pyrimidin-7-one, 2-[5-(2-Amino-ethylamino)-pyridin-2-ylamino]-6-bromo-8-cyclopentyl-8H-pyrido[2,3-d]pyrimidin-7-one, 6-Bromo-8-cyclopentyl-2-(5-dimethylamino-pyridin-2-ylamino)-8H-pyrido[2,3-d]pyrimidin-7-one, N-[6-(6-Bromo-8-cyclopentyl-7-oxo-7,8-dihydro-pyrido[2,3-d]pyrimidin-2-ylamino)-pyridin-3-yl]-N-methyl-acetamide, 6-Bromo-8-cyclopentyl-2-[5-(2-methoxy-ethoxy)-pyridin-2-ylamino]-8H-pyrido[2,3-d]pyrimidin-7-one, 6-Bromo-8-cyclopentyl-2-[5-(2-methoxy-ethoxymethyl)-pyridin-2-ylamino]-8H-pyrido[2,3-d]pyrimidin-7-one, 6-Bromo-8-cyclopentyl-2-[5-(2-diethylamino-ethoxy)-pyridin-2-ylamino]-8H-pyrido[2,3-d]pyrimidin-7-one, 6-Bromo-8-cyclopentyl-2-(5-pyrrolidin-1-yl-pyridin-2-ylamino)-8H-pyrido[2,3-d]pyrimidin-7-one, 6-Bromo-8-cyclopentyl-2-(6-methyl-5-piperazin-1-yl-pyridin-2-ylamino)-8H-pyrido[2,3-d]pyrimidin-7-one, 6-Bromo-8-cyclopentyl-5-methyl-2-(3,4,5,6-tetrahydro-2H-[1,3']bipyridinyl-6'-ylamino)-8H-pyrido[2,3-d]pyrimidin-7-one, 6-Bromo-8-cyclopentyl-2-(5-diethylamino-pyridin-2-ylamino)-5-methyl-8H-pyrido[2,3-d]pyrimidin-7-one, 2-{5-[Bis-(2-hydroxy-ethyl)-amino]-pyridin-2-ylamino}-6-bromo-8-cyclopentyl-5-methyl-8H-pyrido[2,3-d]pyrimidin-7-one, 2-[5-(2-Amino-ethylamino)-pyridin-2-ylamino]-6-bromo-8-cyclopentyl-5-methyl-8H-pyrido[2,3-d]pyrimidin-7-one, 6-Bromo-8-cyclopentyl-2-(5-dimethylamino-pyridin-2-ylamino)-5-methyl-8H-pyrido[2,3-d]pyrimidin-7-one, N-[6-(6-Bromo-8-cyclopentyl-5-methyl-7-oxo-7,8-dihydro-pyrido[2,3-d]pyrimidin-2-ylamino)-pyridin-3-yl]-N-methyl-acetamide, 6-Bromo-8-cyclopentyl-2-[5-(2-methoxy-ethoxy)-pyridin-2-ylamino]-5-methyl-8H-pyrido[2,3-d]pyrimidin-7-one, 6-Bromo-8-cyclopentyl-2-[5-(2-methoxy-ethoxymethyl)-pyridin-2-ylamino]-5-methyl-8H-pyrido[2,3-d]pyrimidin-7-one, 6-Bromo-8-cyclopentyl-2-[5-(2-diethylamino-ethoxy)-pyridin-2-ylamino]-5-methyl-8H-pyrido[2,3-d]pyrimidin-7-one, 6-Bromo-8-cyclopentyl-5-methyl-2-(5-pyrrolidin-1-yl-pyridin-2-ylamino)-8H-pyrido[2,3-d]pyrimidin-7-one, 6-Bromo-8-cyclopentyl-5-methyl-2-(6-methyl-5-piperazin-1-yl-pyridin-2-ylamino)-8H-pyrido[2,3-d]pyrimidin-7-one, 6-Acetyl-8-cyclopentyl-5-methyl-2-(3,4,5,6-tetrahydro-2H-[1,3']bipyridinyl-6'-ylamino)-8H-pyrido[2,3-d]pyrimidin-7-one, 6-Acetyl-8-cyclopentyl-2-(5-diethylamino-pyridin-2-ylamino)-5-methyl-8H-pyrido[2,3-d]pyrimidin-7-one, 6-Acetyl-2-{5-[bis-(2-hydroxy-ethyl)-amino]-pyridin-2-ylamino}-8-cyclopentyl-5-methyl-8H-pyrido[2,3-d]pyrimidin-7-one, 6-Acetyl-2-[5-(2-amino-ethylamino)-pyridin-2-ylamino]-8-cyclopentyl-5-methyl-8H-pyrido[2,3-d]pyrimidin-7-one, 6-Acetyl-8-cyclopentyl-2-(5-dimethylamino-pyridin-2-ylamino)-5-methyl-8H-pyrido[2,3-d]pyrimidin-7-one, N-[6-(6-Acetyl-8-cyclopentyl-5-methyl-7-oxo-7,8-dihydro-pyrido[2,3-d]pyrimidin-2-ylamino)-pyridin-3-yl]-N-methyl-acetamide, 6-Acetyl-8-cyclopentyl-2-[5-(2-methoxy-ethoxy)-pyridin-2-ylamino]-5-methyl-8H-pyrido[2,3-d]pyrimidin-7-one, 6-Acetyl-8-cyclopentyl-2-[5-(2-methoxy-ethoxymethyl)-pyridin-2-ylamino]-5-methyl-8H-pyrido[2,3-d]pyrimidin-7-one, 6-Acetyl-8-cyclopentyl-2-[5-(2-diethylamino-ethoxy)-pyridin-2-ylamino]-5-methyl-8H-pyrido[2,3-d]pyrimidin-7-one, 6-Acetyl-8-cyclopentyl-5-methyl-2-(5-pyrrolidin-1-yl-pyridin-2-ylamino)-8H-pyrido[2,3-d]pyrimidin-7-one, 6-Acetyl-8-cyclopentyl-5-methyl-2-(6-methyl-5-piperazin-1-yl-pyridin-2-ylamino)-8H-pyrido[2,3-d]pyrimidin-7-one, 6-Acetyl-8-cyclopentyl-2-(3,4,5,6-tetrahydro-2H-[1,3']bipyridinyl-6'-ylamino)-8H-pyrido[2,3-d]pyrimidin-7-one, 6-Acetyl-8-cyclopentyl-2-(5-morpholin-4-yl-pyridin-2-ylamino)-8H-pyrido[2,3-d]pyrimidin-7-one, 6-Acetyl-8-cyclopentyl-2-(5-diethylamino-pyridin-2-ylamino)-8H-pyrido[2,3-d]pyrimidin-7-one, 6-Acetyl-2-{5-[bis-(2-hydroxy-ethyl)-amino]-pyridin-2-ylamino}-8-cyclopentyl-8H-pyrido[2,3-d]pyrimidin-7-one, 6-Acetyl-2-{5-[bis-(2-methoxy-ethyl)-amino]-pyridin-2-ylamino}-8-cyclopentyl-8H-pyrido[2,3-d]pyrimidin-7-one, 6-Acetyl-2-[5-(2-amino-ethylamino)-pyridin-2-ylamino]-8-cyclopentyl-8H-pyrido[2,3-d]pyrimidin-7-one, 6-Acetyl-8-cyclopentyl-2-(5-dimethylamino-pyridin-2-ylamino)-8H-pyrido[2,3-d]pyrimidin-7-one, N-[6-(6-Acetyl-8-cyclopentyl-7-oxo-7,8-dihydro-pyrido[2,3-d]pyrimidin-2-ylamino)-pyridin-3-yl]-N-methyl-acetamide, 6-Acetyl-8-cyclopentyl-2-[5-(2-methoxy-ethoxy)-pyridin-2-ylamino]-8H-pyrido[2,3-d]pyrimidin-7-one, 6-Acetyl-8-cyclopentyl-2-[5-(2-methoxy-ethoxymethyl)-pyridin-2-ylamino]-8H-pyrido[2,3-d]pyrimidin-7-one, 6-Acetyl-8-cyclopentyl-2-[5-(2-diethylamino-ethoxy)-pyridin-2-ylamino)-8H-pyrido[2,3-d]pyrimidin-7-one, 6-Acetyl-8-cyclopentyl-2-(5-pyrrolidin-1-yl-pyridin-2-ylamino)-8H-pyrido[2,3-d]pyrimidin-7-one, 6-Acetyl-8-cyclopentyl-2-(6-methyl-5-piperazin-1-yl-pyridin-2-ylamino)-8H-pyrido[2,3-d]pyrimidin-7-one, 6-Bromo-8-cyclopentyl-2-[5-(2-methoxy-ethoxy)-pyridin-2-ylamino]-8H-pyrido[2,3d]pyrimidin-7-one, 6-Bromo-8-cyclopentyl-2-[5-(2-methoxy-ethylamino)-pyridin-2-ylamino]-8H-pyrido[2,3-d]pyrimidin-7-one, 2-(5-Azetidin-1-yl-pyridin-2-ylamino)-6-bromo-8-cyclopentyl-8H-pyrido[2,3-d]pyrimidin-7-one, 2-(5-Azepan-1-yl-pyridin-2-ylamino)-6-bromo-8-cyclopentyl-8H-pyrido[2,3-d]pyrimidin-7-one, N-[6-(6-Bromo-8-cyclopentyl-7-oxo-7,8-dihydro-pyrido[2,3-d]pyrimidin-2-ylamino)-pyridin-3-yl]-acetamide, 6-Bromo-8-cyclopentyl-2-(5-phenylamino-pyridin-2-ylamino)-8H-pyrido[2,3-d]pyrimidin-7-one, 6-Bromo-8-cyclopentyl-2-[5-(4-fluoro-benzylamino)-pyridin-2-ylamino]-8H-pyrido[2,3-d]pyrimidin-7-one, N-[6-(6-Bromo-8-cyclopentyl-7-oxo-7,8-dihydro-pyrido[2,3-d]pyrimidin-2-ylamino)-pyridin-3-yl]-methanesulfonamide, 6-Bromo-8-cyclopentyl-2-(5-methanesulfonyl-pyridin-2-ylamino)-8H-pyrido[2,3-d]pyrimidin-7-one, 6-Bromo-8-cyclopentyl-2-(5-phenyl-pyridin-2-ylamino)-8H-pyrido[2,3-d]pyrimidin-7-one, 6-Amino-8-cyclopentyl-2-[5-(2-methoxy-ethoxy)-pyridin-2-ylamino]-8H-pyrido[2,3-d]pyrimidin-7-one, 6-Amino-8-cyclopentyl-2-[5-(2-methoxy-ethylamino)-pyridin-2-ylamino]-8H-pyrido[2,3-d]pyrimidin-7-one, 6-Amino-2-(5-azetidin-1-yl-pyridin-2-ylamino)-8-cyclopentyl-8H-pyrido[2,3-d]pyrimidin-7-one, 6-Amino-2-(5-azepan-1-yl-pyridin-2-ylamino)-8-cyclopentyl-8H-pyrido[2,3-d]pyrimidin-7-one, N-[6-(6-Amino-8-cyclopentyl-7-oxo-7,8-dihydro-pyrido[2,3-d]pyrimidin-2-ylamino)-pyridin-3-yl]-acetamide, 6-Amino-8-cyclopentyl-2-(5-phenylamino-pyridin-2-ylamino)-8H-pyrido[2,3-d]pyrimidin-7-one, 6-Amino-8-cyclopentyl-2-[5-(4-fluoro-benzylamino)-pyridin-2-ylamino]-8H-pyrido[2,3-d]pyrimidin-7-one, N-[6-(6-Amino-8-cyclopentyl-7-oxo-7,8-dihydro-pyrido[2,3-d]pyrimidin-2-ylamino)-pyridin-3-yl]-methanesulfonamide, 6-Amino-8-cyclopentyl-2-(5-methanesulfonyl-pyridin-2-ylamino)-8H-pyrido[2,3-d]pyrimidin-7-one, 6-Amino-8-cyclopentyl-2-(5-phenyl-pyridin-2-ylamino)-8H-pyrido[2,3-d]pyrimidin-7-one, 6-Acetyl-8-cyclopentyl-2-[5-(2-methoxy-ethoxy)-pyridin-2-ylamino]-5-methyl-8H-pyrido[2,3-d]pyrimidin-7-one, 6-Acetyl-8-cyclopentyl-2-[5-(2-methoxy-ethylamino)-pyridin-2-ylamino]-5-methyl-8H-pyrido[2,3-d]pyrimidin-7-one, 6-Acetyl-2-(5-azetidin-1-yl-pyridin-2-ylamino)-8-cyclopentyl-5-methyl-8H-pyrido[2,3-d]pyrimidin-7-one, 6-Acetyl-2-(5-azepan-1-yl-pyridin-2-ylamino)-8-cyclopentyl-5-methyl-8H-pyrido[2,3-d]pyrimidin-7-one, N-[6-(6-Acetyl-8-cyclopentyl-5-methyl-7-oxo-7,8-dihydro-pyrido[2,3-d]pyrimidin-2-ylamino)-pyridin-3-yl]-acetamide, 6-Acetyl-8-cyclopentyl-5-methyl-2-(5-phenylamino-pyridin-2-ylamino)-8H-pyrido(2,3-d]pyrimidin-7-one, 6-Acetyl-8-cyclopentyl-2-[5-(4-fluoro-benzylamino)-pyridin-2-ylamino]-5-methyl-8H-pyrido[2,3-d]pyrimidin-7-one, N-[6-(6-Acetyl-8-cyclopentyl-5-methyl-7-oxo-7,8-dihydro-pyrido[2,3-d]pyrimidin-2-ylamino)-pyridin-3-yl]-methanesulfonamide, 6-Acetyl-8-cyclopentyl-2-(5-methanesulfonyl-pyridin-2-ylamino)-5-methyl-8H-pyrido[2,3-d]pyrimidin-7-one, 6-Acetyl-8-cyclopentyl-5-methyl-2-(5-phenyl-pyridin-2-ylamino)-8H-pyrido[2,3-d]pyrimidin-7-one, 6-Benzyl-8-cyclopentyl-2-[5-(2-methoxy-ethoxy)-pyridin-2-ylamino]-8H-pyrido[2,3-d]pyrimidin-7-one, 6-Benzyl-8-cyclopentyl-2-[5-(2-methoxy-ethylamino)-pyridin-2-ylamino]-8H-pyrido[2,3-d]pyrimidin-7-one, 2-(5-Azetidin-1-y-pyridin-2-ylamino)-6-benzyl-8-cyclopentyl-8H-pyrido[2,3-d]pyrimidin-7-one, 2-(5-Azepan-1-yl-pyridin-2-ylamino)-6-benzyl-8-cyclopentyl-8H-pyrido[2,3-d]pyrimidin-7-one, N-[6-(6-Benzyl-8-cyclopentyl-7-oxo-7,8-dihydro-pyrido[2,3-d]pyrimidin-2-ylamino)-pyridin-3-yl]-acetamide, 6-Benzyl-8-cyclopentyl-2-(5-phenylamino-pyridin-2-ylamino)-8H-pyrido[2,3-d]pyrimidin-7-one, 6-Benzyl-8-cyclopentyl-2-[5-(4-fluoro-benzylamino)-pyridin-2-ylamino]-8H-pyrido[2,3-d]pyrimidin-7-one, N-[6-(6-Benzyl-8-cyclopentyl-7-oxo-7,8-dihydro-pyrido[2,3-d]pyrimidin-2-ylamino)-pyridin-3-yl]-methanesulfonamide, 6-Benzyl-8-cyclopentyl-2-(5-methanesulfonyl-pyridin-2-ylamino)-8H-pyrido[2,3-d]pyrimidin-7-one, 6-Benzyl-8-cyclopentyl-2-(5-phenyl-pyridin-2-ylamino)-8H-pyrido[2,3-d]pyrimidin-7-one, 8-Cyclopentyl-6-hydroxymethyl-2-[5-(2-methoxy-ethoxy)-pyridin-2-ylamino]-8H-pyrido[2,3-d]pyrimidin-7-one, 8-Cyclopentyl-6-hydroxymethyl-2-[5-(2-methoxy-ethylamino)-pyridin-2-ylamino]-8H-pyrido[2,3-d]pyrimidin-7-one, 2-(5-Azetidin-1-y-pyridin-2-ylamino)-8-cyclopentyl-6-hydroxymethyl-8H-pyrido[2,3-d]pyrimidin-7-one, 2-(5-Azepan-1-yl-pyridin-2-ylamino)-8-cyclopentyl-6-hydroxymethyl-8H-pyrido[2,3-d]pyrimidin-7-one, N-[6-(8-Cyclopentyl-6-hydroxymethyl-7-oxo-7,8-dihydro-pyrido[2,3-d]pyrimidin-2-ylamino)-pyridin-3-yl]-acetamide, 8-Cyclopentyl-6-hydroxymethyl-2-(5-phenylamino-pyridin-2-ylamino)-8H-pyrido[2,3-d]pyrimidin-7-one, 8-Cyclopentyl-2-[5-(4-fluoro-benzylamino)-pyridin-2-ylamino]-6-hydroxymethyl-8H-pyrido[2,3-d]pyrimidin-7-one, N-[6-(8-Cyclopentyl-6-hydroxymethyl-7-oxo-7,8-dihydro-pyrido[2,3-d]pyrimidin-2-ylamino)-pyridin-3-yl]-methanesulfonamide, 8-Cyclopentyl-6-hydroxymethyl-2-(5-methanesulfonyl-pyridin-2-ylamino)-8H-pyrido[2,3-d]pyrimidin-7-one, 8-Cyclopentyl-6-hydroxymethyl-2-(5-phenyl-pyridin-2-ylamino)-8H-pyrido[2,3-d]pyrimidin-7-one, 8-Cyclopentyl-6-ethyl-2-[5-(2-methoxy-ethoxy)-pyridin-2-ylamino]-8H-pyrido[2,3-d]pyrimidin-7-one, 8-Cyclopentyl-6-ethyl-2-[5-(2-methoxy-ethylamino)-pyridin-2-ylamino]-8H-pyrido[2,3-d]pyrimidin-7-one, 2-(5-Azetidin-1-yl-pyridin-2-ylamino)-8-cyclopentyl-6-ethyl-8H-pyrido[2,3-d]pyrimidin-7-one, 2-(5-Azepan-1-yl-pyridin-2-ylamino)-8-cyclopentyl-6-ethyl-8H-pyrido[2,3-d]pyrimidin-7-one, N-[6-(8-Cyclopentyl-6-ethyl-7-oxo-7,8-dihydro-pyrido[2,3-d]pyrimidin-2-ylamino)-pyridin-3-yl]-acetamide, 8-Cyclopentyl-6-ethyl-2-(5-phenylamino-pyridin-2-ylamino)-8H-pyrido[2,3-d]pyrimidin-7-one, 8-Cyclopentyl-6-ethyl-2-[5-(4-fluoro-benzylamino)-pyridin-2-ylamino]-8H-pyrido[2,3-d]pyrimidin-7-one, N-[6-(8-Cyclopentyl-6-ethyl-7-oxo-7,8-dihydro-pyrido[2,3-d]pyrimidin-2-ylamino)-pyridin-3-yl]-methanesulfonamide, 8-Cyclopentyl-6-ethyl-2-(5-methanesulfonyl-pyridin-2-ylamino)-8H-pyrido[2,3-d]pyrimidin-7-one, 8-Cyclopentyl-6-ethyl-2-(5-phenyl-pyridin-2-ylamino)-8H-pyrido[2,3-d]pyrimidin-7-one, 6-Bromo-8-cyclopentyl-2-[5-(piperazine-1-carbonyl)-pyridin-2-ylamino]-8H-pyrido[2,3-d]pyrimidin-7-one, 6-Bromo-8-cyclopentyl-2-[5-(3,5-dimethyl-piperazine-1-carbonyl)-pyridin-2-ylamino]-8H-pyrido[2,3-d]pyrimidin-7-one, 2-[5-(3-Amino-pyrrolidine-1-carbonyl)-pyridin-2-ylamino]-6-bromo-8-cyclopentyl-8H-pyrido[2,3-d]pyrimidin-7-one, 6-Bromo-8-cyclopentyl-2-[5-(morpholine-4-carbonyl)-pyridin-2-ylamino]-8H-pyrido[2,3-d]pyrimidin-7-one, 6-Bromo-8-cyclopentyl-5-methyl-2-[5-(piperazine-1-carbonyl)-pyridin-2-ylamino]-8H-pyrido[2,3-d]pyrimidin-7-one, 6-Bromo-8-cyclopentyl-2-[5-(3,5-dimethyl-piperazine-1-carbonyl)-pyridin-2-ylamino]-5-methyl-8H-pyrido[2,3-d]pyrimidin-7-one, 2-[5-(3-Amino-pyrrolidine-1-carbonyl)-pyridin-2-ylamino]-6-bromo-8-cyclopentyl-5-methyl-8H-pyrido[2,3-d]pyrimidin-7-one, 6-Bromo-8-cyclopentyl-5-methyl-2-[5-(morpholine-4-carbonyl)-pyridin-2-ylamino]-8H-pyrido[2,3-d]pyrimidin-7-one, 6-Acetyl-8-cyclopentyl-5-methyl-2-[5-(piperazine-1-carbonyl)-pyridin-2-ylamino]-8H-pyrido[2,3-d]pyrimidin-7-one, 6-Acetyl-8-cyclopentyl-2-[5-(3,5-dimethyl-piperazine-1-carbonyl)-pyridin-2-ylamino]-5-methyl-8H-pyrido[2,3-d]pyrimidin-7-one, 6-Acetyl-2-[5-(3-amino-pyrrolidine-1-carbonyl)-pyridin-2-ylamino]-8-cyclopentyl-5-methyl-8H-pyrido[2,3-d]pyrimidin-7-one, 6-Acetyl-8-cyclopentyl-5-methyl-2-[5-(morpholine-4-carbonyl)-pyridin-2-ylamino]-8H-pyrido[2,3-d]pyrimidin-7-one, 8-Cyclopentyl-6-ethyl-2-[5-(piperazine-1-carbonyl)-pyridin-2-ylamino]-8H-pyrido[2,3-d]pyrimidin-7-one, 8-Cyclopentyl-2-[5-(3,5-dimethyl-piperazine-1-carbonyl)-pyridin-2-ylamino]-6-ethyl-8H-pyrido[2,3-d]pyrimidin-7-one, 2-[5-(3-Amino-pyrrolidine-1-carbonyl)-pyridin-2-ylamino]-8-cyclopentyl-6-ethyl-8H-pyrido[2,3-d]pyrimidin-7-one, 8-Cyclopentyl-6-ethyl-2-[5-(morpholine-4-carbonyl)-pyridin-2-ylamino]-8H-pyrido[2,3-d]pyrimidin-7-one, 6-Bromo-8-cyclopentyl-2-[5-(piperazine-1-sulfonyl)-pyridin-2-ylamino]-8H-pyrido[2,3-d]pyrimidin-7-one, 6-Bromo-8-cyclopentyl-2-[5-(morpholine-4-sulfonyl)-pyridin-2-ylamino]-8H-pyrido[2,3-d]pyrimidin-7-one, 2-[5-(3-Amino-pyrrolidine-1-sulfonyl)-pyridin-2-ylamino]-6-bromo-8-cyclopentyl-8H-pyrido[2,3-d]pyrimidin-7-one, 6-Bromo-8-cyclopentyl-2-[5-(3,5-dimethyl-piperazine-1-sulfonyl)-pyridin-2-ylamino]-8H-pyrido[2,3-d]pyrimidin-7-one, 8-Cyclopentyl-6-ethyl-2-[5-(piperazine-1-sulfonyl)-pyridin-2-ylamino]-8H-pyrido[2,3-d]pyrimidin-7-one, 8-Cyclopentyl-6-ethyl-2-[5-(morpholine-4-sulfonyl)-pyridin-2-ylamino]-8H-pyrido[2,3-d]pyrimidin-7-one, 2-[5-(3-Amino-pyrrolidine-1-sulfonyl)-pyridin-2-ylamino]-8-cyclopentyl-6-ethyl-8H-pyrido[2,3-d]pyrimidin-7-one, 8-Cyclopentyl-2-[5-(3,5-dimethyl-piperazine-1-sulfonyl)-pyridin-2-ylamino]-6-ethyl-8H-pyrido[2,3-d]pyrimidin-7-one, 6-Acetyl-8-cyclopentyl-5-methyl-2-[5-(piperazine-1-sulfonyl)-pyridin-2-ylamino]-8H-pyrido[2,3-d]pyrimidin-7-one, 6-Acetyl-8-cyclopentyl-5-methyl-2-[5-(morpholine-4-sulfonyl)-pyridin-2-ylamino]-8H-pyrido[2,3-d]pyrimidin-7-one, 6-Acetyl-2-[5-(3-amino-pyrrolidine-1-sulfonyl)-pyridin-2-ylamino]-8-cyclopentyl-5-methyl-8H-pyrido[2,3-d]pyrimidin-7-one, 6-Acetyl-8-cyclopentyl-2-[5-(3,5-dimethyl-piperazine-1-sulfonyl)-pyridin-2-ylamino]-5-methyl-8H-pyrido[2,3-d]pyrimidin-7-one, and 6-Acetyl-8-cyclopentyl-5-methyl-2-([1,6]naphthyridin-2-ylamino)-8H-pyrido[2,3-d]pyrimidin-7-one, 6-Acetyl-8-cyclopentyl-2-[5-(1,1-dioxo-116-thiomorpholin-4-yl)-pyridin-2-ylamino]-5-methyl-8H-pyrido[2,3-d]pyrimidin-7-one, 8-Cyclopentyl-6-hydroxymethyl-5-methyl-2-(5-piperazin-1-yl-pyridin-2-ylamino)-8H-pyrido[2,3-d]pyrimidin-7-one, 6-Acetyl-2-(3-chloro-5-piperazin-1-yl-pyridin-2-ylamino)-8-cyclopentyl-5-methyl-8H-pyrido[2,3-d]pyrimidin-7-one, 4-[6-Acetyl-5-methyl-7-oxo-2-(pyridin-2-ylamino)-7H-pyrido[2,3-d]pyrimidin-8-yl]-cyclohexanecarboxylic acid, 4-[6-Acetyl-2-(5-dimethylamino-pyridin-2-ylamino)-5-methyl-7-oxo-7H-pyrido[2,3-d]pyrimidin-8-yl]-cyclohexanecarboxylic acid, 6-Bromo-8-cyclopentyl-5-methyl-2-[5-(piperazine-1-sulfonyl)-pyridin-2-ylamino]-8H-pyrido[2,3-d]pyrimidin-7-one, 6-(8-Cyclopentyl-6-ethyl-7-oxo-7,8-dihydro-pyrido[2,3-d]pyrimidin-2-ylamino)-3-piperazin-1-yl-pyridine-2-carboxylic acid, 2-(6-Acetyl-5-piperazin-1-yl-pyridin-2-ylamino)-8-cyclopentyl-6-ethyl-8H-pyrido[2,3-d]pyrimidin-7-one, 3-{2-[6-(8-Cyclopentyl-6-ethyl-7-oxo-7,8-dihydro-pyrido[2,3-d]pyrimidin-2-ylamino)-pyridin-3-yloxy]-ethoxy}-propionic acid,

[6-(8-Cyclopentyl-6-ethyl-7-oxo-7,8-dihydro-pyrido[2,3-d]pyrimidin-2-ylamino)-pyridin-3-yloxy]-acetic acid, 8-Cyclopentyl-2-(5-{2-[2-(5-methyl-pyridin-2-yl)-ethoxy]-ethoxy}-pyridin-2-ylamino)-8H-pyrido[2,3-d]pyrimidin-7-one, 2-[5-(3-Benzenesulfonyl-propoxy)-pyridin-2-ylamino]-8-cyclopentyl-8H-pyrido[2,3-d]pyrimidin-7-one, 8-Cyclopentyl-6-ethyl-2-{5-[2-(2-methoxy-ethoxy)-ethoxy]-pyridin-2-ylamino}-8H-pyrido[2,3-d]pyrimidin-7-one, 8-Cyclopentyl-2-(5-{[3-(3,5-dimethyl-piperazin-1-yl)-propyl)-methyl-amino}-pyridin-2-ylamino)-8H-pyrido[2,3-d]pyrimidin-7-one, 8-Cyclopentyl-2-{5-[(3-imidazol-1-yl-propyl)-methyl-amino]-pyridin-2-ylamino}-8H-pyrido[2,3-d]pyrimidin-7-one, 6-Acetyl-5-methyl-2-(5-methyl-pyridin-2-ylamino)-8-piperidin-4-yl-8H-pyrido[2,3-d]pyrimidin-7-one, 6-Acetyl-2-[5-(3,4-dihydroxy-pyrrolidin-1-yl)-pyridin-2-ylamino]-8-methoxymethyl-5-methyl-8H-pyrido[2,3-d] pyrimidin-7-one.

This invention provides a method of treating a disorder or condition selected from the group consisting of cell proliferative disorders, such as cancer, vascular smooth muscle proliferation associated with atherosclerosis, postsurgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease, in a mammal, including human, comprising administering to said mammal an amount of a compound of formula I, or a pharmaceutically acceptable salt thereof, that is effective in treating such disorder or condition This invention further provides compounds of formula I that are useful for treating abnormal cell proliferation such a cancer. The invention provides a method of o treating the abnormal cell proliferation disorders such as a cancer selected from the group consisting of cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia, comprising administering a therapeutically effective amound of a compound of formula I, or a pharmaceutically acceptable salt thereof, to a subject in need of such treatment.

A further embodiment of this invention is a method of treating subjects suffering from diseases caused by vascular smooth muscle cell proliferation. Compounds within the scope of the present invention effectively inhibit vascular smooth muscle cell proliferation and migration. The method comprises administering to a subject in need of treatment an amount of a compound of formula I, or a pharmaceutically acceptable salt thereof, sufficient to inhibit vascular smooth muscle proliferation, and/or migration.

This invention further provides a method of treating a subject suffering from gout comprising administering to said subject in need of treatment an amount of a compound of formula I, or a pharmaceutically acceptable salt thereof, sufficient to treat the condition.

This invention further provides a method of treating a subject suffering from kidney disease, such as polycystic kidney disease, comprising administering to said subject in need of treatment an amount of a compound of formula I, or a pharmaceutically acceptable salt thereof, sufficient to treat the condition.

Because of their inhibitory activity against cdks and other kinases, the compounds of the present invention are also useful research tools for studying the mechanism of action of those kinases, both in vitro and in vivo.

The above-identified methods of treatment are preferably carried out by administering a therapeutically effective amount of a compound of Formula I (set forth below) to a subject in need of treatment. Compounds of the present invention are substituted 2-aminopyridines that are potent inhibitors of cyclin-dependent kinases 4 (cdk4). The compounds are readily synthesized and can be administered by a variety of routes, including orally and parenterally, and have little or no toxicity. The compounds of the invention are members of the class of compounds of Formula I.

This invention provides a pharmaceutical composition comprising a therapeutically effective amount of a compound of the formula I, or a pharmaceutically acceptable salt thereof, and a pharmaceutically acceptable carrier, diluent, or excipient therefor.

Many of the compounds of the present invention are selective inhibitors of cyclin dependent kinase cdk4, which is to say that they inhibit cdk4 more potently than they inhibit tyrosine kinases and other serine-threonine kinases including other cyclin-dependent kinases such as cdk2. Despite their selectivity for cdk4 inhibition, compounds of the invention may inhibit other kinases, albeit at higher concentrations than those at which they inhibit cdk4. However, compounds of the present invention also may inhibit Cdk6 at similar concentrations to those necessary for inhibition of dk4 since Cdk6 is structurally similar to and performs similar functions to cdk4.

Preferred embodiments of the present invention are compounds of the formula I inhibit cdk4 at least about 100-fold more potently than they inhibit cdk2.

A preferred embodiment of the present invention provides a method of inhibiting cdk4 at a lower dose than is necessary to inhibit cdk2 comprising administration of a preferred compound of formula I in an amount that selectively inhibits cdk4 over cdk2.

The compounds of formula I of this invention have useful pharmaceutical and medicinal properties. Many of the compounds of formula I of this invention exhibit significant selective cdk4 inhibitory activity and therefore are of value in the treatment of a wide variety of clinical conditions in which cdk4 kinase is abnormally elevated, or activated or present in normal amounts and activities, but where inhibition of the cdks is desirable to treat a cellular proliferative disorder. Such disorders include, but are not limited to those enumerated in the paragraphs below.

The compounds of the present invention are useful for treating cancer (for example, leukemia and cancer of the lung, breast, prostate, and skin such as melanoma) and other proliferative diseases including but not limited to psoriasis, HSV, HIV, restenosis, and atherosclerosis. To utilize a compound of the present invention to treat cancer, a patient in need of such treatment, such as one having cancer or another proliferative disease, is administered a therapeutically effective amount of a pharmaceutically acceptable composition comprising at least one compound of the present invention.

Compounds of the present invention are selective inhibitors of cdk4, which is to say that they inhibit cdk4 more potently than they inhibit tyrosine kinases and other serine-threonine kinases including other cyclin-dependent kinases such as cdk2. Despite their selectivity for cdk4 inhibition, compounds of the invention may inhibit other kinases, albeit at higher concentrations than those at which they inhibit cdk4. However, compounds of the present invention also may inhibit cdk6 at similar concentrations to those necessary for inhibition of cdk4 since cdk6 is structurally similar to and performs similar functions to cdk4.

DETAILED DESCRIPTION OF THE INVENTION

An illustration of the preparation of compounds of the present invention is shown in Schemes 1 to 13.

Synthesis

The compounds of the invention may be prepared according to the general Scheme 1. The assembly of components A and B generally requires their combination in a suitable solvent such as DMSO, toluene or pyridine, and heating of this mixture to 80-140° C. A subsequent deprotection step may be required depending on the nature of substituent $R^4$.

Scheme 1

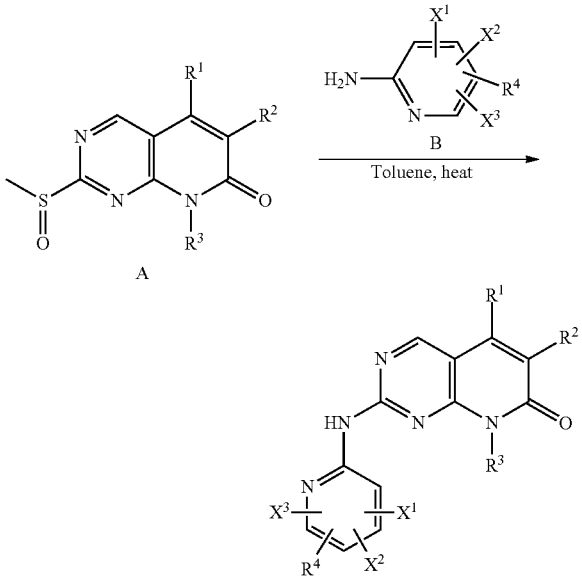

Synthesis of the sulfoxides represented by the structure A has been described previously in PCT applications WO 98/33798 and WO 01/70741. Such intermediates are assembled via established and published protocols (Barvian et al., J. Med. Chem. 2000, 43, 4606-4616) starting from the commercially available pyrimidine, 4-chloro-2-methylsulfanyl-pyrimidine-5-carboxylic acid ethyl ester. The pyridine derivatives B where $X^1$=$X^2$=$X^3$=hydrogen can be prepared from commercially available 5-bromo-2-nitropyridine by base or palladium promoted displacement of the bromine by a nucleophile such as an alcohol or a primary or secondary amine, followed by reduction of the nitro group. A representative example of this method is illustrated in Scheme 2. Examples of bases that may be used for this reaction include $K_2CO_3$, or $Na_2CO_3$. These bases may be used in the presence of a phase transfer catalyst such as $Bu_4NI$. Palladium promoted reactions are typically performed with catalysts such as $Pd(OAc)_2$, $Pd_2(dba)_3$, or $Pd(PPh_3)_4$ and the like in nonpolar organic solvents such benzene, toluene, tetrahydrofuran or acetonitrile at temperatures from 25-110° C. These catalysts are typically employed with a suitable ligand such as suitable ligand, such as BINAP, Xantphos or a related phosphine-based Pd ligand. Reduction of the nitro group is typically performed using Raney Nickel although other reducing agents also may be used including palladium on charcoal or Fe/HCl.

Scheme 2

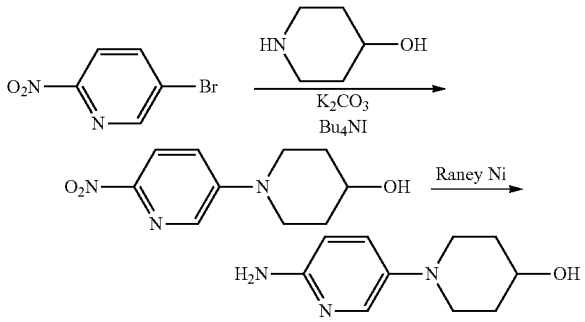

When at least one of $X^1$, $X^2$, or $X^3$ is not hydrogen, the pyridine derivatives B are prepared by methods known to those in the art. Examples of representative procedures may be found in Comprehensive Heterocyclic Chemistry, Eds. A. R. Katritzky, C. W. Rees, 1984, Pergamon, NY; Volume 2, Chapter 2.08, Pyridines and their Benzoderivatives: Synthesis, Gurnos Jones. Also, refer to Comprehensive Heterocyclic Chemistry II, Eds. A. R. Katritzky, C. W. Rees., E. Scriven, 1996, Pergamon, N.Y.; Volume 25, Chapter 5.05, Pyridines and their Benzoderivatives: Synthesis, Gurnos Jones. Representative examples are illustrated in Scheme 3.

Scheme 3

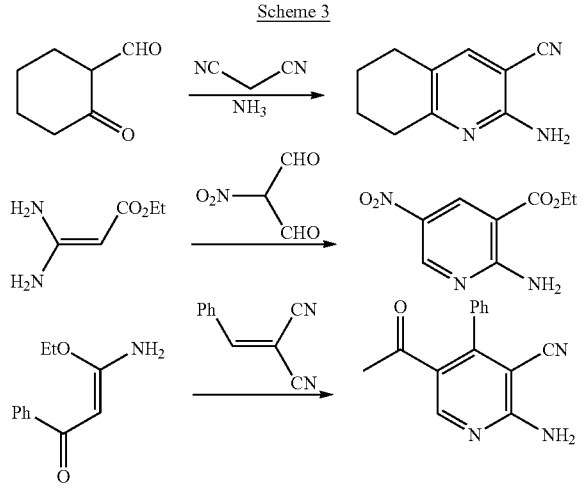

An alternate route to access compounds of the present invention involves conversion of the pyridopyrimidine core fragment to a pyridopyrimidine C-2 amine as shown in Scheme 4 and employment of this amine as a nucleophile to displace a leaving group such as bromide or iodide from a pyridine fragment. This reaction proceeds with palladium catalysis to provide the target compounds in equivalent yields to the route shown in Scheme 1. Examples of palladium catalysts that may be employed in this reaction include $Pd(OAc)_2$, $Pd_2(dba)_3$, or $Pd(PPh_3)_4$, and $PdCl_2(PPh_3)_2$.

These catalysts are typically employed with a suitable ligand, such as BINAP, Xantphos or a related phosphine-based Pd ligand. Typical solvents include dimethoxyethane, tetrahydrofuran, acetonitrile and toluene. Reactions are typically performed at temperatures between 25° C. and 160° C. In some cases, the reaction is accelerated by the presence of electron withdrawing substituents ortho to the leaving group on the pyridine ring (Jonckers, T. H. M. et al. Tetrahedron 2001, 57, 7027-7034).

Scheme 4

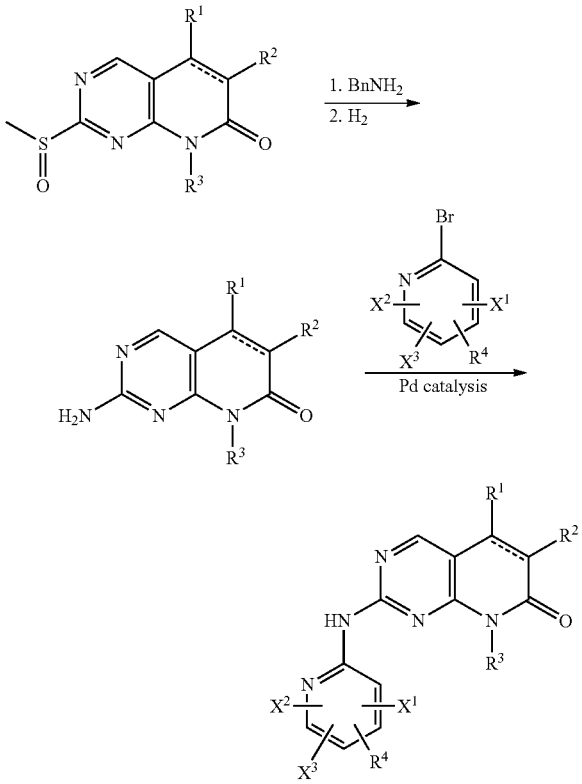

In another alternate route to compounds of the present invention, the pyridine fragment is converted to a guanidine and condensed with an appropriate partner to produce the pyrimidine ring via a condensation reaction (Scheme 5). This condensation reaction typically requires heating the reaction components at concentrations of 0.5 M to 2 M in a suitable non-polar organic solvent such as chlorobenzene, nitrobenzene, or Dowtherm to a temperature in the range of 100-200° C.

Scheme 5

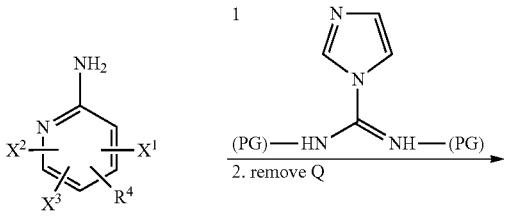

-continued

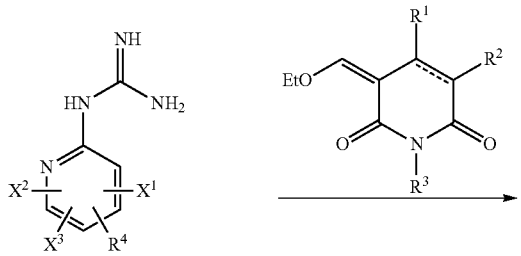

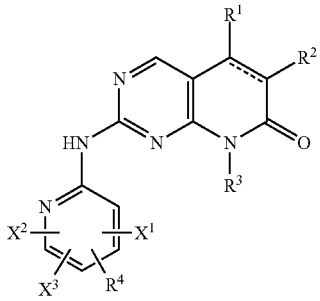

(PG) is a protecting group such as Cbz, or Boc.

In addition, synthesis of compounds of the instant invention may proceed through substituted pyrimidine intermediates such as those shown in Schemes 6-13. Thus, in Scheme 6, a 4-amino, 5-halo-pyrimidine sulfide is converted directly to a pyridopyrimidinone using chemistry introduced by Piers (e.g. Piers, E. McEachern, E. J. and Romero, M. A. J. Org. Chem. 1997, 62, 6034-6040). Alternatively, the side-chain pyridyl-amine is installed through displacement of a sulfoxide at the C2 position using standard procedures (see above), and then the pyridopyrimidinone is built-up via a Stille coupling and a ring closure reaction. Similar chemistry is employed is Schemes 7 starting with a 2-chloropyrimidine. The Stille reactions in Schemes 6 and 7 are typically performed under palladium catalysis using reagents such as $Pd(OAc)_2$, $Pd_2(dba)_3$, or $Pd(PPh_3)_4$, and $PdCl_2(PPh_3)_2$. Typical solvents include dimethoxyethane, tetrahydrofuran, acetonitrile and toluene which may be warmed during the reaction to temperatures in the range of 100-200° C. Ring closure occurs spontaneously or with gentle warming in a suitable organic solvent to a temperature less than 100° C. Installation of the C2 side chain in Scheme 7 typically proceeds with catalysis by POPd, $Pd(OAc)_2$ or $Pd_2dba_3$ and a suitable ligand, such as BINAP, Xantphos or a related phosphine-based Pd ligand.

Scheme 6

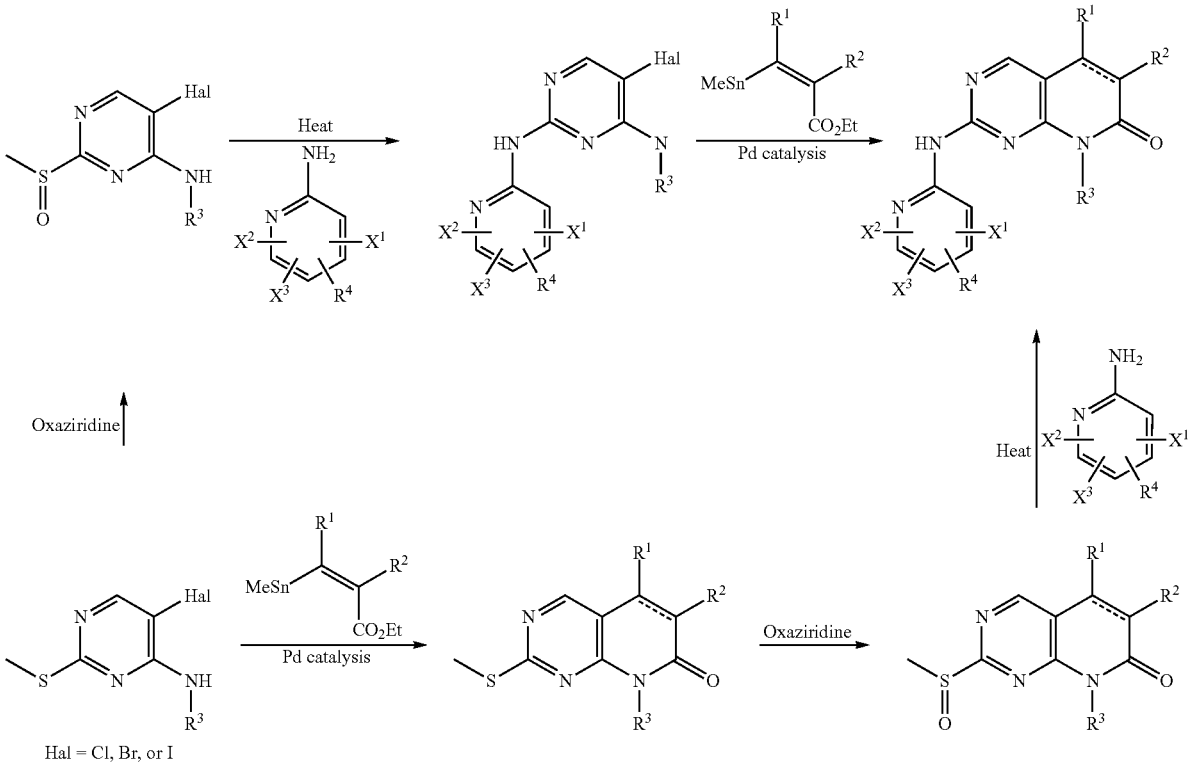

Scheme 7

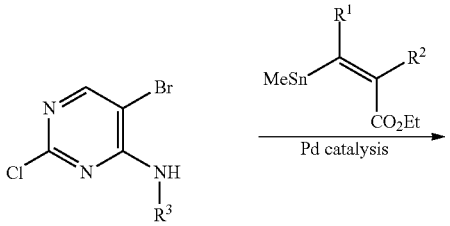

-continued

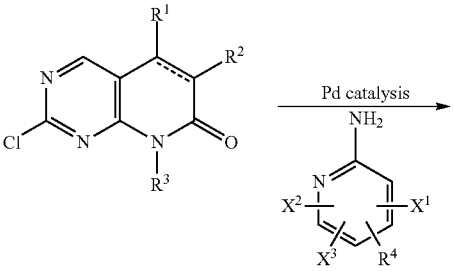

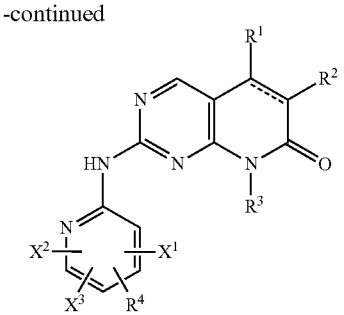

Another way to build the pyridone ring is to start with an aldehyde or ketone at the C5 position of a simple substituted 4-aminopyrimidine and to perform Wittig, Homer-Wadsworth Emmons, Knoevenagel or related chemistry such as enloate anion chemistry to install the C4-C5 double bond of the pyridopyrimidinone system. These reactions proceed under conditions that would be well known to one skilled in the art, with the employment of a suitable base such as NaH, NaOEt, LDA, BuLi, HMDS and the like. Ring closure typically occurs spontaneously under the reaction conditions when the double bond geometry is such that the pyrimidine and the ester are placed in a cis relationship across the newly formed double bond. Otherwise gentle warming in a suitable organic solvent to a temperature less than 100° C. may be required to promote ring closure. When the double bond geometry is such that the pyrimidine and the ester are placed in a trans relationship across the double bond, ring closure can be driven by double bond isomerization, for example by heating in DBU to a temperature between 100 and 200° C., or by treatment with a radical source such as iodine and UV light under conditions that would be well known to one skilled in the art. The order of ring formation and side chain installation may be reversed as shown in Schemes 11-13.
Scheme 8
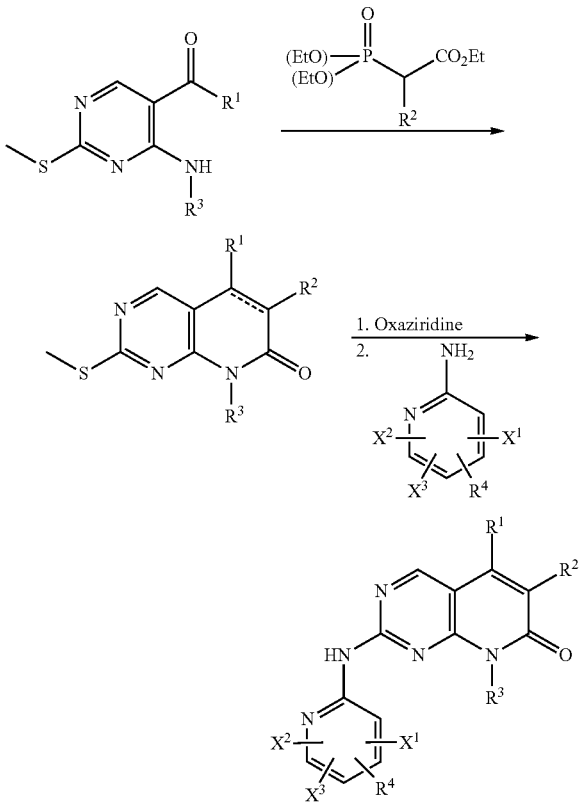
Scheme 9
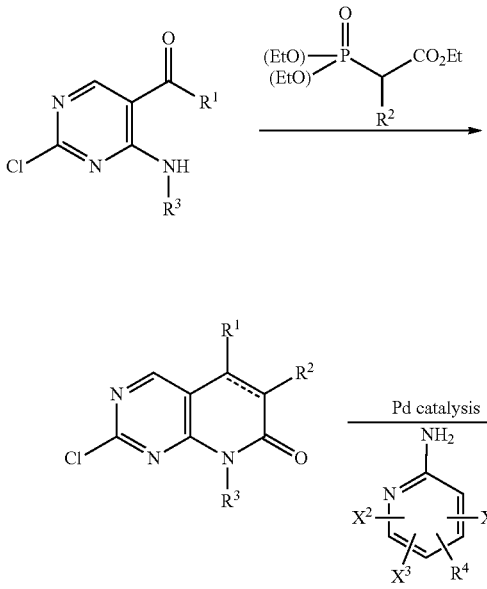
-continued
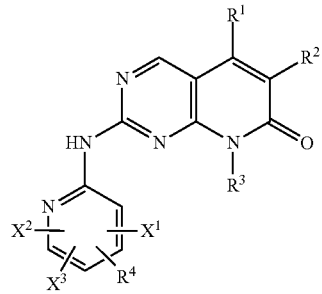
Scheme 10
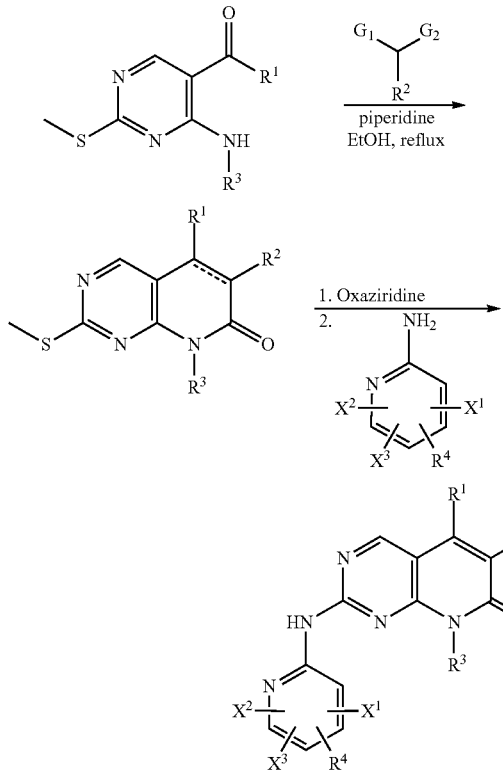
$G_1$ and $G_2$ are electron withdrawing functional groups such as CN, $CO_2Et$, $CO_2Me$,
Scheme 11
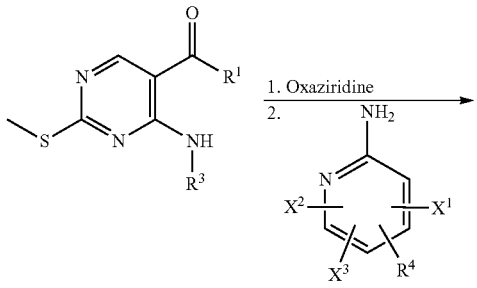

-continued

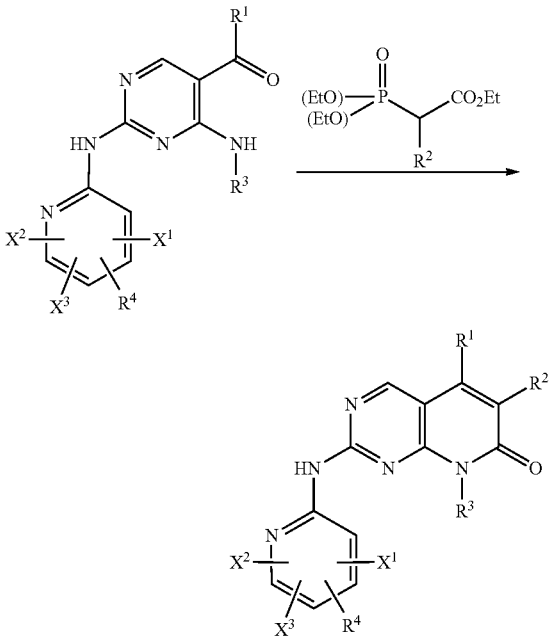

Scheme 12

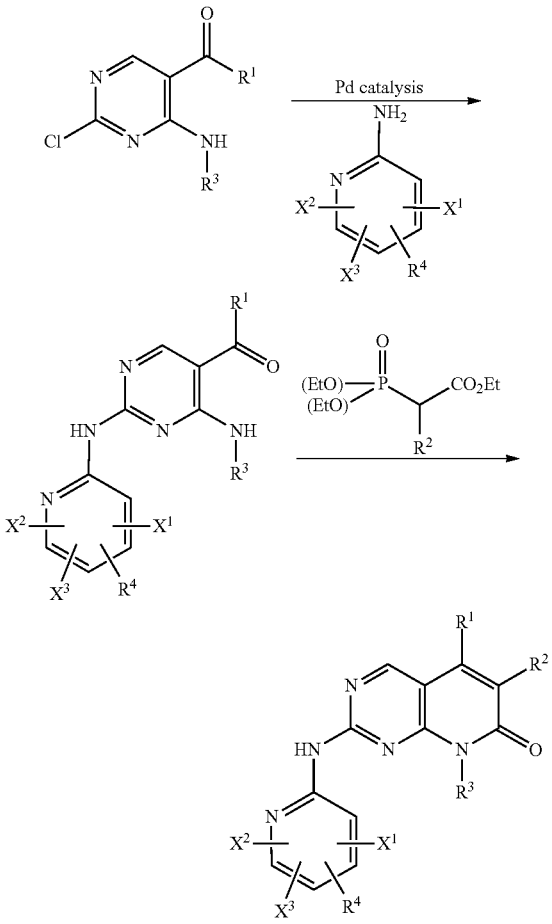

Scheme 13

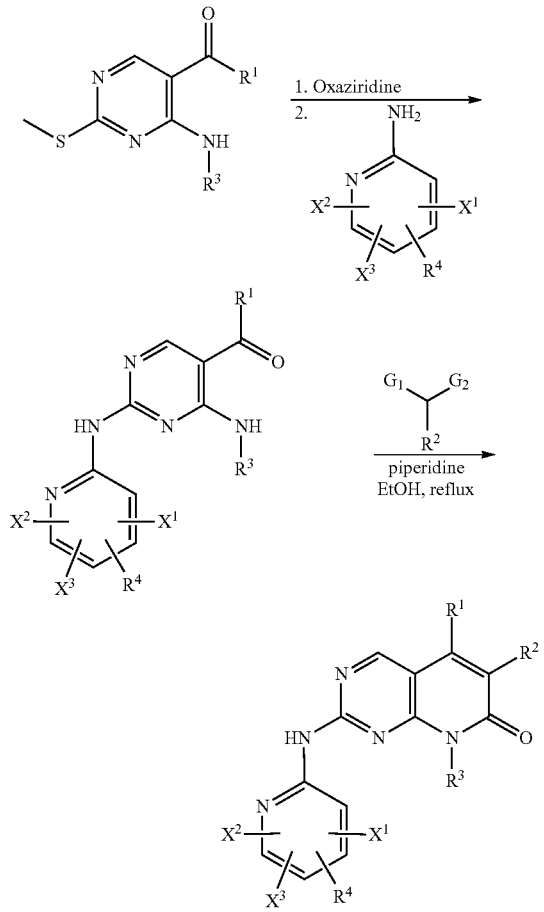

$G_1$ and $G_2$ are electron withdrawing functional groups such as CN, $CO_2Et$, $CO_2Me$, The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

This invention also comprises a pharmaceutical formulation comprising a therapeutically effective amount of a compound of Formula I together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The therapeutically effective dose of a compound of Formula I will vary from approximately 0.01 mg/kg to approximately 100 mg/kg of body weight per day. Typical adult doses will be approximately 0.1 mg to approximately 3000 mg per day. The quantity of active component in a unit dose preparation may be varied or adjusted from approximately 0.1 mg to approximately 500 mg, preferably about 0.6 mg to 100 mg according to the particular application and the potency of the active component. The composition can, if desired, also contain other compatible therapeutic agents. A subject in need of treatment with a compound of Formula I is administered a dosage of about 0.6 to about 500 mg per day, either singly or in multiple doses over a 24-hour period. Such treatment may be repeated at successive intervals for as long as necessary.

This invention provides a pharmaceutical composition for treating a disorder or condition selected from the group consisting of cell proliferative disorders, such as cancer, vascular smooth muscle proliferation associated with atherosclerosis, postsurgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease.

The examples presented below are intended to illustrate particular embodiments of the invention, and are not intended to limit the scope of the specification or the claims in any way.

Those having skill in the art will recognize that the starting materials may be varied and additional steps employed to produce compounds encompassed by the present invention, as demonstrated by the following examples. The following examples are for illustrative purposes only and are not intended, nor should they be construed as limiting the invention in any manner. Those skilled in the art will appreciate that variations and modifications can be made without violating the spirit or scope of the invention.

EXAMPLE 1

8-Cyclopentyl-2-(pyridin-2-ylamino)-8H-pyrido[2,3-d]pyrimidin-7-one

8-Cyclopentyl-2-methanesulfinyl-8H-pyrido[2,3-d]pyrimidin-7-one (200 mg, 0.7 mmol) prepared as in Example 107 of WO 98/33798 (incorporated herein by reference) and 2-aminopyridine (130 mg, 1.4 mmol) were combined in a 10 mL round-bottomed flask. The flask was purged with nitrogen (10 min), then heated in a 160° C. oil bath (30 min). After cooling, the orange residue was triturated with water to afford an orange solid, which was further purified by reversed-phase HPLC purification. [Vydac C18 TP254 (30 mm×100 mm); A: ACN (acetonitrile)+0.1% TFA (trifluor acetic acid); B; $H_2O$+0.1% TFA; 10%-76% B over 40 min]. 15 mg of 8-cyclopentyl-2-(pyridin-2-ylamino)-8H-pyrido[2,3-d]pyrimidin-7-one was isolated as a yellow solid. Mp: >250° C., Anal. HPLC [Vydac C18 TP254 (4.6×150 mm); A: ACN+0.1% TFA; B; $H_2O$+0.1% TFA; 10%-76% B over 20 min]: >98% Rt=13.9 min.

EXAMPLE 2

4-[6-(6-Bromo-8-cyclopentyl-7-oxo-7,8-dihydro-pyrido[2,3-d]pyrimidin-2-ylamino)-pyridin-3-yl]-pipierazine-1-carboxylic acid tert-butyl ester Under a dry argon atmosphere were combined 6-bromo-8-cyclopentyl-2-methanesulfinyl-8H-pyrido[2,3-d]pyrimidin-7-one (0.78 g, 2.19 mmol, prepared as in Example 107 of WO 98/33798 (incorporated herein by reference)) and 4-(6-amino-pyridin-3-yl)-piperazine-1-carboxylic acid tert-butyl ester (0.67 g, 2.4 mmol) without solvent. The flask was evacuated and heated to 120° C. for 1 hour. The mixture was purified by chromatography on silica gel, eluting with chloroform, to give a yellow foam, 0.288 g. Recrystalization from acetonitrile gave 4-[6-(6-bromo-8-cyclopentyl-7-oxo- 7,8-dihydro-pyrido[2,3-d]pyrimidin-2-ylamino)-pyridin-3-yl]-piperazine-1-carboxylic acid tert-butyl ester (0.266 g, 21%). MS (APCI); $M^+$+1: Calc'd, 570.17, Found, 570.0.

EXAMPLE 3

6-Bromo-8-cyclopentyl-2-(5-piperazin-1-yl-pyridin-2-ylamino)-8H-pyrido [2,3-d]pyrimidin-7-one hydrochloride 4-[6-(6-Bromo-8-cyclopentyl-7-oxo-7,8-dihydro-pyrido [2,3-d]pyrimidin-2-ylamino)-pyridin-3-yl]-piperazine-1-carboxylic acid tert-butyl ester (0.26 g, 0.46 mmol) prepared as in Example 2 was dissolved in 1:1 chloroform/methanol (15 ml), to which was added diethyl ether (25 ml). The solution was purged with anhydrous hydrogen chloride gas and stoppered for 18 hours. The resulting white solid was filtered, washed with diethyl ether and dried in vacuo at 60° C. to give 6-bromo-8-cyclopentyl-2-(5-piperazin-1-yl-pyridin-2-ylamino)-8H-pyrido[2,3-d]pyrimidin-7-one hydrochloride as a pale yellow solid (0.254 g). MS (APCI); $M^+$+1: Calc, 470.12, Found, 470.0. Analyses for $C_{21}H_{24}BrN_2O.1.25\ H_2O.2.2HCl$: Calc'd: C, 44.01; H, 5.05; N, 17.11, Cl (ionic), 13.61; $H_2O$, 3.93. Found: C, 43.74; H, 5.07; N, 16.78; Cl (ionic), 13.73 ; $H_2O$, 3.81

EXAMPLE 4

4-[6-(8-Cyclopentyl-6-ethyl-7-oxo-7,8-dihydro-pyrido[2,3-d]pyrimidin-2-ylamino)-pyridin-3-yl]-piperazine-1-carboxylic acid tert-butyl ester 4-[6-(8-Cyclopentyl-6-ethyl-7-oxo-7,8-dihydro-pyrido[2,3-d]pyrimidin-2-ylamino)-pyridin-3-yl]-piperazine-1-carboxylic acid tert-butyl ester was prepared by addition of 8-cyclopentyl-6-ethyl-2-methanesulfinyl-8H-pyrido[2,3-d] pyrimidin-7-one (0.80 g, 2.62 mmol) and 4-(6-amino-pyridin-3-yl)-piperazine-1-carboxylic acid tert-butyl ester (1.82 g, 6.55 mmol) to toluene (10 ml) followed by heating to 105° C. over 10 hours. The resulting suspension was filtered, the solid washed with toluene and dried in vacuo yielding 4-[6-(8-Cyclopentyl-6-ethyl-7-oxo-7,8-dihydro-pyrido[2,3-d]pyrimidin-2-ylamino)-pyridin-3-yl]-piperazine-1-carboxylic acid tert-butyl ester as a solid (0.204 g). MS (APCI); $M^+$+1; Calc'd 520.3, Found 520.1

EXAMPLE 5

8-Cyclopentyl-6-ethyl-2-(5-piperazin-1-yl-pyridin-2-ylamino)-8H-pyrido[2,3-d]pyrimidin-7-one hydrochloride 4-[6-(8-Cyclopentyl-6-ethyl-7-oxo-7,8-dihydro-pyrido[2,3-d]pyrimidin-2-ylamino)-pyridin-3-yl]-piperazine-1-carboxylic acid tert-butyl ester (0.204 g, 0.39 mmol) prepared as in Example 4 was dissolved in 1:1 chloroform/methanol (16 ml) and purged with anhydrous hydrogen chloride gas. After stirring for 3.5 hours, addition of diethyl ether (8 ml) gave a solid precipitate. The solid was filtered, washed with diethyl ether and dried in vacuo yielding 0.180 g of 8-cyclopentyl-6-ethyl-2-(5-piperazin-1-yl-pyridin-2-ylamino)-8H-pyrido[2,3-d]pyrimidin-7-one hydrochloride as a yellow solid. MS (APCI); $M^+$+1: Calc'd, 420.52, Found, 420.2. Analyses for $C_{34}H_{29}N_7O.1.2\ H_2O.2.1HCl$: Calc'd: C, 53.36; H, 6.52; N, 18.93, Cl (ionic), 14.38; $H_2O$, 4.17. Found: C, 53.25; H, 6.43; N, 18.80; Cl (ionic), 14.36; $H_2O$, 3.87

EXAMPLE 6

2-[5-(4-tert-Butoxycarbonyl-piperazin-1-yl)-pyridin-2-ylamino]-8-cyclopentyl-7-oxo-7,8-dihydro-pyrido [2,3-d]pyrimidine-6-carboxylic acid ethyl ester 8-Cyclopentyl-2-methanesulfinyl-7-oxo-7,8-dihydro-pyrido[2,3d]pyrimidine-6-carboxylic acid ethyl ester (0.936 g, 2.68 mmol) and 4-(6-amino-pyridin-3-yl)-piperazine-1-carboxylic acid tert-butyl ester (3.0 g, 10.8 mmol) were added to toluene (5 ml) and heated to 100° C. 1 hour. Diethyl ether (10 ml) was added causing a solid to precipitate. This solid was collected by filtration, washed with diethyl ether, and dried in vacuo yielding 2-[5-(4-tert-Butoxycarbonyl-piperazin-1-yl)-pyridin-2-ylamino]-8-cyclopentyl-7-oxo-7,8-dihydro-pyrido[2,3-d]pyrimidine-6-carboxylic acid ethyl ester as a yellow solid (0.42 g, 28%). MS (APCI); $M^+$+1: Calc'd 564.29, Found 564.3

EXAMPLE 7

8-Cyclopentyl-7-oxo-2-(5-piperazin-1-yl-pyridin-2-ylamino)-7,8-dihydro-pyrido[2,3-d]pyrimidine-6-carboxylic acid ethyl ester hydrochloride 2-[5-(4-tert-Butoxycarbonyl-piperazin-1-yl)-pyridin-2-ylamino]-8-cyclopentyl-7-oxo-7,8-dihydro-pyrido[2,3-d] pyrimidine-6-carboxylic acid ethyl ester (0.40 g, 0.709 mmol, prepared as in Example 6) was dissolved in a mixture of chloroform (15 ml) and ethanol (15 ml) and the solution was purged with anhydrous hydrogen chloride gas. After 2 hours, the addition of ethyl acetate precipitated a solid which was filtered, washed with diethyl ether and dried in vacuo to yield 0.4 g of 8-cyclopentyl-7-oxo-2-(5-piperazin-1-yl-pyridin-2-ylamino)-7,8-dihydro-pyrido[2,3-d]pyrimidine-6-carboxylic acid ethyl ester hydrochloride as a yellow solid. MS (APCI); $M^+$+1: Calc'd, 464.53, Found, 464.4. Analyses for $C_{24}H_{29}N_7O_3.0.75\ H_2O_{2.0}HCl$: Calc'd: C, 52.41; H, 5.96; N, 17.83, Cl (ionic), 12.89; $H_2O$, 2.46. Found: C, 52.25; H, 5.86; N, 17.85; Cl (ionic), 12.10; $H_2O$, 1.52

EXAMPLE 8

(8-Cyclopentyl-2-methylsulfanyl-7-oxo-7,8-dihydro-pyrido[2,3-d]pyrimidin-6-yl)-carbamic acid tert-butyl ester To anhydrous t-butanol (30 ml) was added 8-cyclopentyl-2-methylsulfanyl-7-oxo-7,8-dihydro-pyrido[2,3-d]pyrimidine-6-carboxylic acid (2.48 g, 8.02 mmol), triethylamine (0.974 g, 9.63 mmol) and over 5 minutes, diphenylphosphorylazide (2.65 g, 9.63 mmol) with stirring. This mixture was heated at 75° C. for 18 hours. The mixture was filtered and the solid was washed with ethyl acetate. The washings were concentrated to an oil enriched in the desired product. The oil was triturated with hexane/diethyl ether and the washings were filtered through silica gel and celite. The filtrate was concentrated in vacuo yielding (8-cyclopentyl-2-methylsulfanyl-7-oxo-7,8-dihydro-pyrido[2,3-d]pyrimidin-6-yl)-carbamic acid tert-butyl ester as a crystalline solid (1.37 g, 45%). MS (APCI): $M^+$+1: Calc'd, 377.16, Found 377.2.

EXAMPLE 9

(8-Cyclopentyl-2-methanesulfinyl-7-oxo-7,8-dihydro-pyrido[2,3-d]pyrimidin-6-yl)-carbamic acid tert-butyl ester (8-Cyclopentyl-2-methylsulfanyl-7-oxo-7,8-dihydro-pyrido[2,3-d]pyrimidin-6-yl)-carbamic acid tert-butyl ester (1.3 g, 3.45 mmol, prepared according to Example 8) was added to 50:50 dichloromethane/methanol (12 ml) followed by 2-benzenesulfonyl-3-phenyl-oxaziridine (1.08 g, 4.14 mmol). The mixture was stirred at 25° C. for 3.5 hours, evaporated to an oil and eluted through silica gel with chloroform. Fractions containing the product were evaporated to yield (8-cyclopentyl-2-methanesulfinyl-7-oxo-7,8-dihydro-pyrido[2,3-d]pyrimidin-6-yl)-carbamic acid tert-butyl ester as a solid (1.2 g, 89%). MS (APCI); $M^+$+1: Calc'd, 393.15, Found 393.1.

EXAMPLE 10

4-[6-(6-tert-Butoxycarbonylamino-8-cyclopentyl-7-oxo-7,8-dihydro-pyrido[2,3-d]pyrimidin-2-ylamino)-pyridin-3-yl]-piperazine-1-carboxylic acid tert-butyl ester (8-Cyclopentyl-2-methanesulfinyl-7-oxo-7,8-dihydro-pyrido[2,3-d]pyrimidin-6-yl)-carbamic acid tert-butyl ester (1.2 g, 3.06 ml, prepared according to Example 9) and 4-(6-amino-pyridin-3-yl)-piperazine-1-carboxylic acid tert-butyl ester (2.36 g, 8.48 mmol) were combined in toluene (4 ml) and heated to 105° C. for 12 hours. The resulting paste was diluted with toluene, filtered, washed with toluene and partitioned between diethyl ether and 1 N citric acid. The mixture was filtered, and the solid was washed with water and diethyl ether. The solid then was dissolved in chloroform, dried over anhydrous magnesium sulfate, filtered, and the filtrate diluted with diethyl ether, giving a solid precipitate. This solid was collected by filtration and dried in vacuo to give 4-[6-(6-tert-butoxycarbonylamino-8-cyclopentyl-7-oxo-7,8-dihydro-pyrido[2,3-d]pyrimidin-2-ylamino)-pyridin-3-yl]-piperazine-1-carboxylic acid tert-butyl ester as a solid (0.311 g, 17%). MS (APCI) $M^+$+1; Calc'd, 607.3, Found, 607.2.

EXAMPLE 11

6-Amino-8-cyclopentyl-2-(5-piperazin-1-yl-pyridin-2-ylamino)-8H-pyrido[2,3-d]pyrimidin-7-one hydrochloride 4-[6-(6-tert-Butoxycarbonylamino-8-cyclopentyl-7-oxo-7,8-dihydro-pyrido[2,3-d]pyrimidin-2-ylamino)-pyridin-3-yl]-piperazine-1-carboxylic acid tert-butyl ester (0.31 g, 0.511 mmol) prepared as in Example 10, was added to 1:1 chloroform/methanol (20 ml) and the mixture was purged with anhydrous hydrogen chloride gas then stirred at room temperature for 18 hours. The resulting solid was collected by filtration, washed with diethyl ether, and dried in vacuo to provide 6-amino-8-cyclopentyl-2-(5-piperazin-1-yl-pyridin-2-ylamino)-8H-pyrido[2,3-d]pyrimidin-7-one hydrochloride as a yellow solid (0.202 g, 100%). MS (APCI); $M^+$+1: Calc'd, 407.48, Found, 407.4. Analyses for $C_{21}H_{26}N_8O.1.25\ H_2O.2HCl$: Calc'd: C, 50.46; H, 6.02; N, 22.14, Cl (ionic), 15.98; $H_2O$, 4.58. Found: C, 50.25; H, 6.13; N, 22.32; Cl (ionic), 14.13; $H_2O$, 4.49

EXAMPLE 12

6-Bromo-8-cyclopentyl-2-[5-((S)-1-methyl-1-pyrrolidin-2-yl)-pyridin-2-ylamino]-8H-pyrido[2,3-d]pyrimidin-7-one hydrochloride To dry toluene (4 ml) was added 5-(1-methyl-pyrrolidin-2-yl)-pyridin-2-ylamine (1.19 g, 6.7 mmol, prepared as described in WO 01/70730) and 6-bromo-8-cyclopentyl-2-methanesulfinyl-8H-pyrido[2,3-d]pyrimidin-7-one (1.0 g, 2.81 mmol) and the mixture was heated at 105° C. for 1 hour. The mixture was cooled, filtered, washed with toluene and diethyl ether and dried to a solid in vacuo (0.256 g). The solid was dissolved in chloroform (20 ml) and treated with anhydrous hydrogen chloride gas giving a gummy precipitate. Methanol (2 ml) was added causing the precipitate to dissolve, and the solution was added to rapidly stirred diethyl ether giving a white precipitate. The solid was collected by filtration, washed with diethyl ether and dried in vacuo to provide 6-bromo-8-cyclopentyl-2-[5-((R)-1-methyl-1-pyrrolidin-2-yl)-pyridin-2-ylamino]-8H-pyrido[2,3-d]pyrimidin-7-one hydrochloride (0.30 g, 23%) as a white solid. MS (APCI); $M^+$+1: Calc'd, 469.13, Found, 469.1. Analyses for $C_{22}H_{25}BrN_6O.0.75\ H_2O.1.75HCl$: Calc'd: C, 48.33; H, 5.20; N, 15.37, Cl (ionic), 11.34; $H_2O$, 2.47. Found: C, 48.23; H, 5.29; N, 15.21; Cl (ionic), 11.55 $H_2O$, 3.81

EXAMPLE 13

6-Bromo-8-cyclohexyl-2-(pyridin-2-yl-amino)-8H-pyrido[2,3-d]pyrimidin-7-one

6-Bromo-8-cyclohexyl-2-methanesulfinyl-8H-pyrido[2,3-d]pyrimidin-7-one (1.04 g, 2.81 mmol) was prepared by the method described in WO 98/33798 and mixed with 2-aminopyridine (2.5 g, 26.6 mmol). The mixture was heated in the absence of added solvent to 92° C. for 4 hours giving a solid precipitate. The mixture was filtered when its temperature was between 24-60° C., and the resulting solid was washed with toluene, then chloroform and dried in vacuo to provide 6-bromo-8-cyclohexyl-2-(pyridin-2-yl-amino)-8H-pyrido[2,3-d]pyrimidin-7-one as a yellow solid (0.126 g, 17%). MS (APCI); $M^+$+1: Calc'd, 401.27, Found, 401.1. Analyses for $C_{18}H_{18}BrN_5O$: Calc'd: C, 54.01; H, 4.53; N, 17.50; Br, 19.96. Found: C, 53.87; H, 4.52; N, 15.21; Br, 20.09.

EXAMPLE 14

6-Bromo-8-cyclopentyl-2-methyl-8H-pyrido[2.3-d]pyrimidin-7-one; compound with 6-methyl-nicotinamide 6-Bromo-8-cyclopentyl-2-methanesulfinyl-8H-pyrido[2,3-d]pyrimidin-7-one (1.09 g, 3.06 mmol) and 6-amino-nicotinamide (2.51 g, 18 mmol) were combined in toluene (8 ml) and heated to 100° C. for 18 hours. The mixture then was diluted with dimethylsulfoxide (8 ml) and heated to 120° C. for 2 hours. The mixture then was poured into water (120 ml) with rapid stirring. Diethyl ether was added and the resulting solid was collected by filtration. This solid was washed with 1:1 warm ethyl acetate/tetrahydrofuran and dried in vacuo to provide 6-bromo-8-cyclopentyl-2-methyl-8H-pyrido[2,3-d]pyrimidin-7-one as a yellow solid (0.233 g, 18%). MS (APCI); $M^+$+1: Calc'd, 429.06, Found, 429.1. Analyses for $C_{18}H_{17}BrN_6O_2$:

EXAMPLE 15

6-Bromo-8-cyclopentyl-5-methyl-2-(5-piperizin-1-yl-pyridin-2-ylamino)-8H-pyrido[2,3-d]pyrimidin-7-one 6-Bromo-8-cyclopentyl-2-methanesulfinyl-5-methyl-8H-pyrido[2,3-d]pyrimidin-7-one (0.2 g, 0.54 mmol, prepared according to Example 5 in WO 01/70741) and 4-(6-Amino-pyridin-3-yl)-piperazine-1-carboxylic acid tert-butyl ester (0.6 g, 2.16 mmol) were combined in toluene (3 mL) and heated to 110° C. overnight. The reaction was quenched by the addition of succinic anhydride (0.2 g) and allowed to cool giving a solid. This solid was suspended in $CH_2Cl_2$ and filtered to give a white solid. The filtrate was washed with saturated aqueous sodium bicarbonate then saturated aqueous sodium chloride and dried over anhydrous magnesium sulfate. The crude product was purified by silica gel chromatography eluting with 75% ethyl acetate:25% hexanes to provide 4-[6-(6-Bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (0.04 g, 13%). MS (APCI) $M^+$+1: Calc'd, 584.19, Found, 584.1.

4-[6-(6-Bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (0.04 g, 0.07 mmol) was suspended in $CH_2Cl_2$ (10 mL) and MeOH was added in order to produce a solution (up to ~6 mL). 2 M HCl in ether (10 mL) was added with stirring. The reaction mixture was stirred at room temperature for a total of 3 days then the solvents were removed by evaporation at reduced pressure. The remaining solid was suspended in ether and filtered to give 6-bromo-8-cyclopentyl-5-methyl-2-(5-piperizin-1-yl-pyridin-2-ylamino)-8H-pyrido[2,3-d]pyrimidin-7-one as a yellow solid, which was dried in vacuo at 50° C. MS (APCI); $M^+$+1: Calc'd, 486.15, Found, 486.1. Analyses for $C_{23}H_{26}N_7OBr.2.64H_2O.2.0HCl$: Calc'd: C, 43.68; H, 5.55; N, 16.21, Cl (ionic), 11.72. Found: C, 44.08; H, 5.32; N, 15.23, Cl (ionic), 11.65.

EXAMPLE 16

8-Cyclopentyl-6-fluoro-2-methanesulfinyl-8H-pyrido[2,3-d]pyrimidin-7-one

8-Cyclopentyl-6-fluoro-2-methylsulfanyl-8H-pyrido[2,3-d]pyrimidin-7-one (10.5 g, 37.9 mmol) and 2-benzenesulfonyl-3-phenyl-oxaziridine (11.8 g, 45.4 mmol) were combined in dichloromethane (120 ml) and stirred at room temperature for 18 hours. The mixture was evaporated to an oil, crystallized from ethyl acetate/diethyl ether, filtered and dried in vacuo to provide 8-cyclopentyl-6-fluoro-2-methanesulfinyl-8H-pyrido[2,3-d]pyrimidin-7-one as a white solid (8.88 g, 79.6%).

$^1$H NMR δ (400 MHz, $CDCl_3$) 8.94 (s, 1H), 7.25 (d, 1H), 6.06-5.99 (m, 1H), 2.98 (s, 3H), 2.28-2.21 (m, 2H), 2.18-2.12 (m, 2H), 2.02-1.94 (m, 2H), 1.74-1.67 (m, 2H).

EXAMPLE 17

4-[6-(8-Cyclopentyl-6-fluoro-7-oxo-7,8-dihydro-pyrido[2,3-d]pyrimidin-2-ylamino)-pyridin-3-yl]-piperazine-1-carboxylic acid tert-butyl ester 8-Cyclopentyl-6-fluoro-2-methanesulfinyl-8H-pyrido[2,3-d]pyrimidin-7-one (2.0 g, 6.77 mmol, prepared accoring to Example 16) and 5,4-(6-Amino-pyridin-3-yl)-piperazine-1-carboxylic acid tert-butyl ester (6.0 g, 21 mmol) were added to toluene (8 ml) and heated to 98° C. for 18 hours. The mixture was filtered, washed with toluene and the solid suspended in diethyl ether. The mixture was filtered and the solid was dissolved in chloroform, washed with 1 N citric acid, brine and dried over anhydrous magnesium sulfate. The crude product was triturated with diethyl ether and dried in vacuo to provide 4-[6-(8-cyclopentyl-6-fluoro-7-oxo-7,8-dihydro-pyrido[2,3-d]pyrimidin-2-ylamino)-pyridin-3-yl]-piperazine-1-carboxylic acid tert-butyl ester as a solid (0.88 g, 25%). MS (APCI) $M^+$+1: Calc'd, 510.3, Found 510.2.

EXAMPLE 18

8-Cyclopentyl-6-fluoro-2-(5-piperazin-1-yl-pyridin-2-ylamino)-8H-pyrido[2,3-d]pyrimidin-7-one hydrochloride 4-[6-(8-Cyclopentyl-6-fluoro-7-oxo-7,8-dihydro-pyrido[2,3-d]pyrimidin-2-ylamino)-pyridin-3-yl]-piperazine-1-carboxylic acid tert-butyl ester (0.195 g, 0.38 mmol) prepared as in Example 17, was dissolved in 1:1 chloroform/methanol (8 ml), purged with anhydrous hydrogen chloride gas and stirred for 2.5 hours at room temperature. To the mixture was added diethyl ether (15 ml) giving a precipitate that was filtered, washed with ether and dried in vacuo to provide 8-cyclopentyl-6-fluoro-2-(5-piperazin-1-yl-pyridin-2-ylamino)-8H-pyrido[2,3-d]pyrimidin-7-one hydrochloride as a yellow solid (0.177 g, 88%). MS (APCI); $M^+$+1: Calc, 410.46, Found, 410.3. Analyses for $C_{21}H_{24}N_7O.1.0\ H_2O.2.0HCl$: Calc'd: C, 50.73; H, 5.75; N, 19.46, Cl (ionic), 13.77; $H_2O$, 1.41. Found: C, 50.41; H, 5.64; N, 19.59; Cl (ionic), 14.16; $H_2O$, 3.60.

EXAMPLE 19

4-16-(8-Cyclopentyl-6-methyl-7-oxo-7,8-dihydro-pyrido[2,3-d]pyrimidin-2-ylamino)-pyridin-3-yl]-piperazine-1-carboxylic acid tert-butyl ester 8-Cyclopentyl-6-methyl-2-methanesulfinyl-8H-pyrido[2,3-d]pyrimidin-7-one (1.0 g, 3.43 mmol) was added to 4-(6-amino-pyridin-3-yl)-piperazine-1-carboxylic acid tert-butyl ester (1.91 g, 6.86 mmol) in toluene (5 ml). The mixture was heated to 100° C. over 18 hours then treated with diethyl ether to produce a precipitate. This precipitate was collected by filtration then dried in vacuo to provide 4-[6-(8-cyclopentyl-6-methyl-7-oxo-7,8-dihydro-pyrido[2,3-d]pyrimidin-2-ylamino)-pyridin-3-yl]-piperazine-1-carboxylic acid tert-butyl ester as a yellow solid (0.411 g). MS (APCI) $M^+$+1: Calc'd, 506.28, Found 506.2.

EXAMPLE 20

8-Cyclopentyl-6-methyl-2-(5-piperazin-1-yl-pyridin-2-ylamino)-8H-pyrido[2,3-d]pyrimidin-7-one hydrochloride 4-[6-(8-Cyclopentyl-6-methyl-7-oxo-7,8-dihydro-pyrido[2,3-d]pyrimidin-2-ylamino)-pyridin-3-yl]-piperazine-1-carboxylic acid tert-butyl ester (0.411 g, 0.813 mmol), prepared as in Example 19, was dissolved in a 1:1 mixture of methanol/chloroform, purged with anhydrous hydrogen chloride gas, stirred for 2 hours at room temperature and a solid precipitated by addition of diethyl ether. The suspension was filtered and the residue dried in vacuo yielding 8-cyclopentyl-6-methyl-2-(5-piperazin-1-yl-pyridin-2-ylamino)-8H-pyrido[2,3-d]pyrimidin-7-one hydrochloride as a yellow solid (0.393 g). (APCI); $M^+$+1: Calc'd, 406.50, Found, 406.2. Analyses for $C_{22}H_{27}N_7O.2.85\ H_2O.2.2HCl$: Calc'd: C, 49.20; H, 6.55; N. 18.26, Cl (ionic), 14.52; $H_2O$, 9.56 Found: C, 49.43; H, 6.32; N, 17.87; Cl (ionic), 14.38 ; $H_2O$, 7.35

EXAMPLE 21

4-[6-(8-Cyclopentyl-6-isobutoxy-7-oxo-7,8-dihydro-pyrido[2,3-d]pyrimidin-2-ylamino)-pyridin-3-yl]-piperazine-1-carboxylic acid tert-butyl ester 60% Sodium hydride in oil (0.182 g, 4.4 mmol) was washed with hexane and added to 2-methyl-1-propanol (10 ml). This mixture effervesced and formed a solution. To this solution was added 4-[6-(8-cyclopentyl-6-fluoro-7-oxo-7,8-dihydro-pyrido[2,3-d]pyrimidin-2-ylamino)-pyridin-3-yl]-piperazine-1-carboxylic acid tert-butyl ester (0.225 g, 0.44 mmol, prepared as in Example 17) and the mixture was heated at 95° C. for 72 hours. The solvents were evaporated, and the residue was dissolved in diethyl ether then filtered. The filtrate was evaporated to provide 4-[6-(8-cyclopentyl-6-isobutoxy-7-oxo-7,8-dihydro-pyrido[2,3-d]pyrimidin-2-ylamino)-pyridin-3-yl]-piperazine-1-carboxylic acid tert-butyl ester as a crystalline solid (0.092 g, 37%). MS (APCI) $M^+$+1: Calc'd, 564.3, Found 564.3.

EXAMPLE 22

8-Cyclopentyl-6-isobutoxy-2-(5-piperazin-1-yl-pyridin-2-ylamino)-8H-pyrido[2.3-d]pyrimidin-7-one hydrochloride 4-[6-(8-Cyclopentyl-6-isobutoxy-7-oxo-7,8-dihydro-pyrido[2,3-d]pyrimidin-2-ylamino)-pyridin-3-yl]-piperazine-1-carboxylic acid tert-butyl ester (0.067 g, 0.119 mmol) was dissolved in chloroform (5 ml), cooled to 0° C. This solution was purged with anhydrous hydrogen chloride gas and stoppered for 3 hours. Diethyl ether was added to the mixture giving a precipitate that was filtered and dried in vacuo to provide 8-cyclopentyl-6-isobutoxy-2-(5-piperazin-1-yl-pyridin-2-ylamino)-8H-pyrido[2,3-d]pyrimidin-7-one hydrochloride as a solid (0.056 g). MS (APCI); $M^+$+1: Calc'd, 464.5, Found, 464.3. Analyses for $C_{25}H_{33}N_7O_2$.1.0 $H_2O$.2.0HCl: Calc'd: C, 54.15; H, 6.72; N, 17.68, Cl (ionic), 12.78; $H_2O$, 3.25. Found: C, 54.18; H, 6.98; N, 17.51; Cl (ionic), 12.15; $H_2O$, 2.60.

EXAMPLE 23

4-[6-(6-Benzyl-8-cyclopentyl-7-oxo-7,8-dihydro-pyrido[2,3-d]pyrimidin-2-ylamino)-pyridin-3-yl]-piperazine-1-carboxylic acid tert-butyl ester 6-Benzyl-8-cyclopentyl-2-methanesulfinyl-8H-pyrido[2,3-d]pyrimidin-7-one (0.64 g, 1.74 mmol) and 4(6-Amino-pyridin-3-yl)-piperazine-1-carboxylic acid tert-butyl ester (0.87 g, 2.96 mmol) in toluene (10 ml) were heated to 95° C. for 28 hours. The reaction mixture was allowed to cool then chromatographed on silica gel using a gradient of 20 to 50% ethyl acetate in hexane. The product-containing fractions were evaporated and the residue was triturated with acetonitrile to give a solid. This solid was collected by filtration and dried in vacuo to provide 4-[6-(6-benzyl-8-cyclopentyl-7-oxo-7,8-dihydro-pyrido[2,3-d]pyrimidin-2-ylamino)-pyridin-3-yl]-piperazine-1-carboxylic acid tert-butyl ester (0.201 g, 19.8%). MS (APCI) $M^+$+1: Calc'd, 582.31, Found, 582.3.

EXAMPLE 24

6-Benzyl-8-cyclopentyl-2-(5-piperazin-1-yl-pyridin-2-ylamino)-8H-pyrido[2,3-d]pyrimidin-7-one hydrochloride 4-[6-(6-Benzyl-8-cyclopentyl-7-oxo-7,8-dihydro-pyrido[2,3-d]pyrimidin-2-ylamino)-pyridin-3-yl]-piperazine-1-carboxylic acid tert-butyl ester (0.21 g, 0.36 mmol) prepared as in Example 23, was dissolved in 1:1 chloroform:methanol (15 ml), purged with anhydrous hydrogen chloride gas and stoppered for 3 hours. The mixture was poured into diethyl ether (50 ml) to give a precipitate which was filtered and dried in vacuo to provide 6-benzyl-8-cyclopentyl-2-(5-piperazin-1-yl-pyridin-2-ylamino)-8H-pyrido[2,3-d]pyrimidin-7-one hydrochloride (0.162 g). Analyses for $C_{28}H_{31}N_{72}$.1.5 $H_2O$.1.5HCl: Calc'd: C, 57.26; H, 6.09; N, 16.69, Cl (ionic), 9.05; $H_2O$, 4.60. Found: C, 57.95; H, 6.23; N, 16.80; Cl (ionic), 9.87; $H_2O$, 4.59.

EXAMPLE 25

6-Bromomethyl-8-cyclopentyl-2-methylsulfanyl-8H-pyrido[2,3-d]pyrimidin-7-one

8-Cyclopentyl-6-methyl-2-methylsulfanyl-8H-pyrido[2,3-d]pyrimidin-7-one (3.5 g, 12.7 mmol) and N-bromosuccinimide (2.6 g, 14.6 mmol) in carbon tetrachloride (100 ml) were irradiated with ultraviolet light allowing the temperature to reach 45° C. over 3 hours. The mixture was filtered, washed with dilute sodium sulfite solution, then brine, and dried over anhydrous magnesium sulfate. The crude product was chromatographed on silica gel eluting with 1:1 ethyl acetate:hexane to provide 6-bromomethyl-8-cyclopentyl-2-methylsulfanyl-8H-pyrido[2,3-d]pyrimidin-7-one as a crystalline solid yielding (1.46 g, 32% yield), mp 103-105° C.

EXAMPLE 26

Acetic acid 8-cyclopentyl-2-methylsulfanyl-7-oxo-7,8-dihydro-pyrido[2.3-d]pyrimidin-6-ylmethyl ester 6-Bromomethyl-8-cyclopentyl-2-methylsulfanyl-8H-pyrido[2,3-d]pyrimidin-7-one (1.33 g, 3.75 mmol), prepared as in Example 25, and silver acetate (1.03 g, 6.2 mmol) were added to glacial acetic acid (10 ml) and heated to 110° C. for 5 hours.

The solvents then were evaporated at reduced pressure and the resulting residue was suspended in ethyl acetate and filtered. The solid obtained was recrystallized from ethyl acetate to provide acetic acid 8-cyclopentyl-2-methylsulfanyl-7-oxo-7,8-dihydro-pyrido[2,3-d]pyrimidin-6-ylmethyl ester as a solid (0.89 g, 71%). MS (APCI) $M^+$+1; Calc'd 334.11, Found 334.2.

EXAMPLE 27

Acetic acid 8-cyclopentyl-2-methanesulfinyl-7-oxo-7,8-dihydro-pyrido[2,3-d]pyrimidin-6-ylmethyl ester Acetic acid 8-cyclopentyl-2-methylsulfanyl-7-oxo-7,8-dihydro-pyrido[2,3-d]pyrimidin-6-ylmethyl ester (0.85 g, 2.55 mmol), prepared as in Example 26, and 2-benzenesulfonyl-3-phenyl-oxaziridine (0.8 g, 3.06 mmol) were mixed in dichloromethane (20 ml) and stirred at room temperature for 5 hours. To this mixture was added diethyl ether giving a solid precipitate which was filtered and dried in vacuo to provide acetic acid 8-cyclopentyl-2-methanesulfinyl-7-oxo-7,8-dihydro-pyrido[2,3-d]pyrimidin-6-ylmethyl ester as a solid (0.81 g,(91%). MS (APCI) $M^+$+1; Calc'd 350.41, Found 350.2.

EXAMPLE 28

4-[6-(6-Acetoxymethyl-8-cyclopentyl-7-oxo-7,8-dihydro-pyrido[2,3-d]pyrimidin-2-ylamino)-pyridin-3-yl]-piperazine-1-carboxylic acid tert-butyl ester Acetic acid 8-cyclopentyl-2-methanesulfinyl-7-oxo-7,8-dihydro-pyrido[2,3-d]pyrimidin-6-ylmethyl ester (0.80 g, 2.29 mmol), prepared as in Example 27, and 4-(6-Amino-pyridin-3-yl)-piperazine-1-carboxylic acid tert-butyl ester (1.17 g, 4.20 mmol) were added to toluene (8 ml), heated to 96° C. for 6 hours. The reaction mixture was allowed to cool, then filtered and the residue washed with toluene. The resulting solid was dried in vacuo then recrystallized from chloroform/diethyl ether to provide 4-[6-(6-acetoxymethyl-8-cyclopentyl-7-oxo-7,8-dihydro-pyrido[2,3-d]pyrimidin-2-ylamino)-pyridin-3-yl]-piperazine-1-carboxylic acid tert-butyl ester as a solid (0.213 g, 16.5%). MS (APCI) $M^+$+1; Calc'd, 564.2, Found, 564.3.

EXAMPLE 29

8-Cyclopentyl-6-hydroxymethyl-2-(5-piperazin-1-yl-pyridin-2-ylamino)-8H-pyrido[2,3-d]pyrimidin-7-one hydrochloride 4-[6-(6-Acetoxymethyl-8-cyclopentyl-7-oxo-7,8-dihydro-pyrido[2,3-d]pyrimidin-2-ylamino)-pyridin-3-yl]-piperazine-1-carboxylic acid tert-butyl ester (0.21 g , 0.36 mmol), prepared as in Example 28, was dissolved in 1:1 chloroform:methanol (8 ml), and the solution was purged with anhydrous hydrogen chloride gas then allowed to stir for 3 hours at room temperature. This mixture was added to diethyl ether (50 ml) to give a solid which was collected by filtration, washed with diethyl ether, then dried in vacuo to provide 8-cyclopentyl-6-hydroxymethyl-2-(5-piperazin-1-yl-pyridin-2-ylamino)-8H-pyrido[2,3-d]pyrimidin-7-one hydrochloride as a solid (0.17 g, 93%). MS (APCI); $M^+$+1: Calc'd, 422.5, Found, 422.2. Analyses for $C_{22}H_{27}N_7O_2$.1.0 $H_2O$.2.0HCl: Calc'd: C, 51.56; H, 6.10; N, 19.13, Cl (ionic), 13.84; $H_2O$, 3.51. Found: C, 51.13; H, 5.95; N, 19.05; Cl (ionic), 13.70; $H_2O$, 0.67.

EXAMPLE 30

2-[5-(4-tert-Butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester A mixture of 6-bromo-8-cyclopentyl-5-methyl-2-methylsulfanyl-8H-pyrido[2,3-d]pyrimidin-7-one (442 mg, 1.25 mmol, prepared according to Example 9 in WO 01170741), $Pd(OAc)_2$ (312 mg, 1.4 mmol), bis(diphenylphosphinic) propane (400 mg, 0.97 mmol) and N,N-diisopropylethylamine (1.1 g, 8.87 mmol) in EtOH (20 mL) was stirred under ~600 PSI of CO and heated to 100° C. for 16 hours. The solution thus obtained was filtered and the filtrate was concentrated under reduced pressure to yield an orange oil, which was purified by chromatography (20% ethyl acetate/hexane) to give 8-cyclopentyl-5-methyl-2-methylsulfanyl-7-oxo-7,8-dihydro-pyrido[2,3-d]pyrimidine-6-carboxylic acid ethyl ester as an oil (138 mg, 36% yield). $M^+$+1: Calc'd. 348.4, Found, 348.2.

8-cyclopentyl-5-methyl-2-methylsulfanyl-7-oxo-7,8-dihydro-pyrido[2,3-d]pyrimidine-6-carboxylic acid ethyl ester (138 mg, 0.40 mmol) was dissolved in $CH_2Cl_2$ (6 mL) and 2-benzenesulfonyl-3-phenyl-oxaziridine (155 mg, 0.6 mmol) was added. The reaction mixture was stirred at room temperature for 18 hours then the solvent was removed under reduced pressure and the remaining residue was purified by prepative TLC (50% ethyl acetate/hexane). The more polar, product-containing, reaction was extracted into $CH_2Cl_2$ and the solvent evaporated to provide 8-cyclopentyl-2-methanesulfinyl-5-methyl-7-oxo-7,8-dihydro-pyrido[2,3-d]pyrimidine-6-carboxylic acid ethyl ester as a white solid (110 mg, 75.7%). $M^+$+1: Calc'd. 364.4, Found 364.2.

A solution of 8-cyclopentyl-2-methanesulfinyl-5-methyl-7-oxo-7,8-dihydro-pyrido[2,3-d]pyrimidine-6-carboxylic acid ethyl ester (110 mg, 0.30 mmol) and 4-(6-amino-pyridin-3yl)-piperazine-1-carboxylic acid tert-butyl ester (310 mg, 1.1 mmol) in toluene was heated at 100° C. for 10 hours and then cooled to room temperature. Diethyl ether was added to the reaction mixture and the product precipitated. This precipitate was collected by filtration and dried to provide 2-[5-(4-tert-butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester (50 mg, 29%). $M^+$+1: Calc'd. 578.3, Found 578.4.

EXAMPLE 31

8-cyclopentyl-5-methyl-7-oxo-2-(5-piperazin-1-yl-pyridin-2-ylamino)-7,8-dihydro-pyrido[2,3-d]pyrimidine-6-carboxylic acid ethyl ester hydrochloride Anhydrous HCl gas was bubbled through a solution of 2-[5-(4-tert-butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester (50 mg, 0.086 mmol, prepared as in Example 30) in $CH_2Cl_2$/EtOH at room temperature and the reaction was stirred for 24 h. Diethyl ether was added to the reaction mixture and a solid precipitated which was isolated and dried to 8-cyclopentyl-5-methyl-7-oxo-2-(5-piperazin-1-yl-pyridin-2-ylamino)-7,8-dihydro-pyrido[2,3-d]pyrimidine-6-carboxylic acid ethyl ester hydrochloride as a yellow solid (12 mg, 29%). mp 216-218° C. $M^+$+1:. Calc'd. 478.6, Found 478.1. HPLC, retention time: 5.77 min.

EXAMPLE 32

4-[6-(6-Acetyl-8-cyclopentyl-7-oxo-7,8-dihydro-pyrido[2,3-d]pyrimidin-2-ylamino)-pyridin-3yl]-piperazine-1-carboxylic acid tert-butyl ester:

Tributyl(1-ethoxyvinyl)tin (0.39 mL, 1.15 mmol) was added to a mixture of 4-[6-(6-bromo-8-cyclopentyl-7-oxo-7,8-dihydro-pyrido[2,3-d]pyrimidin-2-ylamino)-pyridin-3-yl]-piperazine-1-carboxylic acid tert-butyl ester (440 mg, 0.77 mmol), prepared as in Example 2, and tetrakis(triphenylphosphine)palladium(0) (88 mg, 0.077 mmol) in toluene (5 mL). The reaction mixture was heated at 110° C. for 1 hour then cooled to room temperature. The solid so formed was collected by filtration and washed with toluene, then dried to give 4-[6-(6-acetyl-8-cyclopentyl-7-oxo-7,8-dihydro-pyrido[2,3-d]pyrimidin-2-ylamino)-pyridin-3yl]-piperazine-1-carboxylic acid tert-butyl ester. $M^+$+1: Calc'd. 534.6, Found 534.2.

EXAMPLE 33

6-Acetyl-8-cyclopentyl-2-(5-piperazin-1-yl-pyridin-2-ylamino)-8H-pyrido[2.3-d]pyrimidin-7-one hydrochloride Anhydrous HCl gas was bubbled through a solution of 4-[6-(6-acetyl-8-cyclopentyl-7-oxo-7,8-dihydro-pyrido[2,3-d]pyrimidin-2-ylamino)-pyridin-3yl]-piperazine-1-carboxylic acid tert-butyl ester (398 mg, 0.74 mmol, prepared as in Example 32), in MeOH/$CH_2Cl_2$ (10 mL/10 mL) at room temperature for ~5 min. The reaction mixture was stirred overnight and then solvent was removed under reduced pressure. The remaining solid was triturated with hot ethyl acetate and dried to provide 6-acetyl-8-cyclopentyl-2-(5-piperazin-1-yl-pyridin-2-ylamino)-8H-pyrido[2,3-d]pyrimidin-7-one hydrochloride (329 mg, 76%). mp >300° C. Anal. Calc'd for $C_{23}H_{27}N_7O_2$.4.25 HCl: C, 46.94; H, 5.35; N, 16.66. Found: C, 46.77; H, 5.33; N, 16.30. $M^+$+1: Calc'd: 434.2, Found 434.2.

EXAMPLE 34

4-[6-(6-Bromo-8-cyclopentyl-5-methyl-7-oxo-7.8-dihydro-pyrido[2,3-d]pyrimidin-2-ylamino)-pyridin-3-yl]-piperazine-1-carboxylic acid tert-butyl ester A suspension of 6-bromo-8-cyclopentyl-2-methansulfinyl-5-methyl-8H-pyrido[2,3-d]pyrimidin-7-one (10.00 g, 0.027 mol, prepared as in Example 6 of WO 01/707041 which is incorporated here by reference) and 10.37 g (0.0373 mol) of 4-(6-amino-pyridin-3-yl)-piperazine-1-carboxylic acid tert-butyl ester in toluene (100 mL) was heated under nitrogen in an oil bath for 7 hours. Thin layer chromatography ($SiO_2$, 10% MeOH/DCM) indicated that both starting materials remained. The suspension was heated under reflux for a further 18 hours. The resulting suspension was cooled to room temperature and filtered to give 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (5.93 g, 38%). mp >250° C. MS (APCI); $M^+$+1: Calc'd, 584.2, Found, 584.2

EXAMPLE 35

4-[6-[8-Cyclopentyl-6-(1-ethoxy-vinyl)-5-methyl-7-oxo-7,8-dihydro-pyrido[2,3-d]pyrimidin-2-ylamino]-pyridin-3-yl]-piperazine-1-carboxylic acid tert-butyl ester A suspension of 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (5.93 g, 0.010 mol, prepared as in Example 34) tetrakis (triphenylphosphine)palladium(0) (1.40 g, 0.00121 mol), and tributyl(1-ethoxyvinyl)tin (5.32 mL, 0.0157 mol) in toluene (30 mL) was heated under reflux for 3.5 hours. The mixture was cooled and filtered to give a solid. Purification of the solid by silica gel chromatography using a gradient of 5-66% ethyl acetate/hexane over 15 minutes gave 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester as a yellow foam (4.50 g, 78%). MS (APCI) $M^+$+1; Calc'd 576.2, Found, 576.3.

EXAMPLE 36

6-Acetyl-8-cyclopentyl-5-methyl-2-(5-piperazin-1-yl-pyridin-2-ylamino)-8H-pyrido[2,3-d]pyrimidin-7-one hydrochloride Hydrogen chloride gas was bubbled into an ice-bath cooled solution of 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester (4.50 g, 0.00783 mol, prepared as in Example 35) in DCM (100 mL). The resulting suspension was stoppered and stirred at room temperature overnight, then diluted with diethyl ether (200 mL). The solid was collected by filtration, washed with diethyl ether, and dried to give the hydrochloride salt of 6-acetyl-8-cyclopentyl-5-methyl-2-(5-piperazin-1-yl-pyridin-2-ylamino)-8H-pyrido[2,3-d]pyrimidin-7-one as a yellow solid (4.01 g, 92%). mp 200° C. HPLC, C18 reverse phase, 10-95% gradient of 0.1% TFA/$CH_3CN$ in 0.1% TFA/H2O during 22 minutes: 99.0% at 11.04 minutes. MS (APCI); $M^+$+1: Calc'd, 448.2, Found, 448.3. Anal. Calc'd for $C_{24}H_{29}N_7O_2$.2.4 $H_2O$.1.85HCl: C, 51.64; H, 6.44; N, 17.56, Cl (total), 11.75. Found: C, 51.31; H, 6.41; N, 17.20; Cl (total), 12.11.

EXAMPLE 37

[6-Bromo-8-cyclopentyl-5-methyl-2-(pyridin-2-ylamino)-8H-pyrido[2,3-]pyrimidin-7-one]
*6-Bromo-8-cyclopentyl-5-methyl-(2-pyridin-2-ylamino)-8H-pyrido[2,3-d]pyrimidin-7-one*

A mixture of 6-bromo-8-cyclopentyl-2-methanesulfinyl-5-methyl-8H-pyrido[2,3-d]pyrimidin-7-one (370 mg, 1 mmol, prepared as in Example 6 of WO 01/707041 which is incorporated here by reference) and 2-aminopyridine(140 mg, 1.5 mmol) in toluene (5 mL) was heated at 110° C. for 18 hours then cooled to room temperature. The solid formed was collected by filtration and washed with toluene, then acetone, and dried in vacuo to give 6-bromo-8-cyclopentyl-5-methyl-2-(pyridin-2-ylamino)-8H-pyrido[2,3-d]pyrimidin-7-one as a beige solid (22 mg, 30%). mp 267-268° C. Anal. Calc'd. for $C_{18}H_{18}BrN_5O$.0.33$H_2O$: C, 53.22; H, 4.63; N, 17.24. Found: C, 52.88; H, 4.38; N, 17.04.

EXAMPLE 38

6-Bromo-8-cyclopentyl-2-(Pyridin-2-ylamino)-8H-pyrido[2,3-]pyrimidin-7-one

6-Bromo-8-cyclopentyl-2-methanesulfinyl-8H-pyrido[2,3-d]pyrimidin-7-one and 2-aminopyridine were reacted according to the procedure outlined in Example 37 to provide 6-bromo-8-cyclopentyl-2-(pyridin-2-ylamino)-8H-pyrido[2,3-d]pyrimidin-7-one in 37% yield. mp: 273~275° C. Anal. Calc'd for $C_{17}H_{16}BrN_5O$.0.1$H_2O$: C, 52.62; H, 4.21; N, 18.05. Found C, 52.23; H, 4.10; N, 17.91. $M^+$+1: Calc'd: 386.05, Found 385.9.

EXAMPLE 39

8-cyclopentyl-2-methylsulfanyl-7-oxo-7,8-dihydro-pyrido[2,3-d]pyrimidine-6-carboxylic acid ethyl ester To 4-cyclopentylamino-2-methylsulfanyl-pyrimidine-5-carboxylic acid ethyl ester (92 g, 8 mmol) in THF (80 mL) at −20° C. under nitrogen was added pyridine (2.6 mL, 32 mmol) followed by $TiCl_4$ (1.75 mL, 16 mmol) in $CH_2Cl_2$ (20 mL). The cold bath was removed and the reaction mixture was stirred at room temperature for 1 h. The reaction was quenched with water (10 mL) then diluted with ether and washed three times with saturated aqueous ammonium chloride solution, then once with brine. The organic layer was dried over anhydrous magnesium sulfate. Removal of the drying agents and evaporation of the solvent gave a yellow oil that was used without further purification. This oil was dissolved in dry DMF (150 mL) and treated with 1,8-diazabicyclo[5.4.0]undec-7-ene (119 μL, 0.8 mmol). The resulting solution was heated to 80° C. for 1 h then allowed to cool to room temperature and diluted with ethyl acetate. This mixture was washed with water then with saturated aqueous ammonium chloride solution (3 times), then with brine. The organic layer was dried over anhydrous magnesium sulfate, then filtered and the solvents removed in vacuo to provide a brown oil which crystallized to give a yellow solid upon standing at room temperature. This solid was collected by filtration and rinsed with ethyl acetate then dried in vacuo. The filtrate was concentrated and chromatographed on silica gel eluting with 20-50% ethyl acetate in hexanes to give additional product as a solid upon removal of the solvents. The two solids were combined to provide the desired product, 8-cyclopentyl-2-methylsulfanyl-7-oxo-7,8-dihydro-pyrido[2,3-d]pyrimidine-6-carboxylic acid ethyl ester (1.2 g,) in 42% over the two steps. $^1$H NMR 6 (400 MHz, $CDCl_3$) 8.64 (s, 1H), 8.23 (s, 1H), 5.90-5.99 (m, 1H), 4.37 (q, J=1.8 Hz, 2H), 2.60 (s, 3H), 2.27-2.35 (m, 2H), 2.02-2.10 (m, 2H), 1.81-1.89 (m, 2H), 1.63-1.70 (m, 2H), 1.37 (t, J=7 Hz, 3H).

EXAMPLE 40

8-Cyclopentyl-2-methanesulfinyl-7-oxo-7,8-dihydro-pyrido[2,3-d]pyrimidine-6-carboxylic acid ethyl ester 8-Cyclopentyl-2-methylsulfanyl-7-oxo-7,8-dihydro-pyrido[2,3-d]pyrimidine-6-carboxylic acid ethyl ester (1.2 g, 3.6 mmol) was dissolved in $CH_2Cl_2$ (20 mL) and treated with 2-benzenesulfonyl-3-phenyl-oxaziridine (1.13 g, 4.32 mmol) at room temperature and stirred for 1 day. Following concentration under reduced pressure, the crude reaction mixture was chromatographed on silica gel eluting with ethyl acetate to give 8-cyclopentyl-2-methanesulfinyl-7-oxo-7,8-dihydro-pyrido[2,3-d]pyrimidine-6-carboxylic acid ethyl ester as a white solid (0.85 g, 68%). MS (APCI); $M^+$+1: Calc'd, 350.1, Found 350.0.

EXAMPLE 41

4-(6-Nitro-pyridin-3-yl)-piperazine-1-carboxylic acid tert-butyl ester

5-Bromo-2-nitropyridine (203 g, 1.365 mol), tetra-n-butyl ammonium iodide (25.2 g, 0.068 mol), piperazine (152.8 g, 1.774 mol) and potassium carbonate (207.44 g, 1.50 mol) were mixed in DMSO (2.6 L). The reaction mixture was warmed to 80° C. and exothermed to 100° C. The mixture was allowed to cool back to 80° C. and was maintained at this temperature overnight. After allowing to cool to room temperature the reaction mixture was poured into water (7 L) and the resulting solid was collected by filtration. This solid was triturated twice with dichloromethane (1 L each time). The aqueous mother liquor was extracted with chloroform (4×2 L) and the combined organic layers were washed with water (2 L) then brine (2 L). Re-extraction of the mother liquor with chloroform (3×2 L) was followed by a brine wash (15 L). The combined organic extracts were concentrated to provide an orange solid (490.46 g), which was used without further purification. This solid was dissolved in THF (2 L) and water (500 mL) and sodium bicarbonate (119.22 g, 1.419 mol) were added, followed by di-tert-butyl dicarbonate (262 g, 1.2 mol) portion-wise over 2.5 h such that the temperature did not rise above 26° C. After 3 h the volatile materials were removed under reduced pressure and the residue was diluted with water (1 L) and extracted with dichloromethane (3×1 L). The organic layers were combined and washed with water (1 L). This water was then back-extracted with more dichloromethane (300 mL). The organic extracts were combined and dried with magnesium sulfate, filtered, and concentrated to afford a brown solid. This material was warmed in 2.0 L of ethyl acetate to 60° C. While at 60° C., the solids were removed by filtration to afford the product 4-(6-nitro-pyridin-3-yl)-piperazine-1-carboxylic acid tert-butyl ester as an orange solid (190.93 g, 62%).

EXAMPLE 42

4-(6-Amino-pyridin-3-yl)-piperazine-1-carboxylic acid tert-butyl ester 4-(6-Nitro-pyridin-3-yl)-piperazine-1-carboxylic acid tert-butyl ester (83 g, 0.269 mol) in methanol (1.3 L) plus Raney Nickel (15 g, 50% slurry in water) were placed in a Parr shaker and hydrogenated at 50 psi of hydrogen for 5 h. The reaction mixture was filtered through a pad of celite and concentrated to a brown solid. This material was triturated with diethyl ether (120 mL) for 4 h. Heptane was added and the mixture was cooled to 0° C. for 45 min. The solid was collected by filtration and dried to afford the product 4-(6-amino-pyridin-3-yl)-piperazine-1-carboxylic acid tert-butyl ester as a tan solid (62.46 g, 83%). mp 130-132° C. MS (ESI); $M^+$+1: Calc'd, 279.2, Found 279. Anal. Calc'd for $C_{14}H_{22}N_4O_3$: C, 60.41; H, 7.97; N, 20.13. Found; C, 60.45; H, 7.60; N, 19.87.

EXAMPLE 43

6-Bromo-8-cyclohexyl-2-methanesulfinyl-8H-pyrido[2,3-d]pyrimidin-7-one

8-Cyclohexyl-2-methylsulfanyl-8H-pyrido[2,3-d]pyrimidin-7-one (4 g, 14.5 mmol) was dissolved in dimethyl formamide (100 mL) and to this solution was added N-bromosuccinimide (3.9 g, 21.8 mmol) and benzoylperoxide (0.53 g, 2.2 mmol). The reaction mixture was stirred at room temperature for 3 days then diluted with ethyl acetate and washed with water then twice with saturated aqueous sodium bicarbonate solution. The organic layer was dried over magnesium sulfate, filtered and evaporated to give 6-bromo-8-cyclohexyl-2-methylsulfanyl-8H-pyrido[2,3-d]pyrimidin-7-one a cream colored solid (8 g). This crude intermediate was redissolved in $CH_2Cl_2$ and treated with 2-benzenesulfonyl-3-phenyl-oxaziridine (3.78 g, 14.5 mmol). The resulting solution was stirred at room temperature overnight then concentrated under reduced pressure and chromotographed on silica gel eluting with ethyl acetate. 6-Bromo-8-cyclohexyl-2-methanesulfinyl-8H-pyrido[2,3-d]pyrimidin-7-one was obtained as a colorless solid (3.72 g, 67%). $^1$H NMR: δ (400 MHz, $CDCl_3$) 8.90 (s, 1H), 8.13 (s, 1H), 5.41 (br s, 1H), 2.96 (s, 3H), 2.58-1.70 (m, 2H), 1.87 (br d, J=13 Hz, 2H), 1.31-1.47 (m, 2H), 1.28 (t, J=3 Hz, 2H).

EXAMPLE 44

6-Bromo-8-cyclopentyl-2-methanesulfinyl-8H-pyrido[2,3-d]pyrimidin-7-one

8-Cyclopentyl-2-methylsulfanyl-8H-pyrido[2,3-d]pyrimidin-7-one (5 g, 19 mmol) was suspended in dimethyl-formamide (80 mL) and treated with N-bromosuccinimide (5.1 g, 28.7 mmol) and benzoylperoxide (0.7 g, 2.87 mmol). After stirring at room temperature for 5 h, the reaction mixture was diluted with ethyl acetate and washed with water, saturated aqueous sodium bicarbonate solution and brine, then the organic layer was dried over magnesium sulfate. After filtration and removal of the solvent, the crude product was chromatographed on silica gel eluting with 20% ethyl acetate: 80% hexanes to give 6-bromo-8-cyclopentyl-2-methanesulfinyl-8H-pyrido[2,3-d]pyrimidin-7-one as a fluffy white solid (4.2 g, 65%). $^1$H NMR: δ (400 MHz, $CDCl_3$) 8.56 (s, 1H), 7.98 (s, 1H), 5.97-6.05 (m, 1H), 2.59 (s, 3H), 2.22-2.29 (m, 2H), 2.06-2.07 (m, 2H), 1.86-1.88 (m, 2H), 1.6-1.68 (m, 2H).

EXAMPLE 45

8-Cyclopentyl-6-iodo-5-methyl-2-methylsulfanyl-8H-pyrido[2,3-d]pyrimidin-7-one

The sulfide, 8-cyclopentyl-5-methyl-2-methylsulfanyl-8H-pyrido[2,3-d]pyrimidin-7-one (7.03 g, 25.51 mmol) and iodine (7.12 g, 28.06 mmol) were combined in dry dichloromethane (120 mL). The mixture was shielded from light and stirred at room temperature for 27 minutes. Bis(trifluoroacetoxy)iodobenzene (13.16 g, 30.61 mmol) was added in one portion and the reaction mixture was heated to 37° C. for 2 h, then cooled to room temperature for 2 h. 50% Aqueous (w/v) sodium thiosulfate (114 mL) was added and the two phases were stirred for 30 minutes then separated. The aqueous phase was extracted with dichloromethane (50 mL) and the combined organic phases were washed with 50% aqueous (w/v) sodium thiosulfate (50 mL) and water (4×130 mL). The organic phase was dried, filtered and concentrated in vacuo to give crude product which was purified by chromatography (15% heptane/dichloromethane) to give 8-cyclopentyl-6-iodo-5-methyl-2-methylsulfanyl-8H-pyrido[2,3-d]pyrimidin-7-one (5.94 g, 58%) as a white solid. MS (ESI); $M^+$+1: Calc'd, 401, Found 401. $^1$H NMR δ (300 MHz, $CDCl_3$) 8.91 (s, 1H), 6.12-6.00 (m, 1H), 2.70 (s, 3H), 2.62 (s, 3H), 2.30-2.24 (m, 2H), 2.15-2.0 (m, 2H), 1.93-1.81 (m, 2H), 1.75-1.57 (m, 2H)

EXAMPLE 46

8-Cyclopentyl-6-iodo-2-methanesulfinyl-5-methyl-8H-pyrido[2,3-d]pyrimidin-7-one

8-Cyclopentyl-6-iodo-5-methyl-2-methylsulfanyl-8H-pyrido[2,3-d]pyrimidin-7-one (1.51 g, 3.76 mmol) and 2-benzenesulfonyl-3-phenyloxaziridine (0.98 g, 3.76 mmol) were combined in dichloromethane (14 mL) and stirred at room temperature until no starting material remained. The solvent was removed in vacuo and the residue was purified by chromatography (gradient 50% ethyl acetate in heptane to 100% ethyl acetate) to provide 8-cyclopentyl-6-iodo-2-methanesulfinyl-5-methyl-8H-pyrido[2,3-d]pyrimidin-7-one (1.16 g, 74%) as a white solid. MS (ESI); $M^+$+1: Calc'd, 418, Found 418. $^1$H NMR δ (300 MHz, $CDCl_3$) 9.13 (s, 1H), 6.14-6.02 (m, 1H), 2.98 (s, 3H), 2.80 (s, 3H), 2.27-2.06 (m, 4H), 2.00-1.87 (m, 2H), 1.72-1.63 (m, 2H).

EXAMPLE 47

6-Bromo-8-cyclopentyl-2-methanesulfinyl-8H-pyrido[2,3-d]pyrimidin-7-one

Prepared from 6-bromo-8-cyclopentyl-2-methylsulfanyl-8H-pyrido[2,3-d]pyrimidin-7-one following the procedure described for 8-cyclopentyl-6-iodo-2-methanesulfinyl-5-methyl-8H-pyrido[2,3-d]pyrimidin-7-one. MS (APCI) Calc'd for $C_{13}H_{14}BrN_3O_2S$: 357, 355.0. Found: 358 (M+1), 356. $^1$H NMR δ (400 MHz, DMSO-$d_6$) 9.14 (s, 1H), 8.63 (s, 1H), 5.91 (m, 1H), 2.89 (s, 3H), 2.15 (br s, 2H), 2.04 (br s, 2H), 1.87-1.79 (m, 2H), 1.61-1.58 (m, 2H).

EXAMPLE 48

6-Bromo-8-cyclopentyl-2-methanesulfinyl-5-methyl-8H-pyrido[2,3-d]pyrimidin-7-one Prepared from 6-bromo-8-cyclopentyl-5-methyl-2-methylsulfanyl-8H-pyrido[2,3-d]pyrimidin-7-one following the procedure described for 8-cyclopentyl-6-iodo-2-methanesulfinyl-5-methyl-8H-pyrido[2,3-d]pyrimidin-7-one. MS (APCI) Calc'd for $C_{14}H_{16}BrN_3O_2S$: 371.01, 369.01. Found: 372.9 (M+1), 371.9. $^1$H NMR δ (400 MHz, $CDCl_3$) 9.01 (s, 1H), 6.06-5.97 (m, 1H), 2.93 (s, 3H), 2.67 (s, 3H), 2.67 (s, 3H), 2.21-2.11 (m, 2H), 2.10-2.04 (m, 2H), 1.94-1.87 (m, 2H), 1.67-1.62 (m, 2H).

EXAMPLE 49

4-[6-(8-Cyclopentyl-6-iodo-5-methyl-7-oxo-7,8-dihydro-pyrido[2,3-d]pyrimidin-2-ylamino)-pyridin-3-yl]-piperazine-1-carboxylic acid tert-butyl ester 8-Cyclopentyl-6-iodo-2-methanesulfinyl-5-methyl-8H-pyrido[2,3-d]pyrimidin-7-one (100 mg, 0.240 mmol) and 2-amino-4-tert-butoxycarbonyl-piperazinylpyridine (96 mg, 0.34 mmol) in anhydrous toluene (3 mL) were heated to 110-120° C. in a sealed tube for 42 h. The mixture was cooled to room temperature and diluted with dichloromethane (20 mL). This mixture was washed with water (10 mL) and brine (10 mL) then dried over anhydrous sodium sulfate, decanted, and concentrated under reduced pressure to a solid, which was triturated with toluene to provide 4-[6-(8-cyclopentyl-6-iodo-5-methyl-7-oxo-7,8-dihydro-pyrido[2,3-d]pyrimidin-2-ylamino)-pyridin-3-yl]-piperazine-1-carboxylic acid tert-butyl ester (63 mg, 41%) as a yellow-orange solid. MS (ESI); $M^+$+1: Calc'd, 632, Found 632. $^1$H NMR δ (300 MHz, $CDCl_3$) 8.88 (s, 1H), 8.73 (bs, 1H), 8.19 (d, J=9.1 Hz, 1H), 8.08 (d, J=2.8 Hz, 1H), 7.33 (dd, J=3, 9.1 Hz, 1H), 5.99 (pent. J=8.7 Hz, 1H), 3.60 (m, 4H), 3.15-3.11 (m, 4H), 2.69 (s, 3H), 2.35-2.28 (m, 2H), 2.13-2.09 (m, 2H), 1.89-1.86 (m, 2H), 1.71-1.63 (m, 2H), 1.50 (s, 9H).

EXAMPLE 50

8-Cyclopentyl-6-iodo-5-methyl-2-(5-piperazin-1-yl-pyridin-2-ylamino)-8H-pyrido[2,3-d]pyrimidin-7-one 4-[6-(8-cyclopentyl-6-iodo-5-methyl-7-oxo-7,8-dihydro-pyrido[2,3-d]pyrimidin-2-ylamino)-pyridin-3-yl]-piperazine-1-carboxylic acid tert-butyl ester (60 mg, 0.096 mmol) and anhydrous dichloromethane (4 mL) under nitrogen were treated dropwise over 10 minutes with trifluoroacetic acid (0.4 mL, 5 mmol). After stirring for 2.6 h, the reaction mixture was concentrated under reduced pressure. The resulting residue was dissolved in dichloromethane (2×2 mL) and concentrated under reduced pressure. The residue then was triturated with anhydrous ethyl ether (2×2 mL) to give 63 mg of an orange solid. This solid was partitioned between dichloromethane and saturated aqueous sodium bicarbonate. Insoluble material was removed by filtration.

The aqueous layer was extracted with dichloromethane (2×10 mL) and the combined organic solutions were dried over sodium sulfate, decanted and concentrated under reduced pressure to a yellow residue, which was purified by chromatography (5% methanol in dichloromethane+1% $NH_4OH$) to give 8-cyclopentyl-6-iodo-5-methyl-2-(5-piperazin-1-yl-pyridin-2-ylamino)-8H-pyrido[2,3-d]pyrimidin-7-one as a yellow solid (15 mg, 28%). Mp >240° C. MS (ESI); $M^+$+1: Calc'd, 532, Found 532. $^1$H NMR 8 (300 MHz, $CDCl_3$) 8.79 (s, 1H), 8.16 d, J=9.1 Hz, 1H), 8.02 (d, J=2.8 Hz, 1H), 7.84 (s, 1H), 8.02 (d, J=2.8 Hz, 1H), 7.84 (s, 1H), 7.35-7.31 (m, 1H), 5.99 (pent. J=8.7 Hz, 1H), 3.20-3.13 (m, 4H), 3.08-3.05 (m, 4H), 2.69 (s, 3H), 2.34-2.25 (m, 2H), 2.11-2.02 (m, 2H), 1.89-1.86 (m, 2H), 1.71-1.63 (m, 2H).

EXAMPLE 51

8-Cyclopentyl-6-ethyl-2-(4-hydroxy-3,4,5,6-tetrahydro-2H-[1,3']bipyridinyl-6'-ylamino)-8H-pyrido[2,3-d]pyrimidin-7-one 8-Cyclopentyl-6-ethyl-2-methanesulfonyl-8H-pyrido[2,3-d]pyrimidin-7-one (0.115 g, 0.47 mmol) and 6'-amino-3,4,5,6-tetrahydro-2H-[1,3']bipyridinyl-4-ol (0.117 g, 0.61 mmol) were combined in dry xylenes and heated at 140° C. under nitrogen overnight. The crude reaction mixture then was allowed to cool and diluted with $CH_2Cl_2$. A precipitate was collected by filtration and dried in vacuo to give 8-cyclopentyl-6-ethyl-2-(4-hydroxy-3,4,5,6-tetrahydro-2H-[1,3']bipyridinyl-6'-ylamino)-8H-pyrido[2,3-d]pyrimidin-7-one (15 mg, 7%). MS (APCI); $M^+$+1: Calc'd, 435.2, Found 435.2.

EXAMPLE 52

4-{6-[8-Cyclopentyl-6-(2-ethoxy-ethoxy)-7-oxo-7,8-dihydro-pyrido[2,3-d]pyrimidin-2-ylamino]-pyridin-3-yl}-piperazine-1-carboxylic acid tert-butyl ester 8-Cyclopentyl-6-(2-ethoxy-ethoxy)-2-methanesulfinyl-8H-pyrido[2,3-d]pyrimidin-7-one (1.2 mL of a 0.46 M solution in toluene, 0.552 mmol) and 4-(6-amino-pyridin-3-yl)-piperazine-1-carboxylic acid tert-butyl ester (0.307 g, 1.1 mmol) were combined in toluene under nitrogen and heated to 110° C. After 4 h the toluene was replaced by xylenes (1 mL) and heating was continued under reflux overnight. After cooling to room temperature the crude reaction mixture was dissolved in $CH_2Cl_2$ and washed with saturated aqueous ammonium chloride solution then with brine. The organic layer was dired ($MgSO_4$), filtered and evaporated to dryness. Chromotagraphy on silica gel eluting with 5% $CH_3OH$ in $CH_2Cl_2$ followed by a second chromatography step eluting with ethyl acetate provided 4-{6-[8-cyclopentyl-6-(2-ethoxy-ethoxy)-7-oxo-7,8-dihydro-pyrido[2,3-d]pyrimidin-2-ylamino]-pyridin-3-yl}-piperazine-1-carboxylic acid tert-butyl ester (70 mg, 22%) as a yellow solid. MS (APCI); $M^+$+1: Calc'd, 580.32, Found 580.2. $^1$H NMR: δ (400 MHz, DMSO) 8.50 (s, 1H), 8.26 (d, J=9 Hz, 1H), 7.94 (d, J=3 Hz, 1H), 7.39 (dd, J=3,9 Hz, 1H), 6.78 (s, 1H), 5.89-5.98 (m, 1H), 4.15 (t, J=5 Hz, 2H), 3.86 (t, J=5 Hz, 2H), 3.56-3.62 (m, 6H), 3.09 (br t, J=5 Hz, 4H), 2.29-2.33 (m, 2H), 2.07-2.10 (m, 2H), 1.84-1.92 (m, 2H), 1.63-1.69 (m, 2H), 1.47 (s, 9H), 1.22 (t, J=7 Hz, 3H).

EXAMPLE 53

8-Cyclopentyl-6-(2-ethoxy-ethoxy)-2-(5-piperazin-1-yl-pyridin-2-ylamino)-8H-pyrido[2,3-d]pyrimidin-7-one 4-{6-[8-Cyclopentyl-6-(2-ethoxy-ethoxy)-7-oxo-7,8-dihydro-pyrido[2,3-d]pyrimidin-2-ylamino]-pyridin-3-y}-piperazine-1-carboxylic acid tert-butyl ester (70 mg, 0.12 mmol) was dissolved in $CH_2Cl_2$ (2.5 mL) and 2 M HCl in ether (2.5 mL) was added. This mixture was stirred for 2 h at room temperature and a yellow precipitate formed. The solvents were removed under reduced pressure and the resulting solid was suspended in ether and collected by filtration then dried overnight in vacuo at 50° C. to give 8-cyclopentyl-6-(2-ethoxy-ethoxy)-2-(5-piperazin-1-yl-pyridin-2-ylamino)-8H-pyrido[2,3-d]pyrimidin-7-one hydrochloride salt (30 mg, 52%). MS (APCI); $M^+$+1: Calc'd, 480.3, Found 480.4. Anal. Calc'd for $C_{25}H_{33}N_7O_3$ 2HCl 3.44 $H_2O$: C, 48.87; H, 6.87; N, 15.96. Found; C, 48.48; H, 6.66; N, 15.66.

EXAMPLE 54

2-{5-[Bis-(2-methoxy-ethyl)-amino]-pyridin-2-ylamino}-6-bromo-8-cyclopentyl-5-methyl-8H-pyrido[2,3-d]pyrimidin-7-one 6-Bromo-8-cyclopentyl-2-methanesulfinyl-5-methyl-8H-pyrido[2,3-d]pyrimidin-7-one (0.4 g, 1.08 mmol) and $N^5$,$N^5$-Bis-(2-methoxy-ethyl)-pyridine-2,5-diamine (0.5 g, 2.2 mmol) were combined in toluene (3.5 mL) and heated to 110° C. After 5 h the reaction mixture was allowed to cool and the crude product was directly chromatographed on silica gel eluting with a gradient of 25% to 100% ethyl acetate in hexanes to provide 2-{5-[bis-(2-methoxy-ethyl)-amino]-pyridin-2-ylamino}-6-bromo-8-cyclopentyl-5-methyl-8H-pyrido[2,3-d]pyrimidin-7-one (0.49 g, 85%) as an orange gum. mp 94-95° C.; MS (APCI); $M^+$+1: Calc'd, 530.2, Found 530.1. Anal. Calc'd for $C_{24}H_{32}N_6O_3Br_1$ 0.13 $H_2O$: C, 54.00; H, 5.90; N, 15.74. Found; C, 53.61; H, 5.68; N, 15.60.

EXAMPLE 55

6-Acetyl-2-{5-[bis-(2-methoxy-ethyl)-amino]-pyridin-2-ylamino}-8-cyclopentyl-5-methyl-8H-pyrido[2,3-d]pyrimidin-7-one 2-{5-[Bis-(2-methoxy-ethyl)-amino]-pyridin-2-ylamino}-6-bromo-8-cyclopentyl-5-methyl-8H-pyrido[2,3-d]pyrimidin-7-one (0.4 g, 0.75 mmol), tributyl-(1-ethoxy-vinyl)-stannane (0.42 g, 1.175 mmol) and palladium tetrakistriphenylphosphine (0.1 g, 0.09 mmol) were combined in $N_2$-purged toluene (4 mL) and heated to 110° C. After 2 h the reaction mixture was allowed to cool and solid 40% KF on alumina (0.2 g) was added. This mixture was diluted with toluene (15 mL) and mixed by swirling for 2 minutes. After filtering and removal of the solvents, the crude product was chromatographed on silica gel eluting with 50-65% ethyl acetate in hexanes to give an orange gum (0.298 g). This gum was dissolved in $CH_2Cl_2$ and washed with 10% KF in $H_2O$, then brine and dried ($MgSO_4$). Following removal of the drying agent and evaporation of the solvent, the remaining material was dissolved in ethyl acetate (10 mL) and treated with 1 M HCl (aqueous). The resulting mixture was stirred vigorously for 1 h at room temperature. Sufficient $CH_2Cl_2$ was added to dissolve the precipitate that had formed and the organic solution was washed with saturated aqueous sodium bicarbonate solution. The aqueous layer was back extracted twice with $CH_2Cl_2$ and the combined organic layers were dried ($MgSO_4$). Removal of the drying agent and evaporation of the solvent gave a foamy solid, which was dissolved in ethyl acetate (20 mL) and filtered then diluted with an equal volume of hexanes and stored at 4° C. The yellow crystals that formed were collected by filtration and dried in vacuo to give 6-acetyl-2-{5-[bis-(2-methoxy-ethyl)-amino]-pyridin-2-ylamino}-8-cyclopentyl-5-methyl-8H-pyrido[2,3-d]pyrimidin-7-one (120 mg, 32%). Mp 138-138° C. MS (APCI); $M^+$+1: Calc'd, 494.3, Found 495.3. Anal. Calc'd for $C_{26}H_{34}N_6O_4$: C, 63.14; H, 6.93; N, 16.99. Found; C, 63.04; H, 6.77; N, 16.86.

EXAMPLE 56

4-[6-(8-isopropyl-7-oxo-7,8-dihydro-pyrido[2,3]pyrimidin-2-ylamino)-pyridin-3-yl]-piperazine-1-carboxylic acid tert-butyl ester A mixture of 2-chloro-8-isopropyl-8H-pyrido[2,3-d]pyrimidin-7-one (338 mg, 1.5 mmol) and 4-(6-amino-pyridin-3-yl)-piperazine-1-carboxylic acid tert-butyl ester (460 mg, 2.0 mmol) in toluene (6 mL) was heated at 110° C. for ~20 h and then cooled to room temperature. The solid was collected by filtration, washed with toluene, and dried. The sample was dissolved in $CH_2Cl_2$ and purified by two preparative TLC plates (eluted in 10% MeOH/$CH_2Cl_2$). The band with $R_f$=0.23 was extracted to give 4-[6-(8-isopropyl-7-oxo-7,8-dihydro-pyrido[2,3]pyrimidin-2-ylamino)-pyridin-3-yl]-piperazine-1-carboxylic acid tert-butyl ester as a yellow solid (180 mg, 26%). $^1$H NMR. δ (400 MHz, DMSO) 9.29 ( s, 1H), 8.80 (br, 1H), 8.17~8.9 (m, 2H), 7.70 (d, J=2.5 Hz, 1H), 7.2 (d, J=9.8 Hz, 1H), 6.88 (d, J=9.6 Hz, 1H), 5.6~5.5 (m, 1H), 4.06 (m, 1H), 3.4~3.9 (m, 4H), 3.14 (d, J=5.2 Hz, 2H), 2.98 (m, 4H), 1.52 (s, 3H), 1.1.50 (s, 3H), 1.38 (s, 9H)

EXAMPLE 57

8-isopropyl-2-(5-piperazin-1-yl-pyridin-2-ylamino)-8H-pyrido[2.3-d]pyrimidin-7-one HCl gas was bubbled through a solution of 4-[6-(8-isopropyl-7-oxo-7,8-dihydro-pyrido[2,3]pyrimidin-2-ylamino)-pyridin-3-yl]-piperazine-1-carboxylic acid tert-butyl ester (180 mg, 0.39 mmol) in $CH_2Cl_2$ (5 mL) at room temperature. The light yellow solid formed was collected by filtration five hours later. The solid was hygroscopic so it was dissolved in MeOH and a few drops of water were added to the solution. The solvent was then removed under reduced pressure to generate a glass solid. The solid was washed with acetone and dried further to yield 8-isopropyl-2-(5-piperazin-1-yl-pyridin-2-ylamino)-8H-pyrido[2,3-d]pyrimidin-7-one hydrochloride salt (101 mg, 66%). mp 237-240° C. $^1$H NMR δ (400 MHz, DMSO-$d_6$) 9.38 (br s, 1H), 9.28 (s, 1H), 8.88 (br s, 1H), 8.14 (d, J=9.5 Hz, 1H), 8.07 (d, J=9.0 Hz, 1H), 7.73 (s, 1H), 7.23 (d, J=9.5 Hz, 1H), 6.85 (d, J=9.5 Hz, 1H), 5.57-5.01 (m, 1H), 5.57-5.01 (m, 1H), 3.23 (br s, 4H), 3.17 (br s, 4H), 1.49 (s, 3H), 1.47 (s, 3H).

EXAMPLE 58

4-[6-(8-cyclopentyl-7-oxox-7,8-dihydro-pyrido[2,3-d]pyrimidin-2-ylamino)-pyridin-3-yl]-piperazine-1-carboxylic acid tert-butyl ester A mixture of 8-cyclopentyl-2-methanesulfinyl-8H-pyrido[2,3-]pyrimidine-7-one (416 mg, 1.5 mmol) and 4-(6-amino-pyridin-3-yl)-piperazine-1-carboxylic acid tert-butyl ester (460 mg, 2.0 mmol) in toluene (6 mL) was heated at 110° C. for ~20 hours then cooled to room temperature. The solid formed was collected by filtration, washed with toluene and dried to yield the desired product 4-[6-(8-cyclopentyl-7-oxo-7,8-dihydro-pyrido[2,3-d]pyrimidin-2-ylamino)-pyridin-3-yle]-piperazine-1-carboxylic acid tert-butyl ester (143 mg,) in 19.4% yield. $^1$H NMR δ (400 MHz, DMSO) 9.97 (s, 1H), 8.72 (s, 1H), 8.03 (d, J=3.0 Hz, 1H), 7.85 (m, 1H), 7.74 (d, J=9.2 Hz, 1H), 7.25 (m, 1H), 6.31 (d, J=9.3 Hz, 1H), 5.80 (m, 1H), 3.4 (m, 4H), 3.28 (m, 4H), 2.47 (m, 2H), 1.9 (m, 2H), 1.87 (br, 2H), 1.6~1.8 (br, 2H), 1.5~1.6 (m, 2H), 1.39 (s, 9H).

EXAMPLE 59

8-cyclopentyl-2-(5-piperazin-1-yl-pyridin-2-ylamino)-8H-pyrido[2,3-d]pyrimidin-7-one A solution of 4-[6-(8-cyclopentyl-7-oxo-7,8-dihydro-pyrido[2,3-d]pyrimidin-2-ylamino)-pyridin-3-yl]-piperazine-1-carboxylic acid tert-butyl ester (143 mg, 0.29 mmol) in $CH_2Cl_2$/MeOH (6 mL/1.5 mL) was treated with HCl gas at room temperature for ~3 min. The solution was stirred at room temperature for ~6 hours then filtered to collect the solid. This solid was washed with $CH_2Cl_2$ and dried in vacuo to yield 8-cyclopentyl-2-(5-piperazin-1-yl-pyridin-2-ylamino)-8H-pyrido[2,3-d]pyrimidin-7-one hydrochloride salt (98 mg, 66%). mp 213-215° C. Anal Calc'd for $C_{21}H_{25}N_7O_2O$ HCl 2.5 $H_2O$: C, 49.51; H, 5.90; N, 15.74; N, 15.74; Cl, 13.92. Found: C, 49.64; H, 6.12; N, 19.23, Cl, 14.20.

EXAMPLE 60

4-[6-(8-cyclohexyl-7-oxo-7,8-dihydro-pyrido[2,3-d]pyrimidin-2-ylamino)-pyridin-3-yl]-piperazine-1-carboxylic acid tert-butyl ester A mixture of 8-cyclohexyl-2-methanesufinyl-8H-pyrido[2,3-d]pyrimidine-7-one (430 mg, 1.47 mmol) and 4-(6-amino-pyridin-3-yl)-piperazine-1-carboxylic acid tert-butyl ester (556 mg, 2.43 mmol) in toluene (5 mL) was heated at 100° C. for 18 hours. It was cooled to room temperature and the solid formed was collected and washed with toluene then dried to give 4-[6-(8-cyclohexyl-7-oxo-7,8-dihydro-pyrido[2,3-d]pyrimidin-2-ylamino)-pyridin-3-yl]-piperazine-1-carboxylic acid tert-butyl ester (105 mg, 14%). $^1$H NMR δ (400 MHz, DMSO) 10.02 ( s, 1H), 8.70 (s, 1H), 8.04 (d, J=3.0 Hz, 1H), 7.72 (d, J=9.2 Hz, 1H), 7.44 (dd, J=9.2, 3.1 Hz, 1H), 6.28 (m, 1H), 3.60 (m, 4H), 3.08 (m, 4H), 1.6~1.8 (m, 10H), 1.39 (s, 9H).

EXAMPLE 61

8-cyclohexyl-2-(5-piperazin-1-yl-pyridin-2-ylamino)-8H-pyrido[2,3-d]pyrimidin-7-one HCl gas was bubbled through a solution of 4-[6-(8-cyclohexyl-7-oxo-7,8-dihydro-pyrido[2,3-d]pyrimidin-2-ylamino)-pyridin-3-yl]-piperazine-1-carboxylic acid tert-butyl ester (105 mg, 0.21 mmol) in $CH_2Cl_2$ (3 mL) at room temperature until a solid was formed. The mixture was stirred at room temperature for 6 hours and the solid formed was collected by filtration. The solid was hygroscopic. It was recrystalized from MeOH with addition of a few drops of water to yield 8-cyclohexyl-2-(5-piperazin-1-yl-pyridin-2-ylamino)-8H-pyrido[2,3-d]pyrimidin-7-one hydrochloride salt (40 mg, 35%). mp: 228-230° C. Anal Calc'd for $C_{22}H_{27}N_7O_2O$ HCl 3.5 $H_2O$: C, 48.80; H, 6.70; N, 18.11; Cl, 13.09. Found: C, 48.88; H, 6.39; N, 17.95; Cl, 12.88.

EXAMPLE 62

8-cyclopropyl-2-methylsulfinyl-8H-pyrido[2,3-d] pyrimidin-7-one

A solution of 8-cyclopropyl-2-methylsulfanyl-8H-pyrido [2,3-d]pyrimidin-7-one (0.5 g, 2.1 mmol) and 2-benzenesulfonyl-3-phenyl-oxaziridine (0.84 g, 3.2 mmol) in $CH_2Cl_2$ (5 mL) was stirred at room temperature for 20 hours. The white solid formed was collected by filtration and washed with hexane, then dried to give 8-cyclopropyl-2-methylsulfinyl-8H-pyrido[2,3-d]pyrimidin-7-one (0.388 g, 74%). $^1$H NMR: δ (400 MHz, DMSO) 9.15 (s, 1H), 8.0 (d, J=9.5 Hz, 1H), 6.74 (d, J=9.5 Hz, 1H), 2.92 ( s, 1H), 1.18~1.14 ( m, 2H), 0.83~0.79 (m, 2H).

EXAMPLE 63

4-[6-(8-cyclopropyl-7-oxo-7,8-dihydro-pyrido[2,3-d] pyrimidin-2-ylamino)-pyridin-3-yl-]-piperazine-1-carboxylic acid tert-butyl ester A mixture of 8-cyclopropyl-2-methylsulfinyl-8H-pyrido [2,3-d]pyrimidin-7-one (388 mg, 1.56 mmol) and 4-(6-amino-pyridin-3-yl)-piperazine-1-carboxylic acid tert-butyl ester (462 mg, 2.0 mmol) in toluene (5 mL) was heated at 100° C. for 18 hours. It was cooled to room temperature and the solid was collected by filtration and washed with toluene and dried to give 4-[6-(8-cyclopropyl-7-oxo-7,8-dihydro-pyrido[2,3-d]pyrimidin-2-ylamino)-pyridin-3-yl]-piperazine-1-carboxylic acid tert-butyl ester (96 mg, 13%). $^1$H NMR δ (400 MHz, DMSO) 9.97 (s, 1H), 8.67 (s, 1H), 8.39 (d, J=9.3 Hz, 1H), 8.0 (d, J=2.95 Hz, 1H), 7.71 (d, J=9.3 Hz, 1H), 6.28 (d, J=9.3 Hz, 1H), 3.42 (br, 4H), 3.05 (br, 4H0, 2.80 (m, 1H), 1.37 (s, 9H), 1.20 (d, J=6.1 Hz, 2H), 0.76 (br, 2H).

EXAMPLE 64

8-cyclopropyl-2-(5-piperazin-1-yl-pyridin-2-ylamino)-8H-pyrido[2,3-d]pyrimidin-7-one HCl gas was bubbled through a solution of 4-[6-(8-cyclopropyl-7-oxo-7,8-dihydro-pyrido[2,3-d]pyrimidin-2-ylamino)-pyridin-3-yl]-piperazine-1-carboxylic acid tert-butyl ester (96 mg, 0.21 mMol) in $CH_2Cl_2$ (5 mL) for a few minutes until solid was formed. The mixture was stirred at room temperature for 18 hours and the solid formed was collected by filtration and washed with $CH_2Cl_2$ then dried in vacuo to give the desired product 8-cyclopropyl-2-(5-piperazin-1-yl-pyridin-2-ylamino)-8H-pyrido[2,3-d]pyrimidin-7-one as its hydrochloride salt (83 mg, 85%). mp >300° C. Anal Calc'd for $C_{19}H_{21}N_7O$. 2.1 HCl. 1.5 $H_2O$: C, 48.87; H, 5,63; N, 20.99. Found: C, 49.23; H, 5.53; N, 20.68.

EXAMPLE 65

6-Bromo-8-cyclopentyl-2-(pyridin-2,6-yldiamino)-8H-pyrido[2,3-d]pyrimidin-7-one

A mixture of 6-bromo-8-cyclopentyl-2-methanesulfinyl-8H-pyrido[2,3-d]pyrimidin-7-one (370 mg, 1.0 mmol) and 2,6-diaminopyridine (164 mg, 1.5 mmol) in toluene (5 mL) was heated at 120° C. overnight. The solid formed upon cooling was collected by filtration, washed with toluene, then sonicated in hot methanol and dried to give the desired product 6-bromo-8-cyclopentyl-2-(pyridin-2,6-yldiamino)-8H-pyrido[2,3-d]pyrimidin-7-one (105 mg, 26%). mp >300° C. Anal Calc'd for $C_{17}H_{17}N_6OBr$: C, 50.89; H, 4.27; N, 20.94. Found: C, 51.00; H, 4.20; N, 21.04.

EXAMPLE 66

6-Bromo-8-cyclopentyl-5-methyl-2-(pyridin-2-ylamino)-8H-pyrido[2,3-d]pyrimidin-7-one A mixture of 6-bromo-8-cyclopentyl-2-methanesulfinyl-5-methyl-8H-pyrido[2,3-d]pyrimidin-7-one (370 mg, 1.0 mmol) and 2,6-diaminopyridine (163 mg, 1.5 mmol) in toluene (5 mL) was heated at 120° C. overnight. The solid formed upon cooling was collected by filtration, washed with toluene and sonicated in hot MeOH. After filtration the solid was dried further to give the desired product 2-(6-amino-pyridin-2-ylamino)-6-bromo-8-cyclopentyl-5-methyl-8H-pyrido[2,3-d]pyrimidin-7-one (39 mg, 9.3%). mp: >274.6~276° C. Calc'd for $C_{18}H_{19}BrN_5O.0.2\ H_2O$: C, 51.61; H, 4.67; N, 20.06. Found: C, 51.42; H, 4.44; N, 19.87.

EXAMPLE 67

8-Cyclopentyl-6-ethyl-2-methanesulfonyl-8H-pyrido [2,3-d]pyrimidin-7-one

To a cooled (0° C., ice bath) solution of 8-cyclopentyl-6-ethyl-2-methylsulfanyl-8H-pyrido[2,3-d]pyrimidin-7-one (5.0 g, 17.28 mmol) in dichloromethane (25 mL) under nitrogen was added m-chloroperbenzoic acid (MCPBA) (7.4 g, 30.0 mmol). The cold bath was removed and the reaction mixture was stirred at RT for 3 h. The reaction mixture was poured into aq. $NaHCO_3$ (saturated solution, 100 mL) and extracted three times with dichloromethane (300 mL total). The organic layers were combined and dried over magnesium sulfate. Removal of the drying agents and evaporation of the solvent gave a dark orange oil which was chromatographed on silica gel eluting with an ethyl acetate/dichloromethane gradient to give 8-cyclopentyl-6-ethyl-2-methanesulfonyl-8H-pyrido[2,3-d]pyrimidin-7-one as a white powder. Recrystalization from dichloromethane/hexanes gave white needles (3.56 g, 11.1 mmol). mp 174-176° C. (uncorrected); $^1$H NMR δ (400 MHz, $CDCl_3$) 8.87 (s, 1H), 7.50 (s, 1H), 5.98-5.89 (m, 1H), 3.36 (s, 3H), 2.68 (q, J=7.3 Hz, 2H), 2.30-2.22 (m, 2H), 2.16-2.11 (m, 1H), 1.97-1.89 (m, 1H), 1.72-1.68 (m, 1H), 1.26 (t, J=7.3 Hz, 3H); MS (APCI+) 322 (M+1, 100).

EXAMPLE 68

8-Cyclopentyl-6-(2-ethoxy-ethoxy)-2-methylsulfanyl-8H-pyrido[2,3-d]pyrimidin-7-one To a suspension of sodium hydride (45 mg, 1.1 mmol, 60% oil dispersion) in THF (10 mL), under nitrogen, was added 2-ethoxyethanol (113 mg, 1.25 mmol). The reaction mixture was stirred at RT for 30 min. To this mixture, 8-cyclopentyl-6-fluoro-2-methylsulfanyl-8H-pyrido[2,3-d] pyrimidin-7-one was added. The reaction mixture was then heated to reflux and stirred overnight. The cooled solution was quenched with water (25 mL) and extracted with ethyl acetate (50 mL). The organic layer was subsequently washed twice with aq. $NH_4Cl$ (20 mL each) and brine (20 mL). The organic layer was dried over magnesium sulfate. Removal of the drying agents and evaporation of the solvent gave a yellow oil, which was chromatographed on silica gel eluted with an ethyl acetate/hexane gradient to give 8-cyclopentyl-6-(2-ethoxy-ethoxy)-2-methylsulfanyl-8H-pyrido[2,3-d]pyrimidin-7-one as a clear oil (289 mg, 0.83 mmol). $^1$H NMR δ (400 MHz, $CDCl_3$) 8.52 (s, 1H), 6.77 (s, 1H), 6.04-5.95 (m, 1H), 4.16 (t, J=4.0 Hz, 2H), 3.86 (t, J=4.0 Hz, 2H), 3.58 (q, J=8.0 Hz, 2H), 2.59 (s, 3H), 2.34-2.25 (m, 2H), 2.13-2.03 (m, 2H), 1.91-1.82 (m, 2H), 1.71-1.60 (m, 2H), 1.20 (t, J=8.0 Hz, 3H); MS (APCI+) 350 (M+1).

EXAMPLE 69

8-Cyclopentyl-6-(2-ethoxy-ethoxy)-2-methanesulfinyl-8H-pyrido[2,3-d]pyrimidin-7-one To a solution of 8-cyclopentyl-6-(2-ethoxy-ethoxy)-2-methylsulfanyl-8H-pyrido[2,3-d]pyrimidin-7-one (289 mg, 0.83 mmol) in chloroform (5 mL) was added 2-benzenesulfonyl-3-phenyl-oxaziridine (281 mg, 1.07 mmol). The reaction mixture was stirred at RT overnight, under nitrogen. The solvents were removed and the crude product was chromatographed on silica gel, eluting with a 5% methanol-ethyl acetate/hexane gradient to give 8-cyclopentyl-6-(2-ethoxy-ethoxy)-2-methanesulfinyl-8H-pyrido[2,3-d]pyrimidin-7-one as a clear oil (210 mg, 0.56 mmol). $^1$H NMR δ (400 MHz, $CDCl_3$) 8.84 (s, 1H), 6.89 (s, 1H), 6.06-5.98 (m, 1H), 4.23 (t, J=4.0 Hz, 2H), 3.89 (t, J=4.0 Hz, 2H), 3.60 (q, J=6.9 Hz, 2H), 2.95 (s, 3H), 2.28-2.19 (m, 2H), 2.15-2.10 (m, 2H), 1.97-1.88 (m, 2H), 1.71-1.64 (m, 2H), 1.21 (t, J=6.9 Hz, 3H); MS (APCI+) 350 (M+1).

EXAMPLE 70

6-Bromo-8-cyclopentyl-5-methyl-2-[5-(4-methyl-piperazin-1-yl)-pyridin-2-ylamino]-8H-pyrido[2,3-d]pyrimidin-7-one 6-Bromo-8-cyclopentyl-2-methanesulfinyl-5-methyl-8H-pyrido[2,3-d]pyrimidin-7-one (1.0 g, 2.7 mmol) and 5-(4-methyl-piperazin-1-yl)-pyridin-2-ylamine (1.48 g, 7.7 mmol) were combined in toluene (3.0 ml) under nitrogen. The reaction mixture was heated to reflux and stirred for 4 h. The reaction mixture was cooled to RT and filtered. The solids were washed with additional toluene (25 ml total) and dried in vacuo to produce a yellow powder (338 mg, 0.78 mmol). mp 278-280° C. (dec.); MS (APCI+) 498, 500 (100); $^1$H NMR 6 (400 MHz, $CDCl_3$) 10.71-10.64 (m, 2H), 9.01 (s, 1H), 8.10-8.09 (m, 1H), 7.89 (d, J=0.10 Hz, 1H), 7.52-7.30 (m, 1H), 5.97-5.89 (m, 1H), 3.87-3.84 (m, 2H), 3.53-3.50 (m, 2H), 3.22-3.09 (m, 4H), 2.83-2.82 (m, 3H), 2.60 (s, 3H), 2.21-2.15 (m, 2H), 1.94 (br, 2H), 1.81-1.78 (m, 2H), 1.62-1.60 (M, 2H); Anal. Calc'd for $C_{23}H_{28}BrN_7O_1$ 3.00 $H_2O$ 1.65 HCl 0.60 $C_2H_5OH$: C, 43.70; H, 5.74; N, 14.74. Found; C, 43.76; H, 5.79; N, 14.39.

EXAMPLE 71

8-Cyclopentyl-6-(1-ethoxy-vinyl)-5-methyl-2-[5-(4-methyl-piperazin-1-yl)-pyridin-2-ylamino]-8H-pyrido[2.3-d]pyrimidin-7-one A 6-dram vial was charged with 6-bromo-8-cyclopentyl-5-methyl-2-[5-(4-methyl-piperazin-1-yl)-pyridin-2-ylamino]-8H-pyrido[2,3-d]pyrimidin-7-one (266 mg, 0.53 mmol) and tetrakis(triphenylphosphine) palladium(0) (61 mg, 0.053 mmol) and the atmosphere replaced with argon. Toluene (5 ml) was added followed by tributyl-(1-ethoxy-vinyl)-stannane (289 mg, 0.80 mmol). The vial was heated to 110° C. and stirred for 12 h. The reaction mixture was diluted with chloroform (25 ml) and adsorbed onto silica gel. Chromatographic purification on silica gel (chloroform/2-propanol+1% TEA gradient) gave the 8-cyclopentyl-6-(1-ethoxy-vinyl)-5-methyl-2-[5-(4-methyl-piperazin-1-yl)-pyridin-2-ylamino]-8H-pyrido[2,3-d]pyrimidin-7-one (237 mg, 0.48 mmol). MS (APCI+) 490 (M+1, 100).

EXAMPLE 72

6-Acetyl-8-cyclopentyl-5-methyl-2-[5-(4-methyl-piperazin-1-yl)-pyridin-2-ylamino]-8H-pyrido[2,3-d]pyrimidin-7-one To a solution of 8-cyclopentyl-6-(1-ethoxy-vinyl)-5-methyl-2-[5-(4-methyl-piperazin-1-yl)-pyridin-2-ylamino]-8H-pyrido[2,3-d]pyrimidin-7-one (237 mg, 0.48 mmol) in chloroform (5 ml) was added hydrogen chloride (2 M ethereal solution, 2.0 ml, 4.0 mmol). The reaction mixture was stirred at RT for 12 h. The solvents were evaporated and the residue was dissolved in ethanol. The ethanol was evaporated to give 6-acetyl-8-cyclopentyl-5-methyl-2-[5-(4-methyl-piperazin-1-yl)-pyridin-2-ylamino]-8H-pyrido[2,3-d]pyrimidin-7-one (239 mg mmol). MS (APCI+) 462 (M+1, 100); $^1$H NMR δ (400 MHz, $DMSO_{d6}$) 10.83 (m, 2H), 9.00 (s, 1H), 8.1 (m, 1H), 7.88-7.82 (m, 2H), 5.89-5.80 (m, 1H), 3.88-3.85 (m, 2H), 3.23-3.11 (m, 4H), 2.83-2.82 (m, 3H), 2.43 (s, 3H), 2.34 (s, 3H), 2.23-2.11 (m, 2H), 1.93 (br, 2H), 1.81-1.77 (m, 2H), 1.60-1.59 (m, 2H); Anal. Calc'd for $C_{25}H_{31}N_7O_2$, 2.70 HCl 1.05 $C_2H_5OH$: C, 53.50; H, 6.63; N, 16.12. Found: C, 53.45; H, 6.47; N, 15.85.

EXAMPLE 73

(1-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-pyrrolidin-3-yl)-carbamic acid tert-butyl ester A 6-dram vial was charged with {1-[6-(6-bromo-8-cyclopentyl-5-methyl-7-oxo-7,8-dihydro-pyrido[2,3-d]pyrimidin-2-ylamino)-pyridin-3-y]-pyrrolidin-3-yl}-carbamic acid tert-butyl ester (379 mg, 0.65 mmol) and tetrakis(triphenylphosphine) palladium(0) (75 mg, 0.065 mmol) and the atmosphere replaced with argon. Toluene (5 ml) was added followed by tributyl-(1-ethoxy-vinyl)-stannane (352 mg, 0.97 mmol). The vial was heated to 110° C. and stirred for 12 h. The reaction mixture was diluted with chloroform (25 ml) and adsorbed onto silica gel. Chromatographic purification on silica gel (chloroform/2-propanol+1% TEA gradient) gave (1-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-pyrrolidin-3-yl)-carbamic acid tert-butyl ester as a yellow solid (394 mg, 0.68 mmol). MS: (APCI+) 576 (M+1, 100), 548.

EXAMPLE 74

6-Acetyl-2-[5-(3-amino-pyrrolidin-1-yl)-pyridin-2-ylamino]-8-cyclopentyl-5-methyl-8H-pyrido[2,3-d]pyrimidin-7-one To a solution of (1-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-pyrrolidin-3-yl)-carbamic acid tert-butyl ester (394 mg, 0.68 mmol) in chloroform (5 ml) was added hydrogen chloride (2 M ethereal solution, 2.0 ml, 4.0 mmol). The reaction mixture was stirred at RT for 12 h. The solvents were evaporated and the residue was dissolved in ethanol. The ethanol was evaporated to give 6-acetyl-8-cyclopentyl-5-methyl-2-[5-(4-methyl-piperazin-1-yl)-pyridin-2-ylamino]-8H-pyrido[2,3-d]pyrimidin-7-one (239 mg, 0.52 mmol). MS (APCI+) 487, 391, 279 (100); $^1$H NMR δ (400 MHz, DMSO$_{d6}$) 8.98 (s, 1H), 8.34 (br, 2H), 7.78-7.73 (m, 2H), 7.51 (br, 1H), 5.89-5.80 (m, 1H), 3.98 (br, 2H), 3.62-3.51 (m, 4H), 2.40-3.23 (m, 2H), 2.44 (s, 3H), 2.25-2.20 (m, 2H), 2.16-2.13 (m, 1H), 1.93 (br, 2H), 1.80-1.78 (m, 2H), 1.61-1.58 (m, 2H); Anal. Calc'd for $C_{24}H_{29}N_7O_2$, 2.10 HCl, 2.85 $H_2O$, 0.45 $C_2H_5OH$: C, 50.16; H, 6.68; N, 16.45; Cl$^-$, 12.49. Found: C, 50.37; H, 6.90; N, 16.45; Cl$^-$, 12.61.

EXAMPLE 75

6-Bromo-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one 6-Bromo-8-cyclopentyl-2-methanesulfinyl-5-methyl-8H-pyrido[2,3-d]pyrimidin-7-one (2.50 g, 6.76 mmol) and 6'-amino-3,4,5,6-tetrahydro-2H-[1,3']bipyridinyl-4-ol (1.96 g, 10.13 mmol) were combined in toluene (10.0 ml) under nitrogen. The reaction mixture was heated to reflux and stirred for 4 h. The reaction mixture was cooled to RT and filtered. The solids were washed with additional toluene (75 mL total) and dried in vacuo to produce a yellow powder (566 mg, 1.13 mmol). MS (APCI+) 499, 501 (M+2, 100); $^1$H NMR 6 (400 MHz, DMSO-$_{d6}$) 10.06 (s, 1H), 8.96 (s, 1H), 8.04 (s, 1H), 7.83 (d, J=9.3Hz, 1H), 7.46 (d, J=7.3 Hz, 1H). 5.93-5.89 (m, 1H), 4.71 (s, 1H), 3.65-3.60 (m, 1H), 3.53-3.51 (m, 2H), 2.88-2.83 (m, 2H), 2.57 (s, 3H), 2.18 (br, 2H), 1.90-1.81 (m, 5H), 1.59-1.48 (m, 3H); Anal. Calc'd for $C_{23}H_{27}Br_1N_6O_2$, 0.45 $H_2O$: C, 54.43; H, 5.54; N, 16.56. Found: C, 54.04; H, 5.23; N, 16.33.

EXAMPLE 76

8-Cyclopentyl-6-(1-ethoxy-vinyl)-2-(4-hydroxy-3,4,5,6-tetrahydro-2H-[1,3']bipyridinyl-6'-ylamino)-5-methyl-8H-pyrido[2,3-d]pyrimidin-7-one A 6-dram vial was charged with 6-bromo-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one (316 mg, 0.63 mmol) and tetrakis(triphenylphosphine) palladium (0) (72 mg, 0.063 mmol) and the atmosphere replaced with argon. Toluene (5 mL) was added followed by tributyl-(1-ethoxy-vinyl)-stannane (343 mg, 0.95 mmol). The vial was heated to 110° C. and stirred for 12 h. The reaction mixture was diluted with chloroform (25 ml) and adsorbed onto silica gel. Chromatographic purification on silica gel (chloroform/2-propanol+1% TEA gradient) gave the 6-bromo-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one (255 mg, 0.52 mmol). MS (APCI+) 463, 491 (M+1, 100).

EXAMPLE 77

6-Acetyl-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one To a solution of 8-cyclopentyl-6-(1-ethoxy-vinyl)-2-(4-hydroxy-3,4,5,6-tetrahydro-2H-[1,3']bipyridinyl-6'-ylamino)-5-methyl-8H-pyrido[2,3-d]pyrimidin-7-one (255 mg, 0.52 mmol) in chloroform (2 mL) was added hydrogen chloride (2 M ethereal solution, 5.0 mL, 10.0 mmol). The reaction mixture was stirred at RT for 12 h. The solvents were evaporated and the residue was dissolved in ethanol. The ethanol was evaporated to give 6-acetyl-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one (213 mg, 0.46 mmol). MS (APCI+) 463 (M+1, 100); $^1$HNMR δ (400 MHz, DMSO-$_{d6}$) 10.90 (br, 1H), 9.07 (s, 1H), 8.19 (s, 1H), 7.91 (br, 2H), 5.91-5.89 (m, 1H), 3.77 (br, 1H), 3.62 (br, 2H), 3.07 (br, 2H), 2.58 (s, 3H), 2.40 (s, 3H), 2.30 (br, 2H), 1.98-1.86 (m, 5H), 1.65 (br, 4H); Anal. Calc'd for $C_{25}H_{30}N_6O_3$, 1.76 $C_3H_8O_1$, 0.36 $CHCl_3$: C, 60.20; H, 7.33; N, 13.75. Found: C, 60.48; H, 6.97; N, 13.35.

EXAMPLE 78

4-[6-(6-Bromo-8-cyclopentyl-5-methyl-7-oxo-7,8-dihydro-pyrido[2,3-d]pyrimidin-2-ylamino)-pyridin-3-yl]-azepane-1-carboxylic acid tert-butyl ester A solution of 4-(6-amino-pyridin-3-yl)-azepane-1-carboxylic acid tert-butyl ester (614 mg, 2.10 mmol) in toluene (10 mL) was refluxed in a Dean-Stark apparatus for 3 h. The heat was removed and when the reflux subsided 6-bromo-8-cyclopentyl-2-methansulfinyl-5-methyl-8H-pyrido[2,3-d]pyrimidin-7-one (700 mg, 1.89 mmol) was added. This mixture was refluxed for 12 h under $N_2$. Succinic anhydride (500 mg) was added and the reflux continued for 3 h. The reaction mixture was cooled and dissolved in ethyl acetate (100 ml) and the organic layer was washed with water (100 mL total). The organic layer was dried over magnesium sulfate and the solvents evaporated. The crude product was subjected to chromatography on silica gel and eluted with a chloroform/2-propanol gradient to give 4-[6-(6-bromo-8-cyclopentyl-5-methyl-7-oxo-7,8-dihydro-pyrido[2,3-d]pyrimidin-2-ylamino)-pyridin-3-yl]-azepane-1-carboxylic acid tert-butyl ester as a yellow powder (414 mg, 0.82 mmol). MS (APCI+) 500, 600 (M+1,100).

EXAMPLE 79

6-Bromo-8-cyclopentyl-2-(5-[1,4]diazepan-1-yl-pyridin-2-ylamino)-5-methyl-8H-pyrido[2,3-d]pyrimidin-7-one Hydrogen chloride gas was bubbled through a solution of 4-[6-(6-bromo-8-cyclopentyl-5-methyl-7-oxo-7,8-dihydro-pyrido[2,3-d]pyrimidin-2-ylamino)-pyridin-3-yl]-azepane-1-carboxylic acid tert-butyl ester (80 mg, 0.13 mmol) in chloroform (5 mL) for 30 min. The solvents were evaporated and the residue was titurated with ethanol (5 mL). 6-Bromo-8-cyclopentyl-2-(5-[1,4]diazepan-1-yl-pyridin-2-ylamino)-5-methyl-8H-pyrido[2,3-d]pyrimidin-7-one hydrochloride salt was collected as a yellow powder (44 mg, 0.089 mmol). MS (APCI+) 499, 501 (M+2, 100); $^1$H NMR δ (400 MHz, DMSO-$_{d6}$) 8.84 (s, 2H), 8.13 (s, 1H), 7.66-7.64 (m, 1H), 7.42-7.39 (m, 1H), 5.86-5.82 (m, 1H), 4.36 (s, 1H), 3.81 (s, 2H), 3.60 (s, 2H), 3.16 (s, 2H), 2.09 (s, 4H), 1.99 (s, 2H), 1.79 (br, 2H), 1.60 (s, 2H), 1.05 (s, 2H); Anal. Calc'd for $C_{23}H_{28}Br_1N_7O_1$, 0.15 HCl, 2.55 $C_2H_5OH$, 0.45 $CHCl_3$: C, 50.79; H, 6.55; N, 14.52. Found: C, 50.83; H, 5.69; N, 14.21.

EXAMPLE 80

4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-[1,4]diazepane-1-carboxylic acid tert-butyl ester A 6-dram vial was charged with 4-[6-(6-bromo-8-cyclopentyl-5-methyl-7-oxo-7,8-dihydro-pyrido[2,3-d]pyrimidin-2-ylamino)-pyridin-3-yl]-azepane-1-carboxylic acid tert-butyl ester (123 mg, 0.25 mmol) and tetrakis(triphenylphosphine) palladium(0) (29 mg, 0.025 mmol) and the atmosphere replaced with argon. Toluene (5 mL) was added followed by tributyl-(1-ethoxy-vinyl)-stannane (137 mg, 0.37 mmol). The vial was heated to 110° C. and stirred for 12 h. The reaction mixture was diluted with chloroform (25 mL) and adsorbed onto silica gel. Chromatographic purification on silica gel (chloroform/ethyl acetate gradient) gave 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-[1,4]diazepane-1-carboxylic acid tert-butyl ester as a yellow solid (116 mg, 0.20 mmol). MS: (APCI+) 125 (100), 490, 590 (M+1, 100), 624.

EXAMPLE 81

6-Acetyl-8-cyclopentyl-2-(5-[1,4]diazepan-1-yl-pyridin-2-ylamino)-5-methyl-8H-pyrido[2,3-d]pyrimidin-7-one To a solution 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-[1,4]diazepane-1-carboxylic acid tert-butyl ester (116 mg, 0.20 mmol) in chloroform (5 mL) was added hydrogen chloride (2 M ethereal solution, 5.0 mL, 10.0 mmol). The reaction mixture was stirred at RT for 12 h. The solvents were evaporated and the residue was dissolved in ethanol. The ethanol was evaporated to give 6-acetyl-8-cyclopentyl-2-(5-[1,4]diazepan-1-yl-pyridin-2-ylamino)-5-methyl-8H-pyrido[2,3-d]pyrimidin-7-one hydrochloride salt (47 mg, 0.10 mmol). MS (APCI+) 432, 462 (M+1, 100);

$^1$H NMR δ (400 MHz, DMSO-$_{d6}$) 9.19 (br, 2H), 8.99 (s, 1H), 7.91 (s, 1H), 7.78-7.75 (m, 2H), 5.88-5.80 (m, 1H), 3.80-3.77 (m, 3H), 3.25 (br, 3H), 3.16 (br, 2H), 2.44 (s, 3H), 2.34 (s, 3H), 2.49-2.18 (m, 2H), 2.12-2.10 (m, 2H), 1.93 (br, 2H), 1.81-1.78 (m, 2H), 1.61-1.58 (m, 2H); Anal. Calc'd for $C_{25}H_{31}N_7O_2$, 2.80 HCl, 0.45 $C_3H_8O_2$: C, 53.35; H, 6.25; Found: C, 52.96; H, 6.62; N, 15.95.

EXAMPLE 82

[6-Acetyl-8-cyclopentyl-5-methyl-2-(pyridin-2-ylamino)-8H-pyrido[2,3-d]pyrimindin-7-one] *6-Acetyl-8-cyclopentyl-5-methyl-2 -(pyridin-2-ylamino)-8H-pyrido[2,3-d]pyrimindin-7-one*

6-Acetyl-2-amino-8-cyclopentyl-5-methyl-8H-pyrido[2,3-d]pyrimidin-7-one (195 mg, 0.681 mmol) and sodium tert-butoxide (92 mg, 0.953 mmol) were suspended in $N_2$-purged toluene (5 mL). To this suspension was added 2-bromo pyridine (78 μL), tris(dibenzylideneacetone)-dipalladium(0) (25 mg, 0.027 mmol) and BINAP (34 mg, 0.054 mmol). The reaction vial was purged with argon and the reaction was heated at 70° C. overnight. The reaction mixture was diluted with ether and methanol, filtered through a pad of celite and concentrated under reduced pressure. The crude product was chromatographed on silica gel eluting with a gradient of 40% to 100% ethyl acetate in hexanes. [6-Acetyl-8-cyclopentyl-5-methyl-2-(pyridin-2-ylamino)-8H-pyrido[2,3-d]pyriminin-7-one] *6-Acetyl-8-cyclopentyl-5-methyl-2-(pyridin-2-ylamino)-8H-pyrido[2,3-d]pyriminin-7-one* was obtained as a solid (40 mg, 16%). $^1$H NMR δ (400 MHz, $CDCl_3$) 8.84 (s, 1H), 8.35-8.32 (m, 2H), 8.21 (bs, 1H), 7.75-7.71 (m, 1H), 7.03-7.01 (m, 1H), 5.89-5.85 (m, 1H), 2.54 (s, 3H), 2.37 (s, 3H), 2.03-2.08 (m, 2H), 1.92-1.87 (m, 2H), 1.73-1.67 (m, 2H). MS (APCI) Calc'd for M+H: 363.2, Found: 364.1. Purity by HPLC=92%.

EXAMPLE 83

4-[6-(8-Cyclopentyl-5-methyl-7-oxo-7,8-dihydro-pyrido[2,3-d]pyrimidin-2-ylamino)-pyridin-3-yl]-piperazine-1-carboxylic acid tert-butyl ester 8-Cyclopentyl-2-methanesulfinyl-5-methyl-8H-pyrido[2,3-d]pyrimidin-7-one (0.40 g, 1.37 mmol) and 4-(6-amino-pyridin-3-yl)-piperazine-1-carboxylic acid tert-butyl ester (0.497 g, 1.78 mmol) were heated to reflux in toluene (4 mL) for 16 hours. The reaction mixture was cooled to room temperature and the precipitate that formed was collected by filtration and washed on the funnel with toluene (3×10 mL) to give 4-[6-(8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester as a dark brown-gray solid (0.100 g, 16.2%). $^1$H NMR δ (400 MHz, DMSO-$d_6$) 9.92 (s, 1H), 8.78 (s, 1H), 8.02 (d, J=2.9 Hz, 1H), 7.87 (d, J=9.3 Hz, 1H), 7.50 (dd, J=2.9, 9.0 Hz, 1H), 6.18 (s, 1H), 5.77 (m, 1H), 3.44 (m, 4H), 3.07 (m, 4H), 2.39 (s, 3H), 2.20 (m, 2H), 1.85 (m, 2H), 1.71 (m, 2H), 1.55 (m, 2H), 1.39 (s, 9H).

EXAMPLE 84

8-Cyclopentyl-5-methyl-2-(5-piperazin-4-yl-pyridin-2-ylamino)-8H-pyrido[2,3-d]pyrimidin-7-one 4-[6-(8-Cyclopentyl-5-methyl-7-oxo-7,8-dihydro-pyrido[2,3-d]pyrimidin-2-ylamino)-pyridin-3-yl]-piperazine-1-carboxylic acid tert-butyl ester (0.093 g, 0.184 mmol) was dissolved in dichloromethane (3 mL) to which 2 N HCl in diethyl ether (2 mL) was added and the resulting mixture was stirred for 2 days. Additional 2 N HCl was added and stirring was continued for 16 hours. The solvent was removed to give 8-cyclopentyl-5-methyl-2-(5-piperazin-4-yl-pyridin-2-ylamino)-8H-pyrido[2,3-d]pyrimidin-7-one hydrochloride salt as a yellow solid (0.080 g, 90.9%). $^1$H NMR δ (400 MHz, DMSO-$d_6$) 9.92 (s, 2H), 8.85 (s, 1H), 8.02 (d, J=2.9 Hz, 1H), 7.91 (d, J=9.3 Hz, 1H), 7.78 (d, J=9.3 Hz, 1H), (m, 1H), 3.40 (m, 4H), 3.22 (m, 4H), 2.39 (s, 3H), 2.20 (m, 2H), 1.91 (m, 2H), 1.74 (m, 2H), 1.56 (m, 2H).

EXAMPLE 85

2,2-Dimethyl-4-(6-nitro-pyridin-3-yl)-piperazine-1-carboxylic acid tert-butyl ester 5-Bromo-2-nitropyridine (10.67 g, 52.6 mmol), tetra-n-butyl ammonium iodide (0.97 g, 02.63 mmol), 2,2-dimethyl-piperazine (6.60 g, 57.8 mmol) and potassium carbonate (8.00 g, 57.8 mmol) were mixed in DMSO (50 mL). The reaction mixture was warmed to 95° C. for 5 hours. The reaction mixture was poured onto ice chips (approximately 200 mL) then extracted with dichloromethane (6×75 mL).

The combined organics were dried over $MgSO_4$, the inorganic salts were removed by filtration and the remaining solvents were concentrated to provide an orange solid. This solid was dissolved in dichloromethane (100 mL) to which triethylamine (10.65 g, 14.7 mL, 105 mmol) and di-tert-butyl dicarbonate (13.8 g, 63.12 mmol) were added. After 16 hours, more di-tert-butyl dicarbonate (3.8 g, 17.41 mmol) was added and the mixture was brought to reflux for 3 hours. The reaction mixture was then cooled to room temperature and diluted with dichloromethane (100 mL) and washed with water (1×100 mL). The organic layer was then dried over $MgSO_4$, filtered, and the solvent evaporated to yield 2,2-dimethyl-4-(6-nitro-pyridin-3-yl)-piperazine-1-carboxylic acid tert-butyl ester as an orange solid (14.91 g, 84.2%). $^1$H NMR δ (400 MHz, $CDCl_3$) 8.17 (d, J=9.3 Hz, 1H), 7.97 (d, J=2.9 Hz, 1H), 7.01 (dd, J=2.9, 9.0 Hz, 1H), 3.91 (m, 2H), 3.54 (m, 4H), 1.48 (s, 9H), 1.43 (s, 6H).

EXAMPLE 86

4-(6-Amino-pyridin-3-yl)-2,2-dimethyl-piperazine-1-carboxylic acid tert-butyl ester 2,2-Dimethyl-4-(6-nitro-pyridin-3-yl)-piperazine-1-carboxylic acid tert-butyl ester (14.63 g, 43.5 mmol) was dissolved in THF (400 mL) to which Raney Nickel (6.8 g) was added. The reaction mixture was shaken under a hydrogen atmosphere (50 psi) for 4 hours. The catalyst was removed by filtration and the solvent evaporated to give 4-(6-amino-pyridin-3-yl)-2,2-dimethyl-piperazine-1-carboxylic acid tert-butyl ester as a purple solid (11.26 g, 84.5 %). $^1$H NMR δ (400 MHz, $CDCl_3$) 7.63 (d, J=2.4 Hz, 1H), 7.06 (dd, J=2.9, 8.8 Hz, 1H), 6.51 (d, J=8.8 Hz, 1H), 3.68 (m, 2H), 3.16 (m, 2H), 2.98 (s, 2H), 1.48 (s, 9H), 1.43 (s, 6H).

EXAMPLE 87

4-[6-(6-Bromo-8-cyclopentyl-5-methyl-7-oxo-7,8-dihydro-pyrido[2,3-d]pyrimidin-2-ylamino)-pyridin-3-yl]-2,2-dimethyl-piperazine-1-carboxylic acid tert-butyl ester 6-Bromo-8-cyclopentyl-2-methanesulfinyl-5-methyl-8H-pyrido[2,3-d]pyrimidin-7-one (1.0 g, 2.70 mmol) and 4-(6-amino-pyridin-3-yl)-2,2-dimethyl-piperazine-1-carboxylic acid tert-butyl ester (1.14 g, 3.73 mmol) were heated to reflux in toluene (10 mL) for 16 hours. The reaction mixture was cooled to room temperature and the precipitate that formed was collected by filtration and washed on the funnel with toluene (3×10 mL) to give 4-[6-(6-bromo-8-cyclopentyl-5-methyl-7-oxo-7,8-dihydro-pyrido[2,3-d]pyrimidin-2-ylamino)-pyridin-3-yl]-2,2-dimethyl-piperazine-1-carboxylic acid tert-butyl ester as a dark brown-gray solid (0.525 g, 31.8%). $^1$H NMR δ (400 MHz, DMSO-$d_6$) 9.96 (s, 1H), 8.91 (s, 1H), 7.89 (d, J=2.7 Hz, 1H), 7.74 (d, J=8.8 Hz, 1H), 7.26 (dd, J=3.2, 9.3 Hz, 1H), 6.18 (s, 1H), 5.86 (m, 1H), 3.67 (m, 2H), 3.37 (m, 4H), 2.54 (s, 3H), 2.15 (m, 2H), 1.84 (m, 2H), 1.71 (m, 2H), 1.53 (m, 2H), 1.39 (s, 9H), 1.33 (s, 6H).

EXAMPLE 88

6-Bromo-8-cyclopentyl-2-[5-(3,3-dimethyl-piperazin-1-yl)-pyridin-2-ylamino]-5-methyl-8H-pyrido[2,3d]pyrimidin-7-one 4-[6-(6-Bromo-8-cyclopentyl-5-methyl-7-oxo-7,8-dihydro-pyrido[2,3-d]pyrimidin-2-ylamino)-pyridin-3-yl]-2,2-dimethyl-piperazine-1-carboxylic acid tert-butyl ester (0.051 g, 0.083 mmol) was dissolved in dichloromethane (3 mL) to which 2 N HCl (2 mL) was added and the resulting mixture was stirred at room temperature for 2 hours. This mixture was concentrated and allowed to sit for 10 days, it was then dissolved in 2 N HCl (2 mL) and stirred at room temperature for 5 hours. The solvent was removed to give 6-bromo-8-cyclopentyl-2-[5-(3,3-dimethyl-piperazin-1-yl)-pyridin-2-ylamino]-5-methyl-8H-pyrido[2,3-d]pyrimidin-7-one hydrochloride salt as a yellow solid (0.035 g, 71.4%). $^1$H NMR δ (400 MHz, DMSO-$d_6$) 9.32 (s, 2H), 8.98 (s, 1H), 8.04 (d, J=2.7 Hz, 1H), 7.83 (d, J=9.3 Hz, 1H), 7.26 (m, 1H), 5.89 (m, 2H), 3.34 (m, 2H), 3.23 (m, 4H), 2.58 (s, 3H), 2.14 (m, 2H), 1.91 (m, 2H), 1.77 (m, 2H), 1.57 (m, 2H), 1.38 (s, 6H).

EXAMPLE 89

4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,2-dimethyl-piperazine-1-carboxylic acid tert-butyl ester 4-[6-(6-Bromo-8-cyclopentyl-5-methyl-7-oxo-7,8-dihydro-pyrido[2,3-d]pyrimidin-2-ylamino)-pyridin-3-yl]-2,2-dimethyl-piperazine-1-carboxylic acid tert-butyl ester (0.412 g, 0.673 mmol), tetrakis(triphenylphosphine)palladium (0.093 g, 0.081 mmol) and tributyl-(1-ethoxy-vinyl)-stannane (0.379 g, 1.05 mmol) were dissolved in toluene (3 mL) and slowly brought to reflux for 1 hour. The solvent was evaporated and the solid was redissolved in dichloromethane (8 mL) and purified by silica gel chromatography to give 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl} -2,2-dimethyl-piperazine-1-carboxylic acid tert-butyl ester as a yellow solid (0.405 g, 99.0%). $^1$H NMR δ (400 MHz, $CDCl_3$) 8.73 (s, 1H), 8.15 (d, J=9.0 Hz, 1H), 8.00 (s, 1H), 7.85 (d, J=2.9 Hz, 1H), 7.18 (m, 1H), 5.90 (m, 1H), 4.52 (d, J=2.4 Hz, 1H), 4.18 (d, J=2.4 Hz, 1H), 3.93 (q, J=7.1 Hz, 2H), 3.80 (m, 2H), 3.38 (m, 2H), 3.26 (s, 2H), 2.41 (s, 3H), 2.35 (m, 2H), 2.06 (m, 2H), 1.85 (m, 2H), 1.64 (m, 2H), 1.49 (s, 9H), 1.45 (s, 6H), 1.36 (t, J=7.1 Hz, 3H).

EXAMPLE 90

6-Acetyl-8-cyclopentyl-2-[5-(3,3-dimethyl-piperazin-1-yl)-pyridin-2-ylamino]-5-methyl-8H-pyrido[2,3-d]pyrimidin-7-one 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,2-dimethyl-piperazine-1-carboxylic acid tert-butyl ester (0.400 g, 0.663 mmol) was dissolved in ethyl acetate (10 mL) and 6 N HCl (10 mL) and stirred at room temperature for 2 hours. The solvent was evaporated to give a yellow solid, which was dried in a vacuum oven for 5 hours at 50° C. The solid was triturated with EtOH (20 mL) and filtered to give 6-acetyl-8-cyclopentyl-2-[5-(3,3-dimethyl-piperazin-1-yl)-pyridin-2-ylamino]-5-methyl-8H-pyrido[2,3-d]pyrimidin-7-one hydrochloride salt as a yellow solid (0.120 g, 38.1%). $^1$H NMR δ (400 MHz, DMSO-$d_6$) 9.15 (s, 2H), 8.93 (s, 1H), 8.04 (d, J=3.2 Hz, 1H), 7.82 (d, J=9.1 Hz, 1H), 7.64 (m, 1H), 5.78 (m, 1H), 3.31 (m, 2H), 3.24 (m, 2H), 3.18 (s, 2H), 2.38 (s, 3H), 2.28 (s, 3H), 2.18 (m, 2H), 1.85 (m, 2H), 1.73 (m, 2H), 1.54 (m, 2H), 1.35 (s, 6H). MS (APCI)

Calc'd for M+H: 476.3. Found: 476.1. Anal. Calc'd for $C_{26}H_{33}N_7O_2$ 4.38 HCl: C, 49.16; H, 5.93; N, 15.43. Found; C, 49.55; H, 6.80; N, 14.76.

EXAMPLE 91

4-(6-Amino-pyridin-3-yl)-2,6-dimethyl-piperazine-1-carboxylic acid tert-butyl ester 5-Bromo-2-nitropyridine (10.81 g, 53.3 mmol), tetra-n-butyl ammonium iodide (0.98 g, 2.66 mmol), 2,6-dimethyl-piperazine (6.69 g, 58.6 mmol) and potassium carbonate (8.10 g, 58.6 mmol) were mixed in DMSO (50 mL). The reaction mixture was warmed to 80° C. for 4 hours by which time the reaction was complete by TLC analysis. The reaction mixture was diluted with dichloromethane and washed with water (3×75 mL). The combined organics were dried over $MgSO_4$, the inorganic salts were removed by filtration and the remaining solvents were concentrated to provide an orange solid. This solid was dissolved in dichloromethane (150 mL) to which triethylamine (10.8 g, 14.8 mL, 108 mmol) and di-tert-butyl dicarbonate (13.95 g, 63.9 mmol) were added. The reaction mixture was heated to reflux for 3 hours then cooled to room temperature and diluted with dichloromethane (100 mL) and washed with water (1×100 mL). The organic layer was then dried over $MgSO_4$, filtered and the solvent evaporated to yield an orange solid. The orange solid was dissolved in THF (500 mL) to which Raney Nickel (9.23 g) was added. The reaction mixture was shaken under a hydrogen atmosphere (50 psi) for 4 hours. The catalyst was removed by filtration, and the solvent evaporated to give a crude purple solid. This solid was purified by chromatography eluting with ethyl acetate to give 4-(6-amino-pyridin-3-yl)-2,6-dimethyl-piperazine-1-carboxylic acid tert-butyl ester as a purple solid (4.36 g, 26.7%). $^1$H NMR 5 (400 MHz, $CDCl_3$) 7.72 (d, J=2.4 Hz, 1H), 7.18 (dd, J=2.9, 8.8 Hz, 1H), 6.51 (d, J=8.8 Hz, 1H), 4.35 (s, 2H), 4.21 (m, 2H), 3.08 (dd, J=4.4, 11.7 Hz 2H), 1.48 (s, 9H), 1.35 (d, J=6.8 Hz, 6H).

EXAMPLE 92

4-[6-(6-Bromo-8-cyclopentyl-5-methyl-7-oxo-7,8-dihydro-pyrido[2,3-d]pyrimidin-2-ylamino)-pyridin-3-yl]-2,6-dimethyl-piperazine-1-carboxylic acid tert-butyl ester 6-Bromo-8-cyclopentyl-2-methanesulfinyl-5-methyl-8H-pyrido[2,3-d]pyrimidin-7-one (1.0 g, 2.70 mmol) and 4-(6-amino-pyridin-3-yl)-2,6-dimethyl-piperazine-1-carboxylic acid tert-butyl ester (1.14 g, 3.73 mmol) were heated to reflux in toluene (10 mL) for 16 hours. The reaction mixture was cooled to room temperature and the precipitate that formed was collected by filtration and washed on the funnel with toluene (3×10 mL) to give 4-[6-(6-bromo-8-cyclopentyl-5-methyl-7-oxo-7,8-dihydro-pyrido[2,3-d]pyrimidin-2-ylamino)-pyridin-3-yl]-2,6-dimethyl-piperazine-1-carboxylic acid tert-butyl ester as a dark brown-gray solid (0.620 g, 37.6%). $^1$H NMR δ (400 MHz, $CDCl_3$) 8.79 (s, 1H), 8.23 (d, J=8.8 Hz, 1H), 7.99 (d, J=2.7 Hz, 1H), 7.36 (dd, J=2.7, 8.8 Hz, 1H), 5.99 (m, 1H), 4.28 (m, 2H), 3.30 (m, 2H), 2.93 (dd, J=4.4, 11.7 Hz 2H), 2.61 (s, 3H), 2.30 (m, 2H), 2.11 (m, 2H), 1.89 (m, 2H), 1.68 (m, 2H), 1.49 (s, 9H), 1.38 (d, J=6.8 Hz, 6H).

EXAMPLE 93

6-Bromo-8-cyclopentyl-2-[5-(3,5-dimethyl-piperazin-1-yl)-pyridin-2-ylamino]-5-methyl-8H-pyrido[2,3-d]pyrimidin-7-one 4-[6-(6-Bromo-8-cyclopentyl-5-methyl-7-oxo-7,8-dihydro-pyrido[2,3-d]pyrimidin-2-ylamino)-pyridin-3-yl]-2,6-dimethyl-piperazine-1-carboxylic acid tert-butyl ester (0.051 g, 0.083 mmol) was dissolved in dichloromethane (3 mL) to which 2 N HCl (2 mL) was added and the mixture was stirred at room temperature for 2 hours. This mixture was concentrated and allowed to sit for 10 days, it was then dissolved in 2 N HCl (2 mL) and stirred at room temperature for 5 hours. The solvent was removed to give 6-bromo-8-cyclopentyl-2-[5-(3,5-dimethyl-piperazin-1-yl)-pyridin-2-ylamino]-5-methyl-8H-pyrido[2,3-d]pyrimidin-7-one hydrochloride salt as a yellow solid (0.039 g, 71.4%). $^1$H NMR δ (400 MHz, DMSO-$d_6$) 9.51 (m, 1H), 9.02 (m, 1H), 8.98 (s, 1H), 8.07 (s, 1H), 7.83 (s, 2H), 5.90 (m, 1H), 3.85 (d, J=11.2 Hz, 2H), 3.35 (m, 2H), 2.76 (dd, J=12.0, 12.0 Hz 2H), 2.58 (s, 3H), 2.14 (m, 2H), 1.92 (m, 2H), 1.77 (m, 2H), 1.58 (m, 2H), 1.28 (d, J=6.4 Hz, 6H).

EXAMPLE 94

4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,6-dimethyl-piperazine-1-carboxylic acid tert-butyl ester 4-[6-(6-Bromo-8-cyclopentyl-5-methyl-7-oxo-7,8-dihydro-pyrido[2,3-d]pyrimidin-2-ylamino)-pyridin-3-yl]-2,6-dimethyl-piperazine-1-carboxylic acid tert-butyl ester (0.450 g, 0.735 mmol), tetrakis(triphenylphosphine)palladium (0.102 g, 0.088 mmol) and tributyl-(1-ethoxy-vinyl)-stannane (0.414 g, 1.15 mmol) were dissolved in toluene (4 mL) and slowly brought to reflux for 2 hours. The solvent was evaporated and the solid redissolved in dichloromethane (8 mL). This solution was purified by silica gel chromatography to give 4-{6-[8-yclopentyl-6-(1-ethoxy-vinyl)-5-methyl-7-oxo-7,8-dihydro-pyrido[2,3-d]pyrimidin-2-ylamino]-pyridin-3-yl}-2,6-dimethyl-piperazine-1-carboxylic acid tert-butyl ester as a yellow solid (0.275 g, 61.9%).

$^1$H NMR δ (400 MHz, $CDCl_3$) 8.73 (s, 1H), 8.20 (d, J=9.0 Hz, 1H), 8.06 (s, 1H), 8.00 (d J=2.7 Hz, 1H), 7.32 (dd, J=2.7, 9.0 Hz, 1H), 5.89 (m, 1H), 4.51 (d, J=2.4 Hz, 1H), 4.26 (m, 2H), 4.17 (d, J=2.4 Hz, 1H), 3.93 (q, J=6.8 Hz, 2H), 3.28 (d, J=11.7, 2H), 2.90 (dd, J=4.2, 11.7 Hz, 1H), 2.41 (s, 3H), 2.35 (m, 2H), 2.06 (m, 2H), 1.85 (m, 2H), 1.65 (m, 2H), 1.48 (s, 9H), 1.45 (s, 6H), 1.36 (m, 9H).

EXAMPLE 95

6-Acetyl-8-cyclopentyl-2-[5-(3,5-dimethyl-piperazin-1-yl)-pyridin-2-ylamino]-5-methyl-8H-pyrido[2,3-d]pyrimidin-7-one 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,2-dimethyl-piperazine-1-carboxylic acid tert-butyl ester (0.250 g, 0.414 mmol) was dissolved in dichloromethane (3 mL) to which 2 N HCl in diethyl ether (3 mL) was added and the mixture was stirred at room temperature for 16 hours. The solvent was evaporated and the solid was dried in a vacuum oven for 24 hours at 50° C. to give 6-acetyl-8-cyclopentyl-2-[5-(3,5-dimethyl-piperazin-1-yl)-pyridin-2-ylamino]-5-methyl-8H-pyrido[2,3-d]pyrimidin-7-one hydrochloride salt as a yellow solid (0.120 g, 38.1%). $^1$H NMR δ (400 MHz, DMSO-$d_6$) 9.51 (m, 2H), 9.0 (m, 1H), 8.97 (s, 1H), 8.08 (d, J=2.7 Hz, 1H), 7.84 (dd, J=9.3 Hz, 1H), 7.78 (m, 1H), 5.80 (m, 1H), 3.35 (d, J=11.5 Hz, 2H), 3.35 (m, 2H, 2.75 (dd, J=12.2, 2H), 2.40 (s, 3H), 2.30 (s, 3H), 2.19 (m, 2H), 1.88 (m, 2H), 1.76 (m, 2H), 1.57 (m, 2H), 1.29 (d, J=6.6 Hz, 6H). MS (APCI); $M^+$+1: Calc'd, 476.3, Found 476.1. Anal. Calc'd for $C_{26}H_{33}N_7O_2$ 2.70 HCl, 0.10 $H_2O$: C, 54.23, H, 6.28, N, 17.03. Found: C, 54.60; H, 6.68; N, 16.57.

EXAMPLE 96

4-(6-Nitro-pyridin-3-yl)-morpholine

5-Bromo-2-nitropyridine (5.14 g, 25.3 mmol), tetra-n-butyl ammonium iodide (0.467 g, 1.27 mmol), morpholine (2.43 g, 27.9 mmol) and potassium carbonate (3.85 g, 27.9 mmol) were mixed in DMSO (50 mL). The reaction mixture was warmed to 80° C. for 15 hours. The reaction mixture was diluted with ethyl acetate and the solids removed by filtration. The organic filtrate was washed with water, then the solvent evaporated. The residue was then triturated with a dichloromethane/hexanes mixture to provide 4-(6-nitro-pyridin-3-yl)-morpholine as brown needles (2.90 g, 54.8%). $^1$H NMR δ (400 MHz, $CDCl_3$) 8.16 (m, 1H), 7.97 (d, J=2.9 Hz, 1H), 7.15 (dd, J=3.2, 9.3 Hz, 1H), 3.45 (m, 4H), 1.72 (m, 4H).

EXAMPLE 97

5-Morpholin-4-yl-pyridin-2-ylamine 4-(6-Nitro-pyridin-3-yl)-morpholine (2.86 g, 13.7 mmol) was dissolved in THF (100 mL) to which Raney Nickel (1.03 g) was added. The reaction mixture was shaken under a hydrogen atmosphere (50 psi) for 4 hours. The catalyst was removed by filtration and the solvent evaporated to give 5-morpholin-4-yl-pyridin-2-ylamine as a purple solid (1.91 g, 78.0%). $^1$H NMR δ (400 MHz, $CDCl_3$) 7.76 (d, J=2.0 Hz, 1H), 7.16 (dd, J=2.7, 8.8 Hz, 1H), 6.50 (d, J=8.8 Hz, 1H), 4.24 (s, 2H), 3.84 (m, 4H), 3.16 (m, 4H), 3.01 (m, 4H).

EXAMPLE 98

6-Bromo-8-cyclopentyl-5-methyl-2-(5-morpholin-4-yl-pyridin-2-ylamino)-8H-pyrido[2,3-d]pyrimidin-7-one 6-Bromo-8-cyclopentyl-2-methanesulfinyl-5-methyl-8H-pyrido[2,3-d]pyrimidin-7-one (1.0 g, 2.70 mmol) and 5-morpholin-4-yl-pyridin-2-ylamine (0.668 g, 3.73 mmol) were heated to reflux in toluene (10 mL) for 16 hours. The reaction mixture was cooled to room temperature and the precipitate that formed was collected by filtration and washed on the funnel with toluene (3×10 mL). The solid obtained was refluxed in ethyl acetate (15 mL), cooled and filtered to give 6-bromo-8-cyclopentyl-5-methyl-2-(5-morpholin-4-yl-pyridin-2-ylamino)-8H-pyrido[2,3-d]pyrimidin-7-one as a dark brown-gray solid (0.350 g, 26.7%). $^1$H NMR δ (400 MHz, $CDCl_3$) 8.78 (s, 1H), 8.17 (d, J =9.0 Hz, 1H), 8.02 (d, J=2.7 Hz, 1H), 7.97 (s, 1H), 7.32 (dd, J=2.9, 9.0 Hz, 1H), 5.99 (m, 1H), 3.89 (m, 4H), 3.16 (m, 4H), 2.61 (s, 3H), 2.30 (m, 2H), 2.10 (m, 2H), 1.88 (m, 2H), 1.68 (m, 2H).

EXAMPLE 99

8-Cyclopentyl-6-(1-ethoxy-vinyl)-5-methyl-2-(5-morpholin-4-yl-pyridin-2-ylamino)-8H-pyrido[2,3-d]pyrimidin-7-one 6-Bromo-8-cyclopentyl-5-methyl-2-(5-morpholin-4-yl-pyridin-2-ylamino)-8H-pyrido[2,3-d]pyrimidin-7-one (0.290 g, 0.597 mmol), tetrakis(triphenylphosphine)palladium (0.083 g, 0.072 mmol) and tributyl-(1-ethoxy-vinyl)-stannane (0.336 g, 0.932 mmol) were dissolved in toluene (4 mL) and slowly brought to reflux for 3 hours. The reaction mixture was purified by silica gel chromatography to give 8-cyclopentyl-6-(1-ethoxy-vinyl)-5-methyl-2-(5-morpholin-4-yl-pyridin-2-ylamino)-8H-pyrido[2,3-d]pyrimidin-7-one as a yellow solid (0.110 g, 38.6%). $^1$H NMR δ (400 MHz, DMSO-$d_6$) 8.95 (s, 1H), 8.83 (s, 1H), 8.02 (d, J=2.9 Hz, 1H), 7.86 (d, J=9.0 Hz, 1H), 7.44 (dd, J=3.2, 9.3 Hz, 1H), 5.79 (m, 1H), 4.42 (d, J=2.0 Hz, 1H), 4.01 (d, J=2.0 Hz, 1H), 3.79 (q, J=6.8 Hz, 2H), 3.72 (m, 4H), 3.09 (m, 4H), 2.34 (s, 3H), 2.17 (m, 2H), 1.85 (m, 2H), 1.71 (m, 2H), 1.55 (m, 2H), 1.21 (m, 3H).

EXAMPLE 100

6-Acetyl-8-cyclopentyl-5-methyl-2-(5-morpholin-4-yl-pyridin-2-ylamino)-8H-pyrido[2,3-d]pyrimidin-7-one 8-Cyclopentyl-6-(1-ethoxy-vinyl)-5-methyl-2-(5-morpholin-4-yl-pyridin-2-ylamino)-8H-pyrido[2,3-d]pyrimidin-7-one (0.490 g, 1.03 mmol) was dissolved in dichloromethane (5 mL). 2 N HCl in diethyl ether (3 mL) was added and the resulting mixture was stirred at room temperature for 4 hours. Then, additional 2 N HCl in diethyl ether (2 mL) was added and the mixture was stirred for an additional 12 hours. The reaction mixture was diluted with dichloromethane and aqueous $NaHCO_3$. The layers were separated and the organic layer was dried over $MgSO_4$, filtered, and the solvent evaporated to give a yellow solid. The solid was recrystallized from a mixture of hexanes, ethyl acetate and dichloromethane to give 6-acetyl-8-cyclopentyl-5-methyl-2-(5-morpholin-4-yl-pyridin-2-ylamino)-8H-pyrido[2,3-d]pyrimidin-7-one as a yellow solid (0.280 g, 60.7%). MS (APCI); $M^+$+1: Calc'd, 449.2, Found 449.2. $^1$H NMR δ (400 MHz, DMSO-$d_6$) 8.79 (s, 1H), 8.17 (d, J=9.0 Hz, 1H), 8.02 (d, J=2.7 Hz, 1H), 7.31 (dd, J=2.9, 9.0 Hz, 1H), 5.86 (m, 1H), 3.88 (m, 4H), 3.15 (m, 4H), 2.54 (s, 3H), 2.36 (s, 3H), 2.32 (m, 2H), 2.05 (m, 2H), 1.87 (m, 2H), 1.68 (m, 2H).

EXAMPLE 101

6'-Nitro-3,4,5,6-tetrahydro-2H-[1,3']bipyridinyl

5-Bromo-2-nitropyridine (5.6 g, 27.6 mmol), tetra-n-butyl ammonium iodide (0.510 g, 1.38 mmol), piperidine (2.58 g, 30.3 mmol) and potassium carbonate (3.85 g, 30.3 mmol) were mixed in DMSO (50 mL). The reaction mixture was warmed to 80° C. for 4 hours. The reaction mixture was diluted with ethyl acetate and filtered. The volume was reduced to remove ethyl acetate, the remaining solution was diluted with water (50 mL). A precipitate immediately formed and was collected by filtration and washed on the funnel with water to provide 6'-nitro-3,4,5,6-tetrahydro-2H-[1,3']bipyridinyl as an orange—brown solid (4.90 g, 85.7

%). $^1$H NMR δ (400 MHz, $CDCl_3$) 7.76 (s, 1H), 7.15 (d, J=7.3 Hz, 1H), 6.49 (d, J=8.5 Hz, 1H), 3.84 (m, 5H), 3.00 (m, 4H), 2.60 (s, 1H).

EXAMPLE 102

3,4,5,6-Tetrahydro-2H-[1.3']bipyridinyl-6'-ylamine

6'-Nitro-3,4,5,6-tetrahydro-2H-[1,3']bipyridinyl (4.69 g, 22.6 mmol) was dissolved in THF (100 mL) to which Raney Nickel (1.08 g) was added. The reaction was shaken under a hydrogen atmosphere (50 psi) for 4 hours. The catalyst was removed by filtration and the solvent evaporated to give 3,4,5,6-tetrahydro-2H-[1,3']bipyridinyl-6'-ylamine as a purple solid (4.86 g, 85.7%). $^1$ H NMR δ (400 MHz, $CDCl_3$) 7.76 (d, J=2.4 Hz, 1H), 7.19 (dd, J=2.9, 8.8 Hz, 1H), 6.47 (dd, J=0.7, 8.8 Hz, 1H), 4.18 (s, 2H), 2.97 (m, 4H), 1.71 (m, 4H), 1.53 (m, 2H).

EXAMPLE 103

6-Bromo-8-cyclopentyl-5-methyl-2-(3,4,5,6-tetrahydro-2H-[1,3]bipyridinyl-6'-ylamino)-8H-pyrido[2,3-d]pyrimidin-7-one 6-Bromo-8-cyclopentyl-2-methanesulfinyl-5-methyl-8H-pyrido[2,3-d]pyrimidin-7-one (1.0 g, 2.70 mmol) and 3,4,5,6-tetrahydro-2H-[1,3']bipyridinyl-6'-ylamine (0.668 g, 3.73 mmol) were heated to reflux in toluene (10 mL) for 16 hours. The reaction mixture was cooled to room temperature and the precipitate that formed was collected by filtration and washed on the funnel with toluene (3×10 mL) to give 6-bromo-8-cyclopentyl-5-methyl-2-(3,4,5,6-tetrahydro-2H-[1,3']bipyridinyl-6'-ylamino)-8H-pyrido[2,3-d]pyrimidin-7-one as a brown solid (0.358 g, 27.3%). $^1$H NMR δ (400 MHz, $CDCl_3$) 8.79 (s, 1H), 8.27 (s, 1H), 8.17 (d, J=9.0 Hz, 1H), 8.01 (s, 1H), 7.38 (d, J=6.8 Hz, 1H), 5.98 (m, 1H), 3.1 (m, 4H), 2.60 (s, 3H), 2.30 (m, 2H), 2.11 (m, 2H), 1.88 (m, 2H), 1.57-1.75 (m, 8H).

EXAMPLE 104

8-Cyclopentyl-6-(1-ethoxy-vinyl)-5-methyl-2-(3,4,5,6-tetrahydro-2H-[1,3']bipyridinyl-6'-ylamino)-8H-pyrido[2,3-d]pyrimidin-7-one 6-Bromo-8-cyclopentyl-5-methyl-2-(5-morpholin-4-yl-pyridin-2-ylamino)-8H-pyrido[2,3-d]pyrimidin-7-one (0.310 g, 0.641 mmol), tetrakis(triphenylphosphine)palladium (0.089 g, 0.077 mmol) and tributyl-(1-ethoxy-vinyl)-stannane (0.361 g, 1.0 mmol) were dissolved in toluene (3 mL) and slowly brought to reflux for 2 hours. The reaction mixture was allowed to cool, then purified by silica gel chromatography to give 8-cyclopentyl-6-(1-ethoxy-vinyl)-5-methyl-2-(3,4,5,6-tetrahydro-2H-[1,3']bipyridinyl-6'-ylamino)-8H-pyrido[2,3-d]pyrimidin-7-one as a yellow solid (0.180 mg, 59.2%). $^1$H NMR δvvv (400 MHz, $CDCl_3$) 8.73 (s, 1H), 8.16 (d, J=9.0 Hz, 1H), 8.05 (s, 1H), 8.01 (d, J=2.9 Hz, 1H), 7.36 (dd, J=2.9, 9.3 Hz, 1H), 5.90 (m, 1H), 4.52 (d, J=2.4 Hz, 1H), 4.18 (d, J=2.2 Hz, 1H), 3.93 (q, J=7.1 Hz, 2H), 3.14 (m, 4H), 2.41 (s, 3H), 2.36 (m, 2H), 2.06 (m, 2H), 1.84 (m, 2H), 1.56-1.77 (m, 8H), 1.21 (t, J=7.1 Hz, 3H).

EXAMPLE 105

6-Acetyl-8-cyclopentyl-5-methyl-2-(3,4,5,6-tetrahydro-2H-[1,3']bipyridinyl-6'-ylamino)-8H-pyrido[2,3-d]pyrimidin-7-one 8-Cyclopentyl-6-(1-ethoxy-vinyl)-5-methyl-2-(3,4,5,6-tetrahydro-2H-[1,3']bipyridinyl-6'-ylamino)-8H-pyrido[2,3-d]pyrimidin-7-one (0.180 g, 0.379 mmol) was dissolved in ethyl acetate (10 mL) and 6 N HCl (10 mL) was added then the mixture was stirred at room temperature for 2 hours. The mixture was diluted with dichloromethane and aqueous $NaHCO_3$. The layers were separated and the organic layer was dried over $MgSO_4$, filtered, and the solvent evaporated to give 6-acetyl-8-cyclopentyl-5-methyl-2-(3,4,5,6-tetrahydro-2H-[1,3']bipyridinyl-6'-ylamino)-8H-pyrido[2,3-d] pyrimidin-7-one as a yellow solid (0.120 g, 71.0%). $^1$H NMR δ (400 MHz, $CDCl_3$) 8.78 (s, 1H), 8.20 (d, J=8.5 Hz, 1H), 7.95 (s, 1H), 7.39 (m, 1H), 5.85 (m, 1H), 3.15 (m, 4H), 2.53 (s, 3H), 2.36 (s, 3H), 2.33 (m, 2H), 2.05 (m, 2H), 1.87 (m, 2H), 1.77-1.56 (m, 8H). MS (APCI); $M^+$+1: Calc'd, 447.2, Found 447.2. Anal. Calc'd for $C_{25}H_{30}N_6O_2$ 0.35 $H_2O$: C, 66.31; H, 6.83; N, 18.56. Found: C, 66.68; H, 6.76; N, 18.07.

EXAMPLE 106

8-Cyclopentyl-(2-ethoxy-ethyl)-2-methylsulfanyl-8H-pyrido[2,3-d]pyrimidin-7-one

To a cooled (−78° C.) solution of 4-ethoxy-butyric acid ethyl ester (9.85 g, 61.47 mmol) in THF (25 ml) was added lithium bis(trimethylsilyl)amide (77.0 ml, 76.85 mmol, 1 M solution in THF). The reaction mixture was stirred for 10 minutes to form the anion. 4-Cyclopentylamino-2-methylsulfanyl-pyrimidine-5-carbaldehyde was then added and the reaction allowed to warm to RT and stirred overnight. The reaction mixture was quenched with 10% aqueous HCl (100 ml). The aqueous layer was extracted with ethylacetate (150 ml total) and the organic layers were combined and concentrated to give a yellow oil. Chromatographic purification on silica gel (chloroform/ethyl acetate gradient) gave 8-cyclopentyl-6-(2-ethoxy-ethyl)-2-methylsulfanyl-8H-pyrido[2,3-d]pyrimidin-7-one (3.22 g, 9.65 mmol). MS (APCI+) 334 (M+1, 100); $^1$H NMR δ (400 MHz, DMSO-$_{d6}$) 8.54 (s, 1H), 7.47-7.46 (m, 1H), 5.99-5.90 (m, 1H), 3.69 (t, J=6.25 Hz, 2H), 3.49 (q, J=7.03 Hz, 2H), 2.84 (t, J=6.25 Hz, 2H), 2.59 (s, 3H), 2.34-2.29 (m, 2H), 2.08-2.02 (m, 2H), 1.88-1.83 (m, 2H), 1.69-1.65 (m, 3H), 1.17 (t, J=7.04 Hz, 3H).

EXAMPLE 107

4-{6-[8-Cyclopentyl-6-(2-ethoxy-ethyl)-7-oxo-7,8-dihydro-pyrido[2,3-d]pyrimidin-2-ylamino]-pyridin-3-yl}-piperazine-1-carboxylic acid tert-butyl ester 8-Cyclopentyl-6-(2-ethoxy-ethyl)-2-methanesulfinyl-8H-pyrido[2,3-d]pyrimidin-7-one (1.0 g, 2.86 mmol) and 4-(6-amino-pyridin-3-yl)-piperazine-1-carboxylic acid tert-butyl ester (1.10 g, 3.95 mmol) were heated to reflux in toluene (10 mL) for 16 hours. The mixture was cooled to room temperature and purified by silica gel chromatography to give 4-{6-[8-cyclopentyl-6-(2-ethoxy-ethyl)-7-oxo-7,8-dihydro-pyrido[2,3-d]pyrimidin-2amino]-pyridin-3-yl}-piperazine-1-carboxylic acid tert-butyl ester as an orange solid (0.328 g, 20.4%). $^1$H NMR δ (400 MHz, $CDCl_3$) 8.54 (s, 1H), 8.26 (d, J=9.0 Hz, 1H), 7.98 (d, J=2.9 Hz, 1H), 7.45 (s, 1H), 7.38 (dd, J=2.9, 9.3 Hz, 1H), 5.90 (m, 1H), 3.70 (t, J=6.3, 1H), 3.61 (m, 4H), 3.51 (q, J=7.1, 1H), 3.11 (m, 4H), 2.84 (t, J=5.9, 1H), 2.33 (m, 2H), 2.08 (m, 2H), 1.87 (m, 2H), 1.69 (m, 2H), 1.48 (s, 9H), 1.19 (t, J=7.1, 1H).

EXAMPLE 108

8-Cyclopentyl-6-(2-ethoxy-ethyl)-2-(5-piperazin-1-yl-pyridin-2-ylamino)-8H-pyrido[2,3-d]pyrimidin-7-one 4-{6-[8-Cyclopentyl-6-(2-ethoxy-ethyl)-7-oxo-7,8-dihydro-pyrido[2,3-d]pyrimidin-2-ylamino]-pyridin-3-yl}-piperazine-1-carboxylic acid tert-butyl ester (0.325 g, 0.577 mmol) was dissolved in dichloromethane (4 mL). 2 N HCl in diethyl ether (4 mL) was added and the mixture was stirred at room temperature for 18 hours. The solvent was evaporated to give 8-cyclopentyl-6-(2-ethoxy-ethyl)-2-(5-piperazin-1-yl-pyridin-2-ylamino)-8H-pyrido[2,3-d]pyrimidin-7-one hydrochloride salt as a yellow solid (0.292 g, 97.7%). MS (APCI) Calc'd for M+H: 449.2. Found: 449.2. Anal. Calc'd for $C_{25}H_{33}N_7O_2$ 2.6 HCl, 0.35 $H_2O$: C, 52.26; H, 6.56; N, 16.88. Found: C, 52.01; H, 6.96; N, 16.88.

EXAMPLE 109

8-Cyclopentyl-6-(2-methoxy-ethoxymethyl)-2-methylsulfanyl-8H-pyrido[2,3-d]pyrimidin-7-one 6-Bromomethyl-8-cyclopentyl-2-methylsulfanyl-8H-pyrido[2,3-d]pyrimidin-7-one (1.33 g, 3.75 mmol) was dissolved in 2-methoxyethanol (10 mL) to which potassium carbonate (0.778 g, 5.63 mmol) was added and the mixture was stirred at room temperature for 2 hours. The reaction mixture was then filtered and the salts washed with ethyl acetate. The combined organics were evaporated to give 8-cyclopentyl-6-(2-methoxy-ethoxymethyl)-2-methylsulfanyl-8H-pyrido[2,3-d]pyrimidin-7-one as a waxy solid (1.00 g, 76.3%). $^1$H NMR δ (400 MHz, $CDCl_3$) 8.60 (s, 1H), 7.71 (t, J=1.6 Hz, 1H), 5.95 (m, 1H), 4.52 (d, J=1.6 Hz, 1H), 3.76 (m, 2H), 3.63 (m, 2H), 3.41 (s, 3H), 2.60 (s, 3H), 2.32 (m, 2H), 2.06 (m, 2H), 1.87 (m, 2H), 1.68 (m, 2H).

EXAMPLE 110

8-Cyclopentyl-2-methanesulfinyl-6-(2-methoxy-ethoxymethyl)-8H-pyrido[2,3-d]pyrimidin-7-one 8-Cyclopentyl-6-(2-methoxy-ethoxymethyl)-2-methylsulfanyl-8H-pyrido[2,3-d]pyrimidin-7-one (1.46 g, 4.18 mmol) and 2-benzenesulfonyl-3-phenyl-oxaziridine (1.31 g, 5.01 mmol) were dissolved in dichloromethane (10 mL) and stirred at ambient temperature for 12 hours. The reaction mixture was then purified by silica gel chromatography to give 8-cyclopentyl-2-methanesulfinyl-6-(2-methoxy-ethoxymethyl)-8H-pyrido[2,3-d]pyrimidin-7-one as a white waxy solid (0.60 g, 39.3%). $^1$H NMR δ (400 MHz, $CDCl_3$) 8.94 (s, 1H), 7.88 (t, J=1.7 Hz, 1H), 5.95 (m, 1H), 4.52 (d, J=1.7 Hz, 1H), 3.80 (m, 2H), 3.65 (m, 2H), 3.43 (s, 3H), 2.98 (s, 3H), 2.25 (m, 2H), 2.13 (m, 2H), 1.94 (m, 2H), 1.70 (m, 2H).

EXAMPLE 111

4-{6-[8-Cyclopentyl-6-(2-methoxy-ethoxymethyl)-7-oxo-7,8-dihydro-pyrido[2,3-d]pyrimidin-2-ylamino]-pyridin-3-yl}-pipierazine-1-carboxylic acid tert-butyl ester 8-Cyclopentyl-2-methanesulfinyl-6-(2-methoxy-ethoxymethyl)-8H-pyrido[2,3-d]pyrimidin-7-one (1.0 g, 2.86 mmol) and 4-(6-amino-pyridin-3-yl)-piperazine-1-carboxylic acid tert-butyl ester (1.10 g, 3.95 mmol) were heated to reflux in toluene (10 mL) for 16 hours. The reaction mixture was cooled to room temperature and purified by silica gel chromatography to give 4-{6-[8-cyclopentyl-6-(2-methoxy-ethoxymethyl)-7-oxo-7,8-dihydro-pyrido[2,3-d]pyrimidin-2-ylamino]-pyridin-3-yl}-piperazine-1-carboxylic acid tert-butyl ester as a yellow solid (0.140 g, 14.7%). $^1$H NMR δ (400 MHz, $CDCl_3$) 8.60 (s, 1H), 8.34 (m, 1H), 7.95 (s, 1H), 7.69 (t, J=1.4 Hz, 1H), 7.42 (m, 1H), 5.91 (m, 1H), 4.53 (d, J=1.2 Hz, 1H), 3.78 (m, 1H), 3.63 (m, 6H), 3.43 (s, 3H), 3.11 (m, 4H), 2.35 (m, 2H), 2.08 (m, 2H), 1.88 (m, 2H), 1.69 (m, 2H), 1.48 (s, 9H).

EXAMPLE 112

8-Cyclopentyl-6-(2-methoxy-ethoxymethyl)-2-(5-piperazin-1-yl-pyridin-2-ylamino)-8H-pyrido[2,3-d]pyrimidin-7-one 4-{6-[8-Cyclopentyl-6-(2-methoxy-ethoxymethyl)-7-oxo-7,8-dihydro-pyrido[2,3-d]pyrimidin-2-ylamino]-pyridin-3-yl}-piperazine-1-carboxylic acid tert-butyl ester (0.140 g, 0.242 mmol) was dissolved in dichloromethane (2 mL). 2 N HCl in diethyl ether (2 mL) was added and the reaction mixture was stirred at room temperature for 18 hours. The solvent was evaporated to give 8-cyclopentyl-6-(2-methoxy-ethoxymethyl)-2-(5-piperazin-1-yl-pyridin-2-ylamino)-8H-pyrido[2,3-d]pyrimidin-7-one hydrochloride salt as a yellow solid (0.116 g, 85.9%). MS (APCI); $M^+$+1: Calc'd, 480.3, Found 480.2. Anal. Calc'd for $C_{25}H_{33}N_7O_2$ 2.16 HCl: C, 53.78; H, 6.35; N, 17.56. Found; C, 54.03; H, 6.64; N, 17.17.

EXAMPLE 113

8-Cyclopentyl-6-ethoxymethyl-2-methylsulfanyl-8H-pyrido[2,3-d]pyrimidin-7-one

3-Ethoxy-propionic acid ethyl ester (12.31 g, 84.2 mmol) was dissolved in tetrahydrofuran (40 mL) to which LiHMDS (89 mL, 88.9 mmol, 1.0 M in THF) was slowly added. 4-Cyclopentylamino-2-methylsulfanyl-pyrimidine-5-carbaldehyde (10.0 g, 42.2 mmol) was then added neat and the reaction mixture was stirred at ambient temperature for 17 hours then brought to reflux for 7 hours. The reaction mixture was diluted with ethyl acetate and water, the layers separated, the organic layer dried over $MgSO_4$ and the solvent evaporated to give a crude oil. The crude product was dissolved in ethyl acetate and diluted with hexanes to give a precipitate, which was collected by filtration to give 8-cyclopentyl-6-ethoxymethyl-2-methylsulfanyl-8H-pyrido[2,3-d]pyrimidin-7-one as an off-white solid (4.70 g, 34.9%). $^1$H NMR δ (400 MHz, $CDCl_3$) 8.47 (s, 1H), 7.52 (t, J=1.5 Hz, 1H), 5.82 (m, 1H), 4.32 (d, J=1.7 Hz, 1H), 3.53 (q, J=7.1 Hz, 2H), 2.47 (s, 3H), 2.17 (m, 2H), 1.93 (m, 2H), 1.73 (m, 2H), 1.54 (m, 2H), 1.15 (t, J=7.1 Hz, 3H).

EXAMPLE 114

8-Cyclopentyl-6-ethoxymethyl-2-methanesulfinyl-8H-pyrido[2,3-d]pyrimidin-7-one

8-Cyclopentyl -6-ethoxymethyl-2-methylsulfanyl-8H-pyrido[2,3-d]pyrimidin-7-one (4.60 g, 14.40 mmol) and 2-benzenesulfonyl-3-phenyl-oxaziridine (4.89 g, 18.72 mmol) were dissolved in dichloromethane (30 mL) and stirred at ambient temperature for 12 hours. The crude product was then purified by silica gel chromatography to give 8-cyclopentyl-6-ethoxymethyl-2-methanesulfinyl-8H-pyrido[2,3-d]pyrimidin-7-one as a white waxy solid (2.67 g, 55.3%). $^1$H NMR δ (400 MHz, $CDCl_3$) 8.94 (s, 1H), 7.81 (t, J=1.7 Hz, 1H), 5.98 (m, 1H), 4.50 (d, J=1.7 Hz, 1H), 3.68 (q, J=7.1 Hz, 2H), 2.96 (s, 3H), 2.22 (m, 2H), 2.12 (m, 2H), 1.94 (m, 2H), 1.69 (m, 2H), 1.31 (t, J=7.1 Hz, 3H).

EXAMPLE 115

4-[6-(8-Cyclopentyl-6-ethoxymethyl-7-oxo-7,8-dihydro-pyrido[2,3-d]pyrimidin-2-ylamino)-pyridin-3-yl]-piperazine-1-carboxylic acid tert-butyl ester 8-Cyclopentyl-6-ethoxymethyl-2-methanesulfinyl-8H-pyrido[2,3-d]pyrimidin-7-one (1.0 g, 2.86 mmol) and 4-(6-amino-pyridin-3-yl)-piperazine-1-carboxylic acid tert-butyl ester (1.10 g, 3.95 mmol) were heated to reflux in toluene (10 mL) for 16 hours. The reaction mixture was cooled to room temperature and purified by silica gel chromatography to give 4-[6-(8-cyclopentyl-6-ethoxymethyl-7-oxo-7,8-dihydro-pyrido[2,3-d]pyrimidin-2-ylamino)-pyridin-3-yl]-piperazine-1-carboxylic acid tert-butyl ester as a yellow solid (0.140 g, 14.7%). $^1$H NMR δ (400 MHz, $CDCl_3$) 8.59 (s, 1H), 8.26 (d, J=9.3 Hz, 1H), 7.97 (d, J=2.7 Hz, 1H), 7.6 (t, J=1.5 Hz, 1H), 7.38 (dd, J=2.7, 9.0 Hz, 1H), 5.89 (m, 1H), 4.55 (d, J=1.2 Hz, 1H), 3.66 (q, J=7.1 Hz, 2H), 3.60 (m, 4H), 3.11 (m, 4H), 2.34 (m, 2H), 2.07 (m, 2H), 1.88 (m, 2H), 1.69 (m, 2H), 1.48 (s, 9H), 1.30 (t, J=6.8 Hz, 3H).

EXAMPLE 116

8-Cyclopentyl-6-ethoxymethyl-2-(5-piperazin-1-yl-pyridin-2-ylamino)-8H-pyrido[2,3-d]pyrimidin-7-one 4-{6-[8-Cyclopentyl-6-(2-methoxy-ethoxymethyl)-7-oxo-7,8-dihydro-pyrido[2,3-d]pyrimidin-2-ylamino]-pyridin-3-yl}-piperazine-1-carboxylic acid tert-butyl ester (0.140 g, 0.242 mmol) was dissolved in dichloromethane (2 mL). 2 N HCl in diethyl ether (2 mL) was added and the reaction mixture was stirred at room temperature for 18 hours. The solvent was evaporated to give 8-cyclopentyl-6-(2-methoxy-ethoxymethyl)-2-(5-piperazin-1-yl-pyridin-2-ylamino)-8H-pyrido[2,3-d]pyrimidin-7-one as a yellow solid (0.116 g, 85.9%). MS (APCI) Calc'd for M+1: 450.3. Found: 450.1. $^1$H NMR δ (400 MHz, DMSO-$d_6$) 9.12 (s, 2H), 8.34 (s, 1H), 8.01 (d, J=2.7 Hz, 1H), 7.86 (s, 1H), 7.83 (s, 1H), 7.76 (d, J=9.5 Hz, 1H), 5.84 (m, 1H), 4.32 (d, J=1.2 Hz, 1H), 3.57 (q, J=6.8 Hz, 2H), 3.38 (m, 4H), 3.23 (m, 4H), 2.26 (m, 2H), 1.89 (m, 2H), 1.75 (m, 2H), 1.58 (m, 2H), 1.19 (t, J=6.8 Hz, 3H).

EXAMPLE 117

8-Cyclopentyl-6-methoxymethyl-2-methylsulfanyl-8H-pyrido[2,3-d]pyrimidin-7-one

3-Methoxy-propionic acid methyl ester (9.95 g, 84.2 mmol) was dissolved in tetrahydrofuran (40 mL) to which LiHMDS (89 mL, 88.9 mmol, 1.0 M in THF) was slowly added. 4-Cyclopentylamino-2-methylsulfanyl-pyrimidine-5-carbaldehyde (10.0 g, 42.2 mmol) was then added neat and the reaction mixture brought to reflux for 7 days. The reaction mixture was diluted with ethyl acetate and water, the layers separated, the organic layer dried over $MgSO_4$ and the solvent evaporated to give a crude oil. The crude product was dissolved in ethyl acetate and diluted with hexanes to give a precipitate which was collected by filtration to give 8-cyclopentyl-6-methoxymethyl-2-methylsulfanyl-8H-pyrido[2,3-d]pyrimidin-7-one as an off-white solid (3.11 g, 24.1%). $^1$H NMR δ (400 MHz, $CDCl_3$) 8.46 (s, 1H), 7.49 (t, J=1.7 Hz, 1H), 5.81 (m, 1H), 4.28 (d, J=1.7 Hz, 1H), 3.37 (s, 3H), 2.47 (s, 3H), 2.18 (m, 2H), 1.93 (m, 2H), 1.73 (m, 2H), 1.55 (m, 2H).

EXAMPLE 118

8-Cyclopentyl-2-methanesulfinyl-6-methoxymethyl-8H-pyrido[2,3-d]pyrimidin-7-one

8-Cyclopentyl-6-methoxymethyl-2-methylsulfanyl-8H-pyrido[2,3-d]pyrimidin-7-one (4.44 g, 14.54 mmol) and 2-benzenesulfonyl-3-phenyl-oxaziridine (4.94 g, 18.90 mmol) were dissolved in dichloromethane (100 mL) and stirred at ambient temperature for 12 hours. The solvent volume was reduced to approximately 50 mL and was then purified by silica gel chromatography to give 8-cyclopentyl-2-methanesulfinyl-6-methoxymethyl-8H-pyrido[2,3-d]pyrimidin-7-one as an off—white solid (2.51 g, 53.7%). $^1$H NMR δ (400 MHz, $CDCl_3$) 8.93 (s, 1H), 7.78 (t, J=1.7 Hz, 1H), 5.99 (m, 1H), 4.46 (d, J=1.7 Hz, 1H), 3.53 (s, 3H), 2.96 (s, 3H), 2.23 (m, 2H), 2.12 (m, 2H), 1.93 (m, 2H), 1.69 (m, 2H).

EXAMPLE 119

4-[6-(8-Cyclopentyl-6-methoxymethyl-7-oxo-7,8-dihydro-pyrido[2,3-d]pyrimidin-2-ylamino)-pyridin-3-yl]-piperazine-1-carboxylic acid tert-butyl ester 8-Cyclopentyl-2-methanesulfiny-6-methoxymethyl-8H-pyrido[2,3-d]pyrimidin-7-one (2.5 g, 7.78 mmol) and 4-(6-amino-pyridin-3-yl)-piperazine-1-carboxylic acid tert-butyl ester (2.99 g, 10.73 mmol) were heated to reflux in toluene (25 mL) for 16 hours. The reaction mixture was cooled to room temperature and purified by silica gel chromatography to give 4-[6-(8-cyclopentyl-6-methoxymethyl-7-oxo-7,8-dihydro-pyrido[2,3-d]pyrimidin-2-ylamino)-pyridin-3-yl]-piperazine-1-carboxylic acid tert-butyl ester as a yellow solid (1.24 g, 30.5%). $^1$H NMR δ (400 MHz, $CDCl_3$) 8.59 (s, 1H), 8.26 (d, J=9.3 Hz, 1H), 7.97 (d, J=2.7 Hz, 1H), 7.6 (t, J=1.5 Hz, 1H), 7.38 (dd, J=2.7, 9.0 Hz, 1H), 5.89 (m, 1H), 4.55 (d, J=1.2 Hz, 1H), 3.66 (q, J=7.1 Hz, 2H), 3.60 (m, 4H), 3.11 (m, 4H), 2.34 (m, 2H), 2.07 (m, 2H), 1.88 (m, 2H), 1.69 (m, 2H), 1.48 (s, 9H), 1.30 (t, J=6.8 Hz, 3H).

EXAMPLE 120

8-Cyclopentyl-6-methoxymethyl-2-(5-piperazin-1-yl-pyridin-2-ylamino)-8H-pyrido[2,3-d]pyrimidin-7-one 4-{6-[8-Cyclopentyl-6-(2-methoxy-ethoxymethyl)-7-oxo-7,8-dihydro-pyrido[2,3-d]pyrimidin-2-ylamino]-pyridin-3-yl}-piperazine-1-carboxylic acid tert-butyl ester (0.110 g, 0.205 mmol) was dissolved in dichloromethane (2 mL). 2 N HCl in diethyl ether (2 mL) was added and the reaction mixture was stirred at room temperature for 18 hours. The solvent was evaporated to give 8-cyclopentyl-6-(2-methoxy-ethoxymethyl)-2-(5-piperazin-1-yl-pyridin-2-ylamino)-8H-pyrido[2,3-d]pyrimidin-7-one hydrochloride salt as a yellow solid (0.096 g, 92.1%). MS (APCI) Calc'd for M+1: 450.3. Found: 450.1. $^1$H NMR 6 (400 MHz, DMSO-$d_6$) 9.12 (s, 2H), 8.34 (s, 1H), 8.01 (d, J=2.7 Hz, 1H), 7.86 (s, 1H), 7.83 (s, 1H), 7.76 (d, J=9.5 Hz, 1H), 5.84 (m, 1H), 4.32 (d, J=1.2 Hz, 1H), 3.57 (q, J=6.8 Hz, 2H), 3.38 (m, 4H), 3.23 (m, 4H), 2.26 (m, 2H), 1.89 (m, 2H), 1.75 (m, 2H), 1.58 (m, 2H), 1.19 (t, J=6.8 Hz, 3H).

EXAMPLE 121

2,6-Dimethyl-4-(6-nitro-pyridin-3-yl)-morpholine

5-Bromo-2-nitropyridine (4.84 g, 23.84 mmol), tetra-n-butyl ammonium iodide (0.440 g, 1.19 mmol), 2,6-dimethyl-morpholine (3.02 g, 26.22 mmol) and potassium carbonate (3.62 g, 26.22 mmol) were mixed in DMSO (45 mL). The reaction mixture was warmed to 80° C. for 6 hours. The reaction mixture was diluted with ethyl acetate and filtered. The volume of the filtrate was reduced to remove ethyl acetate, and the remaining solution was diluted with water (50 mL). A precipitate immediately formed and was collected by filtration then washed on the funnel with water to provide 2,6-dimethyl-4-(6-nitro-pyridin-3-yl)-morpholine as an orange solid (4.39 g, 78.0%). $^1$H NMR δ (400 MHz, $CDCl_3$) 8.16 (d, J=9.0 Hz, 1H), 8.11 (d, J=2.9 Hz, 1H), 7.19 (dd, J=2.9, 9.3 Hz, 1H), 3.77 (m, 2H), 3.65 (dd, J=2.2, 12.9 Hz, 2H), 2.66 (dd, J=10.7, 12.5 Hz, 2H), 1.29 (d, J=6.4 Hz, 6H).

EXAMPLE 122

5-(2,6-Dimethyl-morpholin-4-yl)-pyridin-2-ylamine 2,6-Dimethyl-4-(6-nitro-pyridin-3-yl)-morpholine (4.00 g, 16.86 mmol) was dissolved in THF (100 mL) to which Raney Nickel (3.10 g) was added. The reaction mixture was shaken under a hydrogen atmosphere (50 psi) for 4 hours. The catalyst was filtered and the solvent evaporated to give 5-(2,6-dimethyl-morpholin-4-yl)-pyridin-2-ylamine as a purple solid (3.05 g, 87.4%). $^1$H NMR δ (400 MHz, $CDCl_3$) 7.74 (d, J=2.4 Hz, 1H), 7.16 (dd, J=2.9, 8.8 Hz, 1H), 6.49 (dd, J=0.7, 8.8 Hz, 1H), 3.79 (m, 2H), 2.34 (dd, J=10.5, 10.5, 2H), 1.22 (d, J=6.3 Hz, 6H).

EXAMPLE 123

6-Bromo-8-cyclopentyl-2-[5-(2,6-dimethyl-morpholin-4-yl)-pyridin-2-ylamino]-5-methyl-8H-pyrido[2,3-d]pyrimidin-7-one 6-Bromo-8-cyclopentyl-2-methanesulfinyl-5-methyl-8H-pyrido[2,3-d]pyrimidin-7-one (1.0 g, 2.70 mmol) and 5-(2,6-dimethyl-morpholin-4-yl)-pyridin-2-ylamine (0.668 g, 3.73 mmol) were heated to reflux in toluene (10 mL) for 16 hours. The reaction mixture was cooled to room temperature and the precipitate that formed was collected by filtration and washed on the funnel with toluene (3×10 mL) to give 6-bromo-8-cyclopentyl-2-[5-(2,6-dimethyl-morpholin-4-yl)-pyridin-2-ylamino]-5-methyl-8H-pyrido[2,3-d]pyrimidin-7-one as a brown solid (0.358 g, 27.3%). MS (APCI) Calc'd for M+1: 513.2. Found: 513.1. Anal. Calc'd for $C_{24}H_{29}BrN_6O_2$: C, 56.14; H, 5.69; N, 16.37. Found; C, 55.90; H, 5.62; N, 16.10.

EXAMPLE 124

8-Cyclopentyl-6-ethoxymethyl-2-(3,4,5,6-tetrahydro-2H-[1,3]bipyridinyl-6'-ylamino)-8H-pyrido[2,3-d]pyrimidin-7-one 8-Cyclopentyl-6-ethoxymethyl-2-methanesulfinyl-8H-pyrido[2,3-d]pyrimidin-7-one (0.60 g, 1.79 mmol) and 3,4,5,6-tetrahydro-2H-[1,3']bipyridinyl-6'-ylamine (0.438 g, 2.47 mmol) were heated to reflux in toluene (6 mL) for 16 hours. The reaction mixture was cooled to room temperature and the precipitate that formed was filtered off and washed with toluene (2×4 mL) to give 8-cyclopentyl-6-ethoxymethyl-2-(3,4,5,6-tetrahydro-2H-[1,3']bipyridinyl-6'-ylamino)-8H-pyrido[2,3-d]pyrimidin-7-one (0.122 g, 15.2%). MS (APCI) Calc'd for M+1: 449.3. Found: 449.3. Anal. Calc'd for $C_{25}H_{32}N_6O_2$: C, 66.94; H, 7.19; N, 18.74. Found: C, 66.72; H, 7.13; N, 18.57.

EXAMPLE 125

8-Cyclopentyl-6-ethoxymethyl-2-(5-morpholin-4-yl-pyridin-2-ylamino)-8H-pyrido[2,3-d]pyrimidin-7-one 8-Cyclopentyl-6-ethoxymethyl-2-methanesulfinyl-8H-pyrido[2,3-d]pyrimidin-7-one (0.60 g, 1.79 mmol) and 5-morpholin-4-yl-pyridin-2-ylamine (0.442 g, 2.47 mmol) were heated to reflux in toluene (6 mL) for 16 hours. The reaction mixture was cooled to room temperature and the precipitate that formed was filtered off and washed with toluene (2×4 mL) to give 8-cyclopentyl-6-ethoxymethyl-2-(5-morpholin-4-yl-pyridin-2-ylamino)-8H-pyrido[2,3-d]pyrimidin-7-one (0.142 g, 17.6%). MS (APCI); $M^+$+1: Calc'd, 451.3, Found 451.3. Anal. Calc'd for $C_{25}H_{32}N_6O_2$: C, 63.98; H, 6.71; N, 18.65. Found; C, 64.03; H, 6.66; N, 18.49.

EXAMPLE 126

(8-Cyclopentyl-2-methylsulfanyl-7-oxo-7,8-dihydro-pyrido[2,3-d]pyrimidin-6-ylmethyl)-carbamic acid benzyl ester 3-Benzyloxycarbonylamino-propionic acid ethyl ester (6.68 g, 26.58 mmol) was dissolved in tetrahydrofuran (40 mL) to which LiHMDS (28 mL, 28 mmol, 1.0 M in THF) was slowly added. 4-Cyclopentylamino-2-methylsulfanyl-pyrimidine-5-carbaldehyde (3.15 g, 13.29 mmol) was then added neat and the reaction mixture was brought to reflux for 7 hours. The reaction mixture was diluted with ethyl acetate and water, the layers separated, the organic layer dried over $MgSO_4$ and the solvent evaporated to give a crude oil. The crude oil was purified by silica gel chromatography to give (8-cyclopentyl-2-methylsulfanyl-7-oxo-7,8-dihydro-pyrido[2,3-d]pyrimidin-6-ylmethyl)-carbamic acid benzyl ester as pale yellow waxy solid (1.67 g, 29.6%). $^1$H NMR δ (400 MHz, $CDCl_3$) 8.57 (s, 1H), 7.56 (s, 1H), 7.26-7.36 (m, 5H), 5.93 (m, 1H), 5.56 (t, J=6.1 Hz, 1H), 5.08 (s, 2H), 4.25 (d, J=6.2 Hz, 2H), 2.60 (s, 3H), 2.30 (m, 2H), 2.05 (m, 2H), 1.86 (m, 2H), 1.69 (m, 2H).

EXAMPLE 127

(8-Cyclopentyl-2-methanesulfinyl-7-oxo-7,8-dihydro-pyrido[2,3-d]pyrimidin-6-ylmethyl)-carbamic acid benzyl ester (8-Cyclopentyl-2-methylsulfanyl-7-oxo-7,8-dihydro-pyrido[2,3-d]pyrimidin-6-ylmethyl)-carbamic acid benzyl ester (1.67 g, 3.93 mmol) and 2-benzenesulfonyl-3-phenyl-oxaziridine (1.34 g, 5.11 mmol) were dissolved in dichloromethane (20 mL) and stirred at ambient temperature for 12 hours. The reaction mixture was then purified by silica gel chromatography to give (8-cyclopentyl-2-methanesulfinyl-7-oxo-7,8-dihydro-pyrido[2,3-d]pyrimidin-6-ylmethyl)-carbamic acid benzyl ester as a white solid (0.98 g, 56.6%). $^1$H NMR δ (400 MHz, $CDCl_3$) 8.89 (s, 1H), 7.68 (s, 1H), 7.32 (m, 5H), 5.96 (m, 1H), 5.52 (t, J=6.4 Hz, 1H), 5.09 (s, 2H), 4.32 (d, J=6.3 Hz, 2H), 2.95 (s, 3H), 2.22 (m, 2H), 2.12 (m, 2H), 1.95 (m, 2H), 1.69 (m, 2H).

EXAMPLE 128

[8-Cyclopentyl-7-oxo-2-(3,4,5,6-tetrahydro-2H-[1,3']bipyridinyl-6'-ylamino)-7,8-dihydro-pyrido[2,3-d]pyrimidin-6-ylmethyl]-carbamic acid benzyl ester 8-Cyclopentyl-6-ethoxymethyl-2-methanesulfinyl-8H-pyrido[2,3-d]pyrimidin-7-one (0.90 g, 2.04 mmol) and 3,4,5,6-tetrahydro-2H-[1,3']bipyridinyl-6'-ylamine (0.497 g, 2.82 mmol) were heated to reflux in toluene (10 mL) for 16 hours. The reaction mixture was cooled to room temperature and the precipitate that formed was filtered off and washed with toluene (2×4 mL) to give [8-cyclopentyl-7-oxo-2-(3,4,5,6-tetrahydro-2H-[1,3']bipyridinyl-6'-ylamino)-7,8-dihydro-pyrido[2,3-d]pyrimidin-6-ylmethyl]-carbamic acid benzyl ester (0.320 g, 28.3%). $^1$H NMR δ (400 MHz, $CDCl_3$) 8.55 (s, 1H), 8.12 (d, J=9.0 Hz, 1H), 8.03 (d, J=2.9 Hz, 1H), 7.95 (s, 1H), 7.54 (s, 1H), 7.27-7.35 (m, 5H), 5.88 (m, 1H), 5.62 (t, J=6.1 Hz, 1H), 5.09 (s, 2H), 4.25 (d, J=6.4 Hz, 2H), 2.34 (m, 2H), 2.04 (m, 2H), 1.88 (m, 2H), 1.71 (m, 5H), 1.60 (m, 3H).

EXAMPLE 129

8-Cyclopentyl-2-[5-(2,6-dimethyl-morpholin-4-yl)-pyridin-2-ylamino]-6-(1-ethoxy-vinyl)-5-methyl-8H-pyrido[2,3-d]pyrimidin-7-one 6-Bromo-8-cyclopentyl-2-[5-(2,6-dimethyl-morpholin-4-yl)-pyridin-2-ylamino]-5-methyl-8H-pyrido[2,3-d]pyrimidin-7-one (0.062 g, 0.121 mmol), tetrakis(triphenylphosphine)palladium (0.017 g, 0.015 mmol) and tributyl-(1-ethoxy-vinyl)-stannane (0.068 mg, 0.188 mmol) were dissolved in toluene (2 mL) and slowly brought to reflux for 12 hours. Additional tetrakis(triphenylphosphine)palladium (0.010) was added and the reaction brought to reflux for 16 hours. The reaction mixture was cooled and purified by silica gel chromatography to 8-cyclopentyl-2-[5-(2,6-dimethyl-morpholin-4-yl)-pyridin-2-ylamino]-6-(1-ethoxy-vinyl)-5-methyl-8H-pyrido[2,3-d]pyrimidin-7-one as a yellow solid (0.055 g, 90.2%). $^1$H NMR δ (400 MHz, $CDCl_3$) 8.72 (s, 1H), 8.17 (d, J=9.0 Hz, 1H), 7.99 (d, J=2.9 Hz, 1H), 7.83 (s, 1H), 7.29 (dd, J=2.9, 9.0 Hz, 1H), 5.89 (m, 1H), 4.51 (d, J=2.5 Hz, 1H), 4.17 (d, J=2.4 Hz, 1H), 3.93 (q, J=7.1 Hz, 2H), 3.83 (m, 2H), 3.37 (d, J=10.3 Hz, 2H), 2.44 (dd, J=10.5, 10.5, 2H), 2.41 (s, 3H), 2.34 (m, 2H), 2.06 (m, 2H), 1.84 (m, 2H), 1.65 (m, 2H), 1.36 (t, J=7.1 Hz, 3H), 1.26 (d, J=6.4 Hz, 6H).

EXAMPLE 130

6-Acetyl-8-cyclopentyl-2-[5-(2,6-dimethyl-morpholin-4-yl)-pyridin-2-ylamino]-5-methyl-8H-pyrido[2,3-d]pyrimidin-7-one 8-Cyclopentyl-2-[5-(2,6-dimethyl-morpholin-4-yl)-pyridin-2-ylamino]-6-(1-ethoxy-vinyl)-5-methyl-8H-pyrido[2,3-d]pyrimidin-7-one (0.055 g, 0.109 mmol) was dissolved in ethyl acetate (3 mL) and 1 N aqueous HCl (2 mL) and stirred at room temperature for 48 hours. The reaction mixture was diluted with dichloromethane and aqueous $NaHCO_3$. The layers were separated and the organic layer was dried over $MgSO_4$, filtered, and the solvent evaporated to give 6-acetyl-8-cyclopentyl-2-[5-(2,6-dimethyl-morpholin-4-yl)-pyridin-2-ylamino]-5-methyl-8H-pyrido[2,3-d]pyrimidin-7-one (0.020 g, 38.4%). MS (APCI) Calc'd for M+1: 477.3. Found: 477.2. $^1$H NMR δ (400 MHz, $CDCl_3$) 8.79 (s, 1H), 8.1 (d, J=9.0 Hz, 1H), 8.00 (d, J=2.7 Hz, 1H), 7.90 (s, 1H), 7.30 (dd, J=3.1, 9.3 Hz, 1H), 5.87 (m, 1H), 3.83 (m, 2H), 3.37 (d, J=10.0 Hz, 2H), 2.54 (s, 3H), 2.46 (dd, J=11.7, 11.7, 2H), 2.37 (s, 3H), 2.32 (m, 2H), 2.05 (m, 2H), 1.87 (m, 2H), 1.68 (m, 2H), 1.27 (d, J=6.4 Hz, 6H).

EXAMPLE 131

8-Cyclopentyl-6-methyl-2-methylsulfanyl-8H-pyrido[2,3-d]pyrimidin-7-one 2-(Diethoxy-phosphoryl)-propionic acid ethyl ester (15.24 g, 64 mmol) was dissolved in tetrahydrofuran (100 mL) to which n-butyl lithium (47.7 mL, 119 mmol, 2.5 M in hexanes) was slowly added at −70° C. 4-Cyclopentylamino-2-methylsulfanyl-pyrimidine-5-carbaldehyde (15 g, 63 mmol) was dissolved in tetrahydrofuran (70 mL) then added to the reaction mixture allowing the reaction to warm to −40° C. After 3 hours the reaction was warmed to room temperature, poured into cold 1 N citric acid and extracted with diethyl ether. The organic layer was washed with brine, dried over $MgSO_4$, filtered and concentrated to give a yellow oil which was purified by silica gel chromatography. The resulting oil was dissolved to 1,8-diazabicyclo[5.4.0]undec-7-ene (75 mL) and heated to 150° C. for 4 hours. The reaction mixture was cooled to room temperature, diluted with ethyl acetate (350 mL), washed with 5% HCl and brine, dried over $MgSO_4$, then filtered and concentrated in vacuo The remaining residue was diluted with diethyl ether and the precipitated solid was filtered off to give 8-cyclopentyl-6-methyl-2-methylsulfanyl-8H-pyrido[2,3-d]pyrimidin-7-one as a white solid (6.33 g, 31.3%). $^1$H NMR δ (400 MHz, $CDCl_3$) 8.52 (s, 1H), 7.39 (d, J=1.2 Hz, 1H), 5.96 (m, 1H), 2.59 (s, 3H), 2.30 (m, 2H), 2.19 (d, J =1.2 Hz, 3H), 2.07 (m, 2H), 1.86 (m, 2H), 1.67 (m, 2H).

EXAMPLE 132

8-Cyclopentyl-2-methanesulfinyl-6-methyl-8H-pyrido[2,3-d]pyrimidin-7-one

8-Cyclopentyl-6-methyl-2-methylsulfanyl-8H-pyrido[2,3-d]pyrimidin-7-one (2.56 g, 9.30 mmol) was dissolved in dichloromethane (17 mL) and methanol (17 mL) to which 2-benzenesulfonyl-3-phenyl-oxaziridine was added and the reaction mixture was stirred for 16 hours. The solvent was removed and diethyl ether added. The precipitated solid was collected by filtration to give 8-cyclopentyl-2-methanesulfinyl-6-methyl-8H-pyrido[2,3-d]pyrimidin-7-one as a white solid (2.30 g, 84.8%). $^1$H NMR δ (400 MHz, $CDCl_3$) 8.85 (s, 1H), 7.54 (s, 1H), 5.99, (m, 1H), 2.95 (s, 3H), 2.27 (d, J=1.2 Hz, 3H), 2.24 (m, 2H), 2.13 (m, 2H), 1.94 (m, 2H), 1.70 (m, 2H).

EXAMPLE 133

6-Bromo-8-cyclopentyl-2-(4-methoxy-benzylamino)-5-methyl-8H-pyrido[2,3-d]pyrimidin-7-one A suspension of 6-bromo-8-cyclopentyl-2-methanesulfinyl-5-methyl-8H-pyrido[2,3-d]pyrimidin-7-one (1.00 g, 2.70 mmol) and 4-methoxybenzylamine (0.39 mL, 4.0 mmol) in toluene (15 mL) was heated under reflux for 2 hours. The solution was cooled, and the resulting solid was collected by filtration to give 6-bromo-8-cyclopentyl-2-(4-methoxy-benzylamino)-5-methyl-8H-pyrido[2,3-d]pyrimidin-7-one (1.04 g, 86.4%). $^1$H NMR δ (400 MHz, $CDCl_3$) 1.6 (m, 2H), 1.8 (m, 2H), 2.0 (m, 2H), 2.2 (m, 2H), 2.53 (s, 3H), 3.79 (s, 3H), 4.59 (m, 2H), 5.96 (m, 1H), 6.1 (m, 1H), 6.86 (d, J=8.3 Hz, 2H), 7.27 (d, J=8.1 Hz, 2H), 8.5 (br s, 1H). MS (APCI) ($C_{21}H_{23}Br_1N_4O_2$): Calc for M+H, 443.1; Found, 443.1

EXAMPLE 134

8-Cyclopentyl-6-(1-ethoxy-vinyl-2-(4-methoxy-benzylamino))-5-methyl-8H-pyrido[2,3-d]pyrimidin-7-one A suspension of 6-bromo-8-cyclopentyl-2-(4-methoxy-benzylamino)-5-methyl-8H-pyrido[2,3-d]pyrimidin-7-one (0.44 g, 1.0 mmol), tributyl(1-ethoxyvinyl)tin (0.53 mL, 1.6 mmol), and tetrakis(triphenylphosphine)palladium(0) (0.14 g, 0.12 mmol) in toluene (5 mL) was heated under reflux for two hours. The suspension was cooled to room temperature and filtered. The filtrate was concentrated and the residue triturated with hexane to give a solid. Chromatography on silica gel (5 to 50% ethyl acetate in hexane over fifteen minutes) gave 8-cyclopentyl-6-(1-ethoxy-vinyl-2-(4-methoxy-benzylamino))-5-methyl-8H-pyrido[2,3-d]pyrimidin-7-one (0.35 g, 81%). $^1$H NMR δ (400 MHz, $CDCl_3$) 1.34 (t, J=7.1 Hz, 3H), 1.6 (m, 2H), 1.7 (m, 2H), 2.0 (m, 2H), 2.3 (m, 2H), 2.34 (s, 3H), 3.78 (s, 3H), 3.90 (q, J=7.0 Hz, 2H), 4.13 (d, J=2.2 Hz, 1H), 4.48 (d, J=2.2 Hz, 1H), 4.59 (d, J=5.4 Hz, 2H), 5.87 (m, 1H), 6.0 (m, 1H), 6.86 (d, J=8.6 Hz, 2H), 7.27 (d, J=8.6 Hz, 2H), 8.5 (br s, 1H). MS (APCI) ($C_{25}H_{30}N_4O_3$) Calc for M+H, 435.2; Found, 435.3.

EXAMPLE 135

6-Acetyl-2-amino-8-cyclopentyl-5-methyl-8H-pyrido[2,3-d]pyrimidin-7-one

A solution of 8-cyclopentyl-6-(1-ethoxy-vinyl-2-(4-methoxy-benzylamino)-5-methyl-8H-pyrido[2,3-d]pyrimidin-7-one (2.90 g, 6.67 mmol) in trifluoroacetic acid (50 mL) was heated under relux for 8 hours. After allowing to cool, the solution was concentrated in vacuo and diluted with water. The resulting suspension was made basic with 1 N NaOH, and the solid was collected by filtration. The solid was dissolved in $CH_2Cl_2$ and chromatographed on silica gel eluting with ethyl acetate to give 6-acetyl-2-amino-8-cyclopentyl-5-methyl-8H-pyrido[2,3-d]pyrimidin-7-one (1.51 g, 79.1%). mp 182-186° C. $^1$H NMR δ (400 MHz, $CDCl_3$) 1.6 (m, 2H), 1.8 (m, 2H), 2.0 (m, 2H), 2.3 (m, 2H), 2.32 (s, 3H), 2.52 (s, 3H), 5.34 (s, 2H), 5.84 (m, 1H), 8.63 (s, 1H). MS (APCI) ($C_{15}H_{18}N_4O_2$) Calc for M+H, 287.1; Found, 287.1.

EXAMPLE 136

Biological Assays

To determine the inhibitory potency and selectivity of compounds of the present invention against Cdk4 and related kinases, compounds were evaluated in standard assays routinely used to measure inhibition of cyclin-dependent kinase enzymes and other protein kinases (see for example D. W. Fry et al., J. Biol. Chem. 2001, 276, 16617-16623). The assays were carried out as described below.

Assay for Inhibition of Cdk2/Cyclin A

Cdk2 enzyme assays for $IC_{50}$ determinations and kinetic evaluation are performed as follows. 96-well filter plates (Millipore MADVN6550) are used. The final assay volume is 0.1 mL containing buffer A (20 mM TRIS (tris[hydroxymethyl]aminomethane) (pH 7.4), 50 mM NaCl, 1 mM dithiothreitol, 10 mM $MgCl_2$), 12 mM ATP containing 0.25 μCi [$^{32}$P]ATP, 20 ng Cdk2/cyclin A, 1 μg retinoblastoma protein, and the test compound at appropriate dilutions in buffer A (Buffer A alone without added test compound was employed as a control for no inhibition. Buffer A containing excess EDTA was used to determine the level of background $^{32}$P in the absence of enzyme activity). All components except the ATP are added to the wells, and the plate is placed on a plate mixer for 2 minutes. The reaction is initiated by addition of [$^{32}$P]ATP, and the plate is incubated at 25° C. for 15 minutes. The reaction is terminated by addition of 0.1 mL 20% TCA. The plate is kept at 4° C. for at least 1 hour to allow the substrate to precipitate. The wells are then washed five times with 0.2 mL 10% TCA, and $^{32}$P incorporation is determined with a beta plate counter (Wallac Inc., Gaithersburg, Md.). The $IC_{50}$ of the test compound was determined using the median effect method (Chou, T-C and Talalay, P. Applications of the median effect principle for the assessment of low-dose risk of carcinogens and for the quantitation of synergism and antagonism of chemotherapeutic agents. In: New Avenues in Developmental Cancer Chemotherapy (Eds. Harrap, K. T. and Connors, T. A.), pp. 37-64. Academic Press, New York, 1987).

Assay for Inhibition of Cdk4/Cyclin D

The Cdk4 enzyme assay for $IC_{50}$ determination and kinetic evaluation is performed as follows. 96-well filter plates (Millipore MADVN6550) are used. The total volume is 0.1 mL containing buffer A (20 mM TRIS (tris[hydroxymethyl]aminomethane) (pH 7.4), 50 mM NaCl, 1 mM dithiothreitol, 10 mM $MgCl_2$), 25 μM ATP containing 0.25 μCi [$^{32}$P]ATP, 20 ng Cdk4, 1 μg retinoblastoma protein and the test compound at appropriate dilutions in buffer A. Buffer A alone without added test compound was employed as a control for no inhibition. Buffer A containing excess EDTA was used to determine the level of background $^{32}$P in the absence of enzyme activity. All components except the ATP are added to the wells, and the plate is placed on a plate mixer for 2 minutes. The reaction is started by adding [$^{32}$P]ATP, and the plate is incubated at 25° C. for 15 minutes. The reaction is terminated by addition of 0.1 mL 20% trichloroacetic acid (TCA). The plate is kept at 4° C. for at least 1 hour to allow the substrate to precipitate. The wells are then washed five times with 0.2 mL 10% TCA, and $^{32}$P incorporation is determined with a beta plate counter (Wallac Inc., Gaithersburg, Md.). The $IC_{50}$ of the test compound was determined using the median effect method (Chou, T-C and Talalay, P. Applications of the median effect principle for the assessment of low-dose risk of carcinogens and for the quantitation of synergism and antagonism of chemotherapeutic agents. In: New Avenues in Developmental Cancer Chemotherapy (Eds. Harrap, K. T. and Connors, T. A.), pp. 37-64. Academic Press, New York, 1987).

Assay for Inhibition of FGFr

For FGF receptor (FGFr) tyrosine kinase assays 96-well plates (100 μL/incubation/well), and conditions are optimized to measure the incorporation of $^{32}P$ from [$\gamma^{32}P$]ATP into a glutamate-tyrosine co-polymer substrate. Briefly, to each well is added 82.5 μL incubation buffer B (25 mM Hepes (pH 7.0), 150 mM NaCl, 0.1% Triton X-100, 0.2 mM PMSF, 0.2 mM $Na_3VO_4$, 10 mM $MnCl_2$) and 750 μg/mL Poly (4:1) glutamate-tyrosine followed by 2.5 μL of the test compound in buffer B and 5 μL of a 7.5 μg/μL FGFr solution to initiate the reaction. Following a 10-minute incubation at 25° C., 10 mL [$\gamma^{32}P$]ATP (0.4 μCi plus 50 μM ATP) is added to each well, and samples are incubated for an additional 10 minutes at 25° C. The reaction is terminated by the addition of 100 μL 30% trichloroacetic acid (TCA) containing 20 mM sodium pyrophosphate and precipitation of material onto glass fiber mats (Wallac). Filters are washed three times with 15% TCA containing 100 mM sodium pyrophosphate, and the radioactivity retained on the filters is counted in a Wallac 1250 Betaplate reader. Nonspecific activity is defined as radioactivity retained on the filters following incubation of samples with buffer alone (no enzyme). Specific enzymatic activity (enzyme plus buffer) is defined as total activity minus nonspecific activity. The concentration of a test compound that inhibited specific activity by 50% ($IC_{50}$) is determined based on the inhibition curve.

Results from the foregoing assays for several compounds of the present invention compared to compounds disclosed in WO 98/33798 are presented in Table 1. For comparison, data are also provided for C2 phenylamino analogs of each Example compound where available. These analogs differ from the example compounds by the replacement of the pyridyl ring nitrogen atom by CH and are distinguished from compounds of the instant invention by a superscript prime (for example the phenylamino analog of Example compound 1 is denoted 1'). These C2-phenylamino pyridopyrimidinones were previously described in patent applications WO 98/33798 and WO 01/70741.

TABLE 1

| EXAMPLE | Cdk4 IC50 (μM) | Cdk2 IC50 (μM) | FGFr IC50 (μM) |
|---|---|---|---|
| 1' | 0.21 | 0.021 | 2.98 |
| 1 | 0.145 | 5.01 | >5 |
| 3' | 0.002 | 0.043 | 0.08 |
| 3 | 0.016 | 6.052 | 1.032 |
| 5' | 0.001 | 0.142 | 0.086 |
| 5 | 0.019 | NA | 0.99 |
| 7' | 0.004 | 5.950 | 0.042 |
| 7 | 0.595 | >5 | NA |
| 11' | 0.005 | 0.095 | 0.088 |
| 11 | 0.012 | NA | 2.12 |
| 12 | 0.175 | NA | NA |
| 13 | >5 | NA | NA |
| 14 | 0.260 | NA | NA |
| 15' | 0.005 | 0.439 | 1.74 |
| 15 | 0.160 | >5 | >5 |
| 18' | 0.015 | 0.139 | NA |
| 18 | 0.051 | >5 | NA |
| 20' | 0.002 | 0.059 | 0.153 |
| 20 | 0.027 | 4.05 | 1.605 |

TABLE 1-continued

| EXAMPLE | Cdk4 IC50 (μM) | Cdk2 IC50 (μM) | FGFr IC50 (μM) |
|---|---|---|---|
| 22' | 0.009 | 3.149 | NA |
| 22 | 1.70 | >5 | >5 |
| 24' | 0.004 | >5 | NA |
| 24 | 0.005 | >5 | >5 |
| 29' | NA | NA | NA |
| 29 | 0.013 | >5 | 4.38 |
| 31' | 0.006 | 5 | 3.943 |
| 31b | 0.049 | >5 | >5 |
| 33' | 0.006 | 0.556 | 0.535 |
| 33 | 0.123 | >5 | >5 |
| 36' | 0.006 | 0.233 | 1.83 |
| 36 | 0.011 | >5 | >5 |
| 37' | NA | NA | NA |
| 37 | >5 | >5 | >5 |
| 38' | 0.088 | 0.080 | NA |
| 38 | 0.95 | >5 | >5 |
| 50 | 0.145 | >5 | >5 |
| 51' | 0.005 | 0.179 | 0.711 |
| 51 | 0.135 | >5 | NA |
| 53' | 0.018 | >5 | 0.94 |
| 53 | 0.036 | >5 | >5 |
| 54 | 1.1 | >5 | >5 |
| 55 | 0.024 | >5 | >5 |
| 57' | 0.014 | 0.084 | >5 |
| 57 | >5 | >5 | >5 |
| 59' | 0.006 | 0.024 | 0.081 |
| 59 | 0.015 | 2.5 | 1.52 |
| 61' | 0.006 | 0.119 | 4.35 |
| 61 | 0.013 | 0.835 | 1.38 |
| 64 | 0.92 | >5 | 4.47 |
| 65 | 0.430 | 3.30 | >5 |
| 66 | 0.763 | >5 | 0.515 |
| 70 | 0.135 | >5 | >5 |
| 72 | 0.005 | >5 | |
| 74 | 0.014 | >5 | >5 |
| 75 | 0.074 | >5 | >5 |
| 77 | 0.019 | >5 | >5 |
| 81 | 0.012 | >5 | >5 |
| 82 | 0.440 | >5 | >5 |
| 84' | 0.007 | >5 | 1.078 |
| 84 | 0.580 | >5 | >5 |
| 88' | 0.020 | 1.33 | >5 |
| 88 | | | |
| 90 | 0.021 | >5 | >5 |
| 93' | 0.015 | 1.86 | >5 |
| 93 | 0.063 | >5 | >5 |
| 95' | 0.005 | 0.545 | 1.815 |
| 95 | 0.037 | >5 | >5 |
| 98 | 1.95 | >5 | >5 |
| 100 | 0.004 | >5 | >5 |
| 103 | >5 | >5 | NA |
| 105 | 0.005 | >5 | >5 |
| 108' | 0.007 | 0.205 | 0.136 |
| 108 | 0.124 | >5 | >5 |
| 112 | 0.031 | >5 | >5 |
| 116 | 0.018 | >5 | >5 |
| 120 | 0.013 | 3.800 | 2.470 |
| 124 | 0.545 | >5 | >5 |
| 125 | 0.018 | >5 | >5 |
| 130 | 0.030 | >5 | >5 |

FORMULATION EXAMPLES

As noted above, the invention compounds will typically be formulated with common excipients, diluents, and carriers to provide compositions that are well-suited for convenient administration to mammals. The following examples illustrate typical compositions that are provided in a further embodiment of this invention.

EXAMPLE 137

Formulations

| Tablet Formulation | |
|---|---|
| Ingredient | Amount |
| Compound 36b of Example 36 | 50 mg |
| Lactose | 80 mg |
| Cornstarch (for mix) | 10 mg |
| Cornstarch (for paste) | 8 mg |
| Magnesium Stearate (1%) | 2 mg |
| | 150 mg |

A compound of the present invention is mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for prevention and treatment of cancer.

EXAMPLE 138

Parenteral Solution

To a solution of 700 mL of propylene glycol and 200 mL of water for injection is added 20.0 g of compound 36 b of the present invention. The mixture is stirred and the pH is adjusted to 5.5 with hydrochloric acid. The volume is adjusted to 1000 mL with water for injection. The solution is sterilized, filled into 5.0 mL ampoules, each containing 2.0 mL (40 mg of compound), and sealed under nitrogen. The solution is administered by injection to a patient suffering from cancer and in need of treatment.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

[1. A compound of the formula I:

I

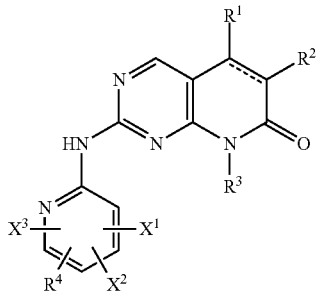

or a pharmaceutically acceptable salt thereof, wherein:

the dashed line represents an optional bond, $X^1$, $X^2$, and $X^3$ are independently hydrogen, halogen, $C_1$-$C_6$ alkyl, $C_1$-$C_6$ haloalkyl, $C_1$-$C_8$ alkoxy, $C_1$-$C_8$ alkoxyalkyl, CN, $NO_2$, $OR^5$, $NR^5R^6$, $CO_2R^5$, $COR^5$, $S(O)_nR^5$, $CONR^5R^6$, $NR^5COR^6$, $NR^5SO_2R^6$, $SO_2NR^5R^6$, and $P(O)(OR^5)(OR^6)$; with the proviso that at least one of $X^1$, $X^2$, and $X^3$ must be hydrogen;

n=0-2;

$R^1$ is $C_1$-$C_6$ alkyl;

$R^2$ and $R^4$ are independently selected from hydrogen, halogen, $C_1$-$C_8$ alkyl, $C_3$-$C_7$ cycloalkyl, $C_1$-$C_8$ alkoxy, $C_1$-$C_8$ alkoxyalkyl, $C_1$-$C_8$ haloalkyl, $C_1$-$C_8$ hydroxyalkyl, $C_2$-$C_8$ alkenyl, $C_2$-$C_8$ alkynyl, nitrile, nitro, $OR^5$, $SR^5$, $NR^5R^6$, $N(O)R^5R^6$, $P(O)(OR^5)(OR^6)$, $(CR^5R^6)_m NR^7R^8$, $COR^5$, $(CR^4R^5)_mC(O)R^7$, $CO_2R^5$, $CONR^5R^6$, $C(O)NR^5SO_2R^6$, $NR^5SO_2R^6$, $C(O)NR^5OR^6$, $S(O)_nR^5$, $SO_2NR^5R^6$, $P(O)(OR^5)(OR^6)$, $(CR^5R^6)_mP(O)(OR^7)(OR^8)$, $(CR^5R^6)_m$-aryl, $(CR^5R^6)_m$-heteroaryl, $-T(CH_2)_m QR^5$, $—C(O)T(CH_2)_mQR^5$, $NR^5C(O)T(CH_2)_mQR^5$, and $—CR^5{=}CR^6C(O)R^7$; or T is O, S, $NR^7$, $N(O)R^7$, $NR^7R^8W$, or $CR^7R^8$;

Q is O, S, $NR^7$, $N(O)R^7$, $NR^7R^8W$, $CO_2$, $O(CH_2)_m$-heteroaryl, $O(CH_2)_mS(O)_nR^8$, $(CH_2)$-heteroaryl, or a carbocyclic group containing from 3-7 ring members, up to four of which ring members are optionally heteroatoms independently selected from oxygen, sulfur, and nitrogen, provided, however, that there is at least one carbon atom in the carbocyclic ring and that if there are two or more ring oxygen atoms, the ring oxygen atoms are not adjacent to one another, wherein the carbocyclic group is unsubstituted or substituted with one, two, or three groups independently selected from halogen, hydroxy, hydroxyalkyl, lower alkyl, lower alkoxy, alkoxycarbonyl, alkylcarbonyl, alkylcarbonylamino, aminoalkyl, trifluoromethyl, N-hydroxyacetamide, trifluoromethylalkyl, amino, and mono or dialkylamino;

W is an anion selected from the group consisting of chloride, bromide, trifluoroacetate, and triethylammonium;

m=0-6;

$R^4$ and one of $X^1$, $X^2$ and $X^3$ may form an aromatic ring containing up to three heteroatoms independently selected from oxygen, sulfur, and nitrogen, and optionally substituted by up to 4 groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, mono- or dialkylamino, N-hydroxyacetamido, aryl, heteroaryl, carboxyalkyl, nitrile, $NR^7SO_2R^8$, $C(O)NR^7R^8$, $NR^7C(O)R^8$, $C(O)OR^7$, $C(O)NR^7SO_2R^8$, $(CH_2)_mS(O)_nR^7$, $(CH_2)_m$-heteroaryl, $O(CH_2)_m$-heteroaryl, $(CH_2)_mC(O)NR^7R^8$, $O(CH_2)_mC(O)OR^7$, $(CH_2)_mSO_2NR^7R^8$, and $C(O)R^7$;

$R^3$ is $C_1$-$C_8$ alkoxy, $C_3$-$C_7$ cycloalkyl, or $C_3$-$C_7$-heterocyclyl;

$R^5$ and $R^6$ independently are hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heterarylalkyl; or $R^5$ and $R^6$, when attached to the same nitrogen atom, taken together with the nitrogen to which they are attached, form a heterocyclic ring containing from 3-8 ring members, up to four of which members can optionally be replaced with heteroatoms independently selected from oxygen, sulfur, S(O), $S(O)_2$, and nitrogen, provided, however, that there is at least one carbon atom in the heterocyclic ring and that if there are two or more ring oxygen atoms, the ring oxygen atoms are not adjacent to one another, wherein the heterocyclic group is unsubstituted or substituted with one, two or three groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, nitrile, mono- or dialkylamino, N-hydroxyacetamido, aryl, heteroaryl, carboxyalkyl, $NR^7SO_2R^8$, $C(O)NR^7R^8$, $NR^7C(O)R^8$, $C(O)OR^7$, $C(O)NR^7SO_2R^8$, $(CH_2)_mS(O)_nR^7$, $(CH_2)_m$-heteroaryl, $O(CH_2)_m$-heteroaryl, $(CH_2)_mC(O)NR^7R^8$, $O(CH_2)_mC(O)OR^7$, and $(CH_2)SO_2NR^7R^8$;

$R^7$ and $R^8$ are, independently, hydrogen, $C_1$-$C_8$ alkyl, $C_2$-$C_8$ alkenyl, $C_2$-$C_8$ alkynyl, arylalkyl, cycloalkyl, heterocycloalkyl, aryl, heteroaryl, or heterarylalkyl; or $R^7$ and $R^8$, when attached to the same nitrogen atom, taken together with the nitrogen to which they are attached, may form a heterocyclic ring containing from 3-8 ring members, up to four of which members are optionally heteroatoms independently selected from oxygen, sulfur, S(O), $S(O)_2$, and nitrogen, provided, however, that there is at least one carbon atom in the heterocyclic ring and that if there are two or more ring oxygen atoms, the ring oxygen atoms are not adjacent to one another, wherein the heterocyclic group is unsubstituted or substituted with one, two or three groups independently selected from halogen, hydroxy, hydroxyalkyl, lower alkyl, lower alkoxy, alkoxycarbonyl, alkylcarbonyl, alkylcarbonylamino, aminoalkyl, aminoalkylcarbonyl, trifluoromethyl, trifluoromethylalkyl, trifluoromethylalkylaminoalkyl, amino, nitrile, mono- or dialkylamino, N-hydroxyacetamido, aryl, heteroaryl, carboxyalkyl.]

2. A compound of [claim 1, having the following structure] *Formula II*:

II

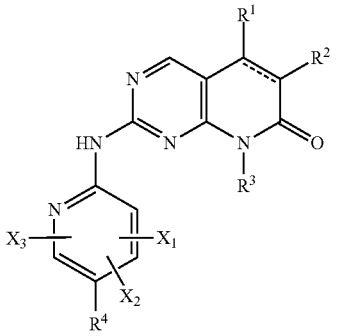

[wherein $R^1$, $R^2$, $R^3$, $R^4$, $X^1$, $X^2$, and $X^3$ are as defined for formula I] *or a pharmaceutically acceptable salt thereof, wherein:*

*the dashed line represents a bond;*

*$X^1$, $X^2$, and $X^3$ are hydrogen;*

*$R^1$ is methyl;*

*$R^2$ is acetyl;*

*$R^3$ is cyclopentyl;*

*$R^4$ is $NR^5R^6$; and*

*$R^5$ and $R^6$, taken together with the nitrogen to which they are attached, form a heterocyclic ring containing from 3-8 ring members, up to four of which members can optionally be replaced with heteroatoms independently selected from oxygen, sulfur, S(O), $S(O)_2$, and nitrogen, provided that there is at least one carbon atom in the heterocyclic ring and that if there are two or more ring oxygen atoms, the ring oxygen atoms are not adjacent to one another; wherein the heterocyclic group is unsubstituted or substituted with one, two, or three groups independently selected from the group consisting of hydroxyl, $C_1$-$C_4$ alkyl, and amino.*

[3. A compound of claim 1 or claim 2 wherein $R^3$ is a cyclopentyl group.]

[4. A compound according to claim 2 wherein $R^1$ is methyl.]

[5. A compound according to claim 2 wherein $R^2$ is $(CO)CH_3$.]

6. A compound [according to claim 1] selected from the group consisting of:

6-Acetyl-8-cyclopentyl-2-[5-(3,5-dimethyl-piperazin-1-yl)-pyridin-2-ylamino]-5-methyl-8H-pyrido[2,3-d]pyrimidin-7-one, 6-Acetyl-8-cyclopentyl-2-[5-(3,3-dimethyl-piperazin-1-yl)-pyridin-2-ylamino]-5-methyl-8H-pyrido[2,3-d]pyrimidin-7-one, 6-Acetyl-8-cyclopentyl-5-methyl-2-[5-(4-methyl-piperazin-1-yl)-pyridin-2-ylamino]-8H-pyrido[2,3-d]pyrimidin-7-one, 6-Acetyl-2-[5-(3-amino-pyrrolidin-1-yl)-pyridin-2-ylamino]-8-cyclopentyl-5-methyl-8H-pyrido[2,3-d]pyrimidin-7-one, 6-Bromo-8-cyclopentyl-5-methyl-2-(5-morpholin-4-yl-pyridin-2-ylamino)-8H-pyrido[2,3-d]pyrimidin-7-one, 2-{5-[Bis-(2-methoxy-ethyl)-amino]-pyridin-2-ylamino}-6-bromo-8-cyclopentyl-5-methyl-8H-pyrido[2,3-d]pyrimidin-7-one, 6-Acetyl-8-cyclopentyl-5-methyl-2-(5-morpholin-4-yl-pyridin-2-ylamino)-8H-pyrido[2,3-d]pyrimidin-7-one, 6-Acetyl-2-{5-[bis-(2-methoxy-ethyl)-amino]-pyridin-2-ylamino}-8-cyclopentyl-5-methyl-8H-pyrido[2,3-d]pyrimidin-7-one, 4-[6-(8-Cyclopentyl-6-iodo-5-methyl-7-oxo-7,8-dihydro-pyrido[2,3-d]pyrimidin-2-ylamino)-pyridin-3-yl]-piperazine-1-carboxylic acid tert-butyl ester, 8-Cyclopentyl-6-iodo-5-methyl-2-(5-piperazin-1-yl-pyridin-2-ylamino)-8H-pyrido[2,3-d]pyrimidin-7-one,

[2-(5-[Bis-(2-methoxy-ethyl)-amino]-pyridin-2-ylamino]-6-bromo-8-cyclopentyl-5-methyl-8H-pyrido[2,3-d]pyrimidin-7-one,]

6-Acetyl-2-{5-[bis-(2-methoxy-ethyl)-amino]-pyridin-2-ylamino}-8-cyclopentyl-5-methyl-8H-pyrido[2,3-d]pyrimidin-7-one, 6-Bromo-8-cyclopentyl-5-methyl-2-(pyridin-2-ylamino)-8H-pyrido[2,3-d]pyrimidin-7-one, 6-Bromo-8-cyclopentyl-5-methyl-2-[5-(4-methyl-piperazin-1-yl)-pyridin-2-ylamino]-8H-pyrido[2,3-d]pyrimidin-7-one, 8-Cyclopentyl-6-(1-ethoxy-vinyl)-5-methyl-2-[5-(4-methyl-piperazin-1-yl)-pyridin-2-ylamino]-8H-pyrido[2,3-d]pyrimidin-7-one, (1-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-pyrrolidin-3-yl)-carbamic acid tert-butyl ester, 6-Acetyl-8-cyclopentyl-2-(4-hydroxy-3,4,5,6-tetrahydro-2H-[1,3']bipyridinyl-6'-ylamino)-5-methyl-8H-pyrido[2,3-d]pyrimidin-7-one, 4-[6-(6-Bromo-8-cyclopentyl-5-methyl-7-oxo-7,8-dihydro-pyrido[2,3-d]pyrimidin-2-ylamino)-pyridin-3-yl]-azepane-1-carboxylic acid tert-butyl ester, 6-Bromo-8-cyclopentyl-2-(5-[1,4]diazepan-1-yl-pyridin-2-ylamino)-5-methyl-8H-pyrido[2,3-d]pyrimidin-7-one, 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-[1,4]diazepane-1-carboxylic acid tert-butyl ester, 6-Acetyl-8-cyclopentyl-2-(5-[1,4]diazepan-1-yl-pyridin-2-ylamino)-5-methyl-8H-pyrido[2,3-d]pyrimidin-7-one,

[6-Acetyl-8-cyclopentyl-5-methyl-2-(pyridin-2-ylamino)-8H-pyrido[2,3-d]pyrimindin-7-one] *6-Acetyl-8-cyclopentyl-5-methyl-2-(pyridin-2-ylamino)-8H-pyrido[2,3-d]pyrimidin-7-one*, 4-[6-(8-Cyclopentyl-5-methyl-7-oxo-7,8-dihydro-pyrido[2,3-d]pyrimidin-2-ylamino)-pyridin-3-yl]-piperazine-1-carboxylic acid tert-butyl ester, 8-Cyclopentyl-5-methyl-2-(5-piperazin-4-yl-pyridin-2-ylamino)-8H-pyrido[2,3-d]pyrimidin-7-one, 4-[6-(6-Bromo-8-cyclopentyl-5-methyl-7-oxo-7,8-dihydro-pyrido[2,3-d]pyrimidin-2-ylamino)-pyridin-3-yl]-2,2-dimethyl-piperazine-1-carboxylic acid tert-butyl ester,

[6-Bromo-8-cyclopentyl-2-[5-(3,3-dimethyl-piperazin-1-yl)-pyridin-2-ylamino]-5-methyl-8H-pyrido[2,3d]pyrimidin-7-one] *6-Bromo-8-cyclopentyl-2-[5-(3,3-dimethyl-piperazin-1-yl)-pyridin-2-ylamino]-5-methyl-8H-pyrido[2,3-d]pyrimidin-7-one*, 4-{6-[8-Cyclopentyl-6-(1-ethoxy-vinyl)-5-methyl-7-oxo-7,8-dihydro-pyrido[2,3-d]pyrimidin-2-ylamino]-pyridin-3-yl}-2,2-dimethyl-piperazine-1-carboxylic acid tert-butyl ester, 4-[6-(6-Bromo-8-cyclopentyl-5-methyl-7-oxo-7,8-dihydro-pyrido[2,3-d]pyrimidin-2-ylamino)-pyridin-3-yl]-2,6-dimethyl-piperazine-1-carboxylic acid tert-butyl ester, 6-Bromo-8-cyclopentyl-2-[5-(3,5-dimethyl-piperazin-1-yl)-pyridin-2-ylamino]-5-methyl-8H-pyrido[2,3-d]pyrimidin-7-one,

[4-{6-[8-Cyclopentyl-6-(1-ethoxy-vinyl)-5-methyl-7-oxo-7,8-dihydro-pyrido[2,3-d]pyrimindin-2-ylamino]-pyridin-3-yl}-2,6-dimethyl-piperazine-1-carboxylic acid tert-butyl ester] *4-{6-[8-Cyclopentyl-6-(1-ethoxy-vinyl)-5-methyl--oxo-7,8-dihydro-pyrido [2,3-d]pyrimidin-2-ylamino]-pyridin-3-yl}-2,6-dimethyl-piperazine-1-carboxylic acid tert-butyl ester*, 8-Cyclopentyl-6-(1-ethoxy-vinyl)-5-methyl-2-(5-morpholin-4-yl-pyridin-2-ylamino)-8H-pyrido[2,3-d]pyrimidin-7-one, 6-Bromo-8-cyclopentyl-5-methyl-2-(3,4,5,6-tetrahydro-2H-[1,3']bipyridinyl-6'-ylamino)-8H-pyrido[2,3-d]pyrimidin-7-one, 8-Cyclopentyl-6-(1-ethoxy-vinyl)-5-methyl-2-(3,4,5,6-tetrahydro-2H-[1,3']bipyridinyl-6'-ylamino)-8H-pyrido[2,3-d]pyrimidin-7-one, 6-Acetyl-8-cyclopentyl-5-methyl-2-(3,4,5,6-tetrahydro-2H-[1,3']bipyridinyl-6'-ylamino)-8H-pyrido[2,3-d]pyrimidin-7-one, 6-Bromo-8-cyclopentyl-2-[5-(2,6-dimethyl-morpholin-4-yl)-pyridin-2-ylamino]-5-methyl-8H-pyrido[2,3-d]pyrimidin-7-one, 8-Cyclopentyl-2-[5-(2,6-dimethyl-morpholin-4-yl)-pyridin-2-ylamino]-6-(1-ethoxy-vinyl)-5-methyl-8H-pyrido[2,3-d]pyrimidin-7-one, 6-Acetyl-8-cyclopentyl-2-[5-(2,6-dimethyl-morpholin-4-yl)-pyridin-2-ylamino]-5-methyl-8H-pyrido[2,3-d]pyrimidin-7-one, 8-Cyclopentyl-5-methyl-2-(5-piperazin-1-yl-pyridin-2-ylamino)-6-propionyl-8H-pyrido[2,3-d]pyrimidin-7-one,

[6-Bromo-8-cyclopentyl-5-methyl-2-(5-piperizin-1-yl-pyridin-2-ylamino)-8H-pyrido[2,3-d]pyrimidin-7-one] *6-Bromo-8-cyclopentyl-5-methyl-2-(5-piperazin-1-yl-pyridin-2-ylamino)-8H-pyrido[2,3-d]pyrimidin-7-one*, 2-[5-(4-tert-Butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester, 6-Acetyl-8-cyclopentyl-5-methyl-2-(5-piperazin-1-yl-pyridin-2-ylamino)-8H-pyrido[2,3-d]pyrimidin-7-one,

[6-Bromo-8-cyclopentyl-5-methyl-2-pyridin-2-ylamino)-8H-pyrido[2,3-d]pyrimidin-7-one] *6-Bromo-8-cyclopentyl-5-methyl-2-(pyridin-2-ylamino)-8H-pyrido[2,3-d]pyrimidin-7-one*, 6-Acetyl-8-cyclopentyl-2-[5-(3-ethylamino-pyrrolidin-1-yl)-pyridin-2-ylamino]-5-methyl-8H-pyrido[2,3-d]pyrimidin-7-one, 6-Acetyl-8-cyclopentyl-5-methyl-2-(5-pyrrolidin-1-yl-pyridin-2-ylamino)-8H-pyrido[2,3-d]pyrimidin-7-one, 6-Acetyl-2-{5-[3-(1-amino-1-methyl-ethyl)-pyrrolidin-1-yl]-pyridin-2-ylamino}-8-cyclopentyl-5-methyl-8H-pyrido[2,3-d]pyrimidin-7-one, 1-[6-(6-Acetyl-8-cyclopentyl-5-methyl-7-oxo-7,8-dihydro-pyrido[2,3-d]pyrimidin-2-ylamino)-pyridin-3-yl]-pyrrolidine-2-carboxylic acid, 6-Acetyl-8-cyclopentyl-2-[5-(4-diethylamino-butylamino)-pyridin-2-ylamino]-5-methyl-8H-pyrido[2,3-d]pyrimidin-7-one,

[6-Bromo-8-cyclopentyl-5-methyl-2-(3,4,5,6-tetrahydro-2H-[1,3']bipyridinyl-6═-ylamino)-8H-pyrido[2,3-d]pyrimidin-7-one,]

6-Bromo-8-cyclopentyl-2-(5-diethylamino-pyridin-2-ylamino)-5-methyl-8H-pyrido[2,3-d]pyrimidin-7-one, 2-{5-[Bis-(2-hydroxy-ethyl)-amino]-pyridin-2-ylamino}-6-bromo-8-cyclopentyl-5-methyl-8H-pyrido[2,3-d]pyrimidin-7-one, 2-[5-(2-Amino-ethylamino)-pyridin-2-ylamino]-6-bromo-8-cyclopentyl-5-methyl-8H-pyrido[2,3-d]pyrimidin-7-one, 6-Bromo-8-cyclopentyl-2-(5-dimethylamino-pyridin-2-ylamino)-5-methyl-8H-pyrido[2,3-d]pyrimidin-7-one, N-[6-(6-Bromo-8-cyclopentyl-5-methyl-7-oxo-7,8-dihydro-pyrido[2,3-d]pyrimidin-2-ylamino)-pyridin-3-yl]-N-methyl-acetamide, 6-Bromo-8-cyclopentyl-2-[5-(2-methoxy-ethoxy)-pyridin-2-ylamino]-5-methyl-8H-pyrido[2,3-d]pyrimidin-7-one,

[6-Bromo-8-cyclopentyl-2-[5-(2-methoxy-ethoxymethyl)-pyridin-2-)Amino]-5-methyl-8H-pyrido[2,3-d]pyrimidin-7-one] *6-Bromo-8-cyclopentyl-2-[5-(2-methoxy-ethoxymethyl)-pyridin-2-ylamino]-5-methyl-8H-pyrido[2,3-d]pyrimidin-7-one*, 6-Bromo-8-cyclopentyl-2-[5-(2-diethylamino-ethoxy)-pyridin-2-ylamino]-5-methyl-8H-pyrido[2,3-d]pyrimidin-7-one, 6-Bromo-8-cyclopentyl-5-methyl-2-(5-pyrrolidin-1-yl-pyridin-2-ylamino)-8H-pyrido[2,3-d]pyrimidin-7-one, 6-Bromo-8-cyclopentyl-5-methyl-2-(6-methyl-5-piperazin-1-yl-pyridin-2-ylamino)-8H-pyrido[2,3-d]pyrimidin-7-one, 6-Acetyl-8-cyclopentyl-5-methyl-2-(3,4,5,6-tetrahydro-2H-[1,3']bipyridinyl-6'-ylamino)-8H-pyrido[2,3-d]pyrimidin-7-one, 6-Acetyl-8-cyclopentyl-2-(5-diethylamino-pyridin-2-ylamino)-5-methyl-8H-pyrido[2,3-d]pyrimidin-7-one, 6-Acetyl-2-{5-[bis-(2-hydroxy-ethyl)-amino]-pyridin-2-ylamino}-8-cyclopentyl-5-methyl-8H-pyrido[2,3-d]pyrimidin-7-one, 6-Acetyl-2-[5-(2-amino-ethylamino)-pyridin-2-ylamino]-8-cyclopentyl-5-methyl-8H-pyrido[2,3-d]pyrimidin-7-one, 6-Acetyl-8-cyclopentyl-2-(5-dimethylamino-pyridin-2-ylamino)-5-methyl-8H-pyrido[2,3-d]pyrimidin-7-one, N-[6-(6-Acetyl-8-cyclopentyl-5-methyl-7-oxo-7,8-dihydro-pyrido[2,3-d]pyrimidin-2-ylamino)-pyridin-3-yl]-N-methyl-acetamide, 6-Acetyl-8-cyclopentyl-2-[5-(2-methoxy-ethoxy)-pyridin-2-ylamino]-5-methyl-8H-pyrido[2,3-d]pyrimidin-7-one, 6-Acetyl-8-cyclopentyl-2-[5-(2-methoxy-ethoxymethyl)-pyridin-2-ylamino]-5-methyl-8H-pyrido[2,3-d]pyrimidin-7-one, 6-Acetyl-8-cyclopentyl-2-[5-(2-diethylamino-ethoxy)-pyridin-2-ylamino]-5-methyl-8H-pyrido[2,3-d]pyrimidin-7-one, 6-Acetyl-8-cyclopentyl-5-methyl-2-(5-pyrrolidin-1-yl-pyridin-2-ylamino)-8H-pyrido[2,3-d]pyrimidin-7-one, 6-Acetyl-8-cyclopentyl-5-methyl-2-(6-methyl-5-piperazin-1-yl-pyridin-2-ylamino)-8H-pyrido[2,3-d]pyrimidin-7-one, 6-Acetyl-8-cyclopentyl-2-[5-(2-methoxy-ethoxy)-pyridin-2-ylamino]-5-methyl-8H-pyrido[2,3-d]pyrimidin-7-one, 6-Acetyl-8-cyclopentyl-2-[5-(2-methoxy-ethylamino)-pyridin-2-ylamino]-5-methyl-8H-pyrido[2,3-d]pyrimidin-7-one,

[6-Acetyl-2-(5-azetidin-1-yl-pyridin-2-ylamino)-8-cyclopentyl-5-methyl-8H-pyrido[2,3-d]pyrimindin-7-one] *6-Acetyl-2-(5-azetidin-1-yl-pyridin-2-ylamino)-8-cyclopentyl-5-methyl-8H-pyrido[2,3-d]pyrimidin-7-one*, 6-Acetyl-2-(5-azepan-1-yl-pyridin-2-ylamino)-8-cyclopentyl-5-methyl-8H-pyrido[2,3-d]pyrimidin-7-one, N-[6-(6-Acetyl-8-cyclopentyl-5-methyl-7-oxo-7,8-dihydro-pyrido[2,3-d]pyrimidin-2-ylamino)-pyridin-3-yl]-acetamide, 6-Acetyl-8-cyclopentyl-5-methyl-2-(5-phenylamino-pyridin-2-ylamino)-8H-pyrido[2,3-d]pyrimidin-7-one, 6-Acetyl-8-cyclopentyl-2-[5-(4-fluoro-benzylamino)-pyridin-2-ylamino]-5-methyl-8H-pyrido[2,3-d]pyrimidin-7-one, N-[6-(6-Acetyl-8-cyclopentyl-5-methyl-7-oxo-7,8-dihydro-pyrido[2,3-d]pyrimidin-2-ylamino)-pyridin-3-yl]-methanesulfonamide, 6-Acetyl-8-cyclopentyl-2-(5-methanesulfonyl-pyridin-2-ylamino)-5-methyl-8H-pyrido[2,3-d]pyrimidin-7-one, 6-Acetyl-8-cyclopentyl-5-methyl-2-(5-phenyl-pyridin-2-ylamino)-8H-pyrido[2,3-d]pyrimidin-7-one, 6-Bromo-8-cyclopentyl-5-methyl-2-[5-(piperazine-1-carbonyl)-pyridin-2-ylamino]-8H-pyrido[2,3-d]pyrimidin-7-one, 6-Bromo-8-cyclopentyl-2-[5-(3,5-dimethyl-piperazine-1-carbonyl)-pyridin-2-ylamino]-5-methyl-8H-pyrido[2,3-d]pyrimidin-7-one, 2-[5-(3-Amino-pyrrolidine-1-carbonyl)-pyridin-2-ylamino]-6-bromo-8-cyclopentyl-5-methyl-8H-pyrido[2,3-d]pyrimidin-7-one, 6-Bromo-8-cyclopentyl-5-methyl-2-[5-(morpholine-4-carbonyl)-pyridin-2-ylamino]-8H-pyrido[2,3-d]pyrimidin-7-one, 6-Acetyl-8-cyclopentyl-5-methyl-2-[5-(piperazine-1-carbonyl)-pyridin-2-ylamino]-8H-pyrido[2,3-d]pyrimidin-7-one, 6-Acetyl-8-cyclopentyl-2-[5-(3,5-dimethyl-piperazine-1-carbonyl)-pyridin-2-ylamino]-5-methyl-8H-pyrido[2,3-d]pyrimidin-7-one, 6-Acetyl-2-[5-(3-amino-pyrrolidine-1-carbonyl)-pyridin-2-ylamino]-8-cyclopentyl-5-methyl-8H-pyrido[2,3-d]pyrimidin-7-one, 6-Acetyl-8-cyclopentyl-5-methyl-2-[5-(morpholine-4-carbonyl)-pyridin-2-ylamino]-8H-pyrido[2,3-d]pyrimidin-7-one, 6-Bromo-8-cyclopentyl-5-methyl-2-[5-(piperazine-1-sulfonyl)-pyridin-2-ylamino]-8H-pyrido[2,3-d]pyrimidin-7-one, 6-Bromo-8-cyclopentyl-5-methyl-2-[5-(morpholine-4-sulfonyl)-pyridin-2-ylamino]-8H-pyrido[2,3-d]pyrimidin-7-one, 2-[5-(3-Amino-pyrrolidine-1-sulfonyl)-pyridin-2-ylamino]-6-bromo-8-cyclopentyl-5-methyl-8H-pyrido[2,3-d]pyrimidin-7-one, 6-Bromo-8-cyclopentyl-2-[5-(3,5-dimethyl-piperazine-1-sulfonyl)-pyridin-2-ylamino]-5-methyl-8H-pyrido[2,3-d]pyrimidin-7-one, 6-Acetyl-8-cyclopentyl-5-methyl-2-[5-(piperazine-1-sulfonyl)-pyridin-2-ylamino]-8H-pyrido[2,3-d]pyrimidin-7-one, 6-Acetyl-8-cyclopentyl-5-methyl-2-[5-(morpholine-4-sulfonyl)-pyridin-2-ylamino]-8H-pyrido[2,3-d]pyrimidin-7-one, 6-Acetyl-2-[5-(3-amino-pyrrolidine-1-sulfonyl)-pyridin-2-ylamino]-8-cyclopentyl-5-methyl-8H-pyrido[2,3-d]pyrimidin-7-one, 6-Acetyl-8-cyclopentyl-2-[5-(3,5-dimethyl-piperazine-1-sulfonyl)-pyridin-2-ylamino]-5-methyl-8H-pyrido[2,3-d]pyrimidin-7-one, [and]

6-Acetyl-8-cyclopentyl-5-methyl-2-([1,6]naphthyridin-2-ylamino)-8H-pyrido[2,3-d]pyrimidin-7-one,

[6-Acetyl-8-cyclopentyl-2-[5-(1,1-dioxo-1|6-thiomorpholin-4-yl)-pyridin-2-ylamino]-5-methyl-8H-pyrido[2,3-d]pyrimidin-7-one,]

8-Cyclopentyl-6-hydroxymethyl-5-methyl-2-(5-piperazin-1-yl-pyridin-2-ylamino)-8H-pyrido[2,3-d]pyrimidin-7-one, 6-Acetyl-2-(3-chloro-5-piperazin-1-yl-pyridin-2-ylamino)-8-cyclopentyl-5-methyl-8H-pyrido[2,3-d]pyrimidin-7-one, 4-[6-Acetyl-5-methyl-7-oxo-2-(pyridin-2-ylamino)-7H-pyrido[2,3-d]pyrimidin-8-yl]-cyclohexanecarboxylic acid, 4-[6-Acetyl-2-(5-dimethylamino-pyridin-2-ylamino)-5-methyl-7-oxo-7H-pyrido[2,3-d]pyrimidin-8-yl]-cyclohexanecarboxylic acid, 6-Bromo-8-cyclopentyl-5-methyl-2-[5-(piperazine-1-sulfonyl)-pyridin-2-ylamino]-8H-pyrido[2,3-d]pyrimidin-7-one, 6-Acetyl-5-methyl-2-(5-methyl-pyridin-2-ylamino)-8-piperidin-4-yl-8H-pyrido[2,3-d]pyrimidin-7-one, *and*

6-Acetyl-2-[5-(3,4-dihydroxy-pyrrolidin-1-yl)-pyridin-2-ylamino]-8-methoxymethyl-5-methyl-8H-pyrido[2,3-d]pyrimidin-7-one.

7. A compound according to claim 1 selected from the group consisting of:

[6-Bromo-8-cyclopentyl-5-methyl-2-(5-piperizin-1-yl-pyridin-2-ylamino)-8H-pyrido[2,3-d]pyrimidin-7-one] *6-Bromo-8-cyclopentyl-5-methyl-2-(5-piperazin-1-yl-pyridin-2-ylamino)-8H-pyrido[2,3-d]pyrimidin-7-one*, 2-[5-(4-tert-Butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester, 6-Acetyl-8-cyclopentyl-5-methyl-2-(5-piperazin-1-yl-pyridin-2-ylamino)-8H-pyrido[2,3-d]pyrimidin-7-one, 6-Bromo-8-cyclopentyl-5-methyl-2-(pyridin-2-ylamino)-8H-pyrido[2,3-d]pyrimidin-7-one, and [pharmaceutilly] *pharmaceutically* acceptable salts thereof.

8. A pharmaceutically acceptable salt of 6-Acetyl-8-cyclopentyl-5-methyl-2-(5-piperazin-1-yl-pyridin-2-ylamino)-8H-pyrido[2,3-d]pyrimidin-7-one.

9. A pharmaceutical composition comprising a therapeutically effective amount of a compound according to claim [1] *2* and a pharmaceutical carrier, diluent, or excipient therefor.

*10. A compound according to claim 6 selected from the group consisting of:*

*2-[5-(4-tert-Butoxycarbonyl-piperazin-1-yl)-pyridin-2-ylamino]-8-cyclopentyl-5-methyl-7-oxo-7,8-dihydro-pyrido[2,3-d]pyrimidine-6-carboxylic acid ethyl ester, and*

*6-Acetyl-8-cyclopentyl-5-methyl-2-(5-piperazin-1-yl-pyridin-2-ylamino)-8H-pyrido[2,3-d]pyrimidin-7-one.*

*11. 6-Acetyl-8-cyclopentyl-5-methyl-2-(5-piperazin-1-yl-pyridin-2-ylamino)-8H-pyrido[2,3-d]pyrimidin-7-one or a pharmaceutically acceptable salt thereof.*

*12. A pharmaceutical composition comprising a therapeutically effective amount of 6-Acetyl-8-cyclopentyl-5-methyl-2-(5-piperazin-1-yl-pyridin-2-ylamino)-8H-pyrido[2,3-d]pyrimidin-7-one or a pharmaceutically acceptable salt thereof, and a pharmaceutical carrier, diluent, or excipient therefor.*

* * * * *